(12) United States Patent
Smejkal et al.

(10) Patent No.: US 9,282,743 B2
(45) Date of Patent: Mar. 15, 2016

(54) CHEMICAL COMPOUNDS

(75) Inventors: Tomas Smejkal, Stein (CH); Michel Muehlebach, Stein (CH)

(73) Assignee: Syngenta Participations AG, Basel (CH)

( * ) Notice: Subject to any disclaimer, the term of this patent is extended or adjusted under 35 U.S.C. 154(b) by 122 days.

(21) Appl. No.: 14/127,643

(22) PCT Filed: Jun. 22, 2012

(86) PCT No.: PCT/EP2012/062077
§ 371 (c)(1),
(2), (4) Date: Jan. 10, 2014

(87) PCT Pub. No.: WO2012/175666
PCT Pub. Date: Dec. 27, 2012

(65) Prior Publication Data
US 2014/0148339 A1 May 29, 2014

(30) Foreign Application Priority Data

Jun. 22, 2011 (EP) .................................. 11171021
May 4, 2012 (EP) .................................. 12166860

(51) Int. Cl.
*A01N 43/90* (2006.01)
*C07D 487/04* (2006.01)
*C07D 255/02* (2006.01)

(52) U.S. Cl.
CPC .............. *A01N 43/90* (2013.01); *C07D 255/02* (2013.01); *C07D 487/04* (2013.01)

(58) Field of Classification Search
CPC ............................... A01N 43/90; C07D 487/04
USPC ............ 514/405; 540/554; 504/103, 139, 219
See application file for complete search history.

(56) References Cited

U.S. PATENT DOCUMENTS

2008/0188371 A1    8/2008   Fischer et al.

OTHER PUBLICATIONS

International Search Report and Written Opinion for International Patent Application No. PCT/EP2012/062077 dated Jul. 25, 2012.

*Primary Examiner* — Brenda Coleman
(74) *Attorney, Agent, or Firm* — R. Kody Jones

(57) ABSTRACT

Compounds of formula (I) wherein the substituents are as defined in claim 1, are useful as a pesticides and herbicides.

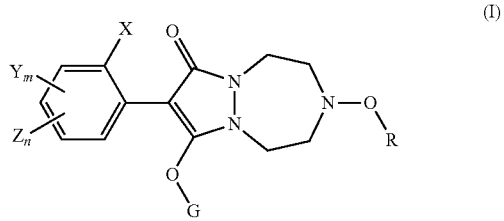

24 Claims, No Drawings

CHEMICAL COMPOUNDS

RELATED APPLICATION INFORMATION

This application is a 371 of International Application No. PCT/EP2012/062077, filed 22 Jun. 2012, which claims priority to European Patent Application No. 12166860.2 filed 04 May. 2012 and European Patent Application No. 11171021.6, filed 22 Jun. 2011, the contents of which are incorporated herein by reference herein.

The present invention relates to new substituted N-oxy pyrazolo-triazepine-dione derivatives, to processes for preparing them, to pesticidal, in particular insecticidal, acaricidal, molluscicidal and nematicidal, and herbicidal compositions comprising them, to methods of using them to combat and control pests such as insect, acarine, mollusc and nematode pests, and to methods of using them to combat and control weeds in crops of useful plants or to inhibit undesired plant growth.

It has now surprisingly been found that certain new substituted N-oxy pyrazolo-triazepine-dione derivatives have good pesticidal and herbicidal properties.

The present invention therefore provides compounds of the formula I

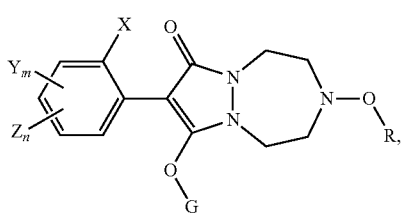

wherein
X, Y and Z, independently of each other, are $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl, halogen, phenyl or phenyl substituted by $C_{1-4}$alkyl, $C_{1-4}$haloalkyl, halogen or cyano;
m and n, independently of each other, are 0, 1, 2 or 3 and m+n is 0, 1, 2 or 3;
G is hydrogen, a metal, ammonium, sulfonium or a latentiating group;
R is hydrogen, $C_{1-6}$alkyl, $C_{1-6}$cyanoalkyl, $C_{2-6}$alkenyl, $C_{2-6}$haloalkenyl, $C_{3-6}$alkynyl, benzyl, $C_{1-4}$alkoxy($C_{1-4}$)alkyl or $C_{1-4}$alkoxy($C_{1-4}$)alkoxy($C_{1-4}$)alkyl;
or an agrochemically acceptable salt or an N-oxide thereof.

In the compounds of the formula I, each alkyl moiety either alone or as part of a larger group is a $C_{1-4}$- or $C_{1-6}$-straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups have a preferred chain length of from 1 to 4 carbon atoms and are, for example, methoxy, ethoxy, propoxy, i-propoxy, n-butoxy, isobutoxy, sec-butoxy or tert-butoxy. Such groups can be part of a larger group such as alkoxyalkyl and alkoxyalkoxyalkyl, for example, methoxymethyl, methoxyethyl, ethoxymethyl, ethoxyethyl, n-propoxymethyl, n-propoxyethyl, isopropoxymethyl, methoxymethoxymethyl, methoxyethoxymethyl, ethoxymethoxymethyl and ethoxyethoxyethyl.

Halogen is generally fluorine, chlorine, bromine or iodine. This also applies, correspondingly, to halogen in combination with other meanings, such as haloalkyl or haloalkenyl.

Haloalkyl groups preferably have a chain length of from 1 to 4 or 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The preferred alkenyl and alkynyl radicals having 2 to 6 or 3 to 6 carbon atoms can be straight or branched and can contain more than 1 double or triple bond. Examples are vinyl, (E)- or (Z)-propenyl, 2-methyl-propenyl, allyl, 3-methyl-but-2-enyl, ethynyl, prop-1-ynyl, propargyl, butenyl, butynyl, pentenyl and pentynyl.

The cycloalkyl and cycloalkylalkyl groups preferably have from 3 to 6 ring carbon atoms, for example cyclopropyl, cyclobutyl, cyclopentyl and cyclohexyl.

Phenyl, also as part of a substituent such as benzyl, may be substituted, preferably by $C_{1-6}$alkyl, $C_{1-6}$haloalkyl, $C_{1-6}$alkoxy, halogen, nitro or cyano groups. In this case, the substituents can be in ortho, meta and/or para position. The preferred substituent positions are the ortho and para positions relative to the ring attachment point.

The latentiating groups G (i.e. groups which are metabolizable in a plant; in an insect, acarine, mollusc and/or nematode pest; and/or in the soil) are selected to allow its removal by one or a combination of biochemical, chemical or physical processes to afford compounds of formula I where G is hydrogen before, during or following application to the treated area or plants. Examples of these processes include enzymatic cleavage, chemical hydrolysis and photoloysis. Compounds bearing such groups G may offer certain advantages, such as improved penetration of the cuticula of the plants treated, increased tolerance of crops, improved compatibility or stability in formulated mixtures containing other insecticides, herbicide safeners, plant growth regulators, herbicides or fungicides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$ wherein $X^a$, $X^b$, $X^c$, $X^d$, $X^e$ and $X^f$ are independently of each other oxygen or sulfur;
$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro; or heteroaryl or heteroaryl substituted by $C_1$-$C_3$alkyl, $C_{1-3}$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_3$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_3$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$akylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —$C(X^a)$—$R^a$ or —$C(X^b)$—$X^c$—$R^b$, and the meanings of $X^a$, $R^a$, $X^b$, $X^c$ and $R^b$ are as defined above. Preferably, $X^a$, $X^b$ and $X^c$ are oxygen and $R^a$ and $R^b$ are $C_{1-4}$alkyl.

It is also preferred that G is hydrogen, an alkali metal or alkaline earth metal (for instance: lithium, sodium, potassium, beryllium, magnesium, calcium) or an ammonium or sulfonium group, where hydrogen is especially preferred.

More preferably, G is hydrogen, ethoxycarbonyl or pivaloyl.

Depending on the nature of the substituents, compounds of formula I may exist in different isomeric forms. When G is hydrogen, for example, compounds of formula I may exist in different tautomeric forms:

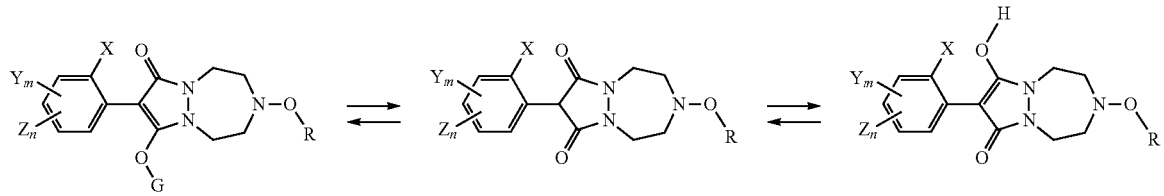

This invention covers all such isomers and tautomers and mixtures thereof in all proportions. Also, when substituents contain double bonds, cis- and trans-isomers can exist. These isomers, too, are within the scope of the claimed compounds of the formula I.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula [N($R_a R_b R_c R_d$)]OH, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e R_f R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The preferred values of R, X, Y, Z, m and n in the compounds of formula I in any combination thereof are set out below, and can be combined with any values of G, in particular with any preferred values of G, as defined above.

Preferably, R is hydrogen, methyl, ethyl, n-propyl, isopropyl, cyanomethyl, trifluoromethyl, 2,2,2-trifluoroethyl, allyl, 3,3-dichloroallyl, propargyl, benzyl, methoxymethyl, ethoxymethyl, methoxyethyl or methoxyethoxymethyl.

More preferably, R is methyl, ethyl or methoxymethyl.

Preferably, X is $C_{1-4}$alkyl, $C_{3-6}$cycloalkyl, $C_{1-4}$alkoxy, $C_{2-6}$alkenyl, $C_{2-6}$alkynyl or halogen.

More preferably, X is methyl, ethyl, isopropyl, n-propyl, cyclopropyl, trifluoromethyl, methoxy, vinyl, ethynyl, fluoro, bromo, iodo or chloro, and in particular methyl, ethyl, methoxy, vinyl, ethynyl, bromo or chloro.

Preferably, Y and Z, independently of each other, are methyl, ethyl, n-propyl, isopropyl, cyclopropyl, trifluoromethyl, methoxy, vinyl, ethynyl, fluoro, bromo, iodo or chloro, phenyl or halo-substituted phenyl, which is in particular fluorophenyl or chlorophenyl and especially 4-chlorophenyl or 4-fluorophenyl.

Preferably, m+n is 1, 2 or 3 and in particular m+n is 1 or 2.

In a preferred group of compounds of the formula (I), R is methyl, X is methyl, ethyl, methoxy, vinyl, ethynyl, bromo or chloro, Y and Z, independently of each other, are methyl, ethyl, methoxy, vinyl, ethynyl, bromo, chloro, phenyl, 4-fluorophenyl or 4-chlorophenyl, G is hydrogen, ethoxycarbonyl or pivaloyl and m+n is 1 or 2.

In another preferred group of compounds of the formula (I), X is different from phenyl or phenyl substituted by $C_{1-4}$alkyl, $C_{1-4}$haloalkyl, halogen or cyano; and Y and Z are different from phenyl or phenyl substituted by $C_{1-4}$alkyl, $C_{1-4}$haloalkyl, halogen or cyano, when they occupy the ortho-position of the phenyl substituent to which they are attached.

In another group of compounds of formula (I), if Y is a phenyl substituent on positions 4 or 5 of the phenyl ring, then m is preferably 1, n is preferably 0 and X is preferably a methyl or ethyl.

The compounds of the invention may be made by a variety of methods. For example, the compounds of formula I, wherein the substituents have the meanings assigned to them above, can be prepared by means of processes known per se, e.g. by treating compounds of formula II, or salts thereof, with an alkylating, acylating, phosphorylating or sulfonylating agent G-Q in the presence of at least one equivalent of a base, where G is the alkyl, acyl, phosphoryl or sulfonyl group to be incorporated and Q is a nucleofuge:

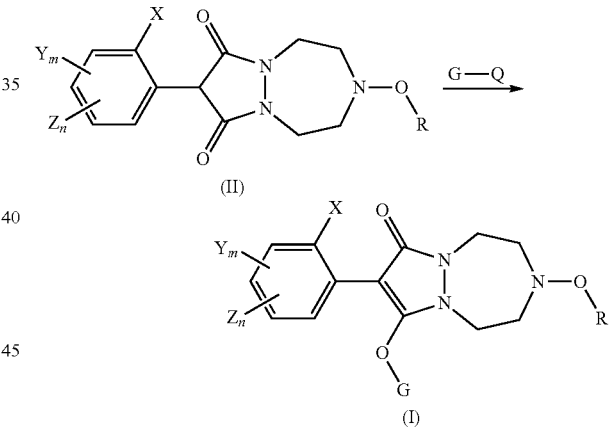

Compounds of formula I, in which X, Y, Z, m, n and R are as defined above and wherein G is a latentiating group of the formula —C($X^a$)—$R^a$, C($X^b$)—$X^c$—$R^b$ or —C($X^d$)—N$R^c R^d$ may be prepared by procedures known in the art, described for example in WO 99/47525. Typically, compounds of formula II, in which X, Y, Z, m, n and R are as defined above, are treated with an acylating agent such as an acid halide (especially acid chloride), acid anhydride, haloformate (especially chloroformate), halothioformate (especially chlorothioformate), isocyanate, isothiocycanate, carbamoyl halide (especially carbamoyl chloride) or thiocarbamoyl halide (especially thiocarbamoyl chloride) in the presence of at least one equivalent of a suitable base, optionally in the presence of a suitable solvent. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases, where the acylating agent is a carboxylic acid, acylation is preferably effected in the presence of a coupling agent such as 2-chloro-1-methylpyridinium iodide, N,N'-dicyclohexycarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane and acetonitrile.

Compounds of formula I, in which X, Y, Z, m, n and R are as defined above and wherein G is a latentiating group of the formula $C(X^b)$—$X^c$—$R^b$ or —$C(X^d)$—$NR^cR^d$, may be also be prepared by treating compounds of formula II, in which X, Y, Z, m, n and R are as defined above, with phosgene or a phosgene equivalent, optionally in the presence of a solvent such as toluene or ethyl acetate, and a base and reacting the resultant chloroformate, or equivalent, with an alcohol, thiol or amine under known conditions, as described, for example, in U.S. Pat. Nos. 6,774,133, 6,555,567 and 6,479,489.

Compounds of formula I, in which X, Y, Z, m, n and R are as defined above and wherein G is a latentiating group of the formula —$P(X^e)R^fR^g$, may be prepared from compounds of formula II, in which X, Y, Z, m, n and R are as defined above, using procedures described, for example, in U.S. Pat. Nos. 6,774,133, 6,555,567 and 6,479,489.

Compounds of formula I, in which X, Y, Z, m, n and R are as defined above and wherein G is a latentiating group of the formula —$SO_2R^e$, may be prepared by reaction of compounds of formula II, in which X, Y, Z, m, n and R are as defined above, with an alkyl or aryl sulfonyl halide, preferably in the presence of at least one equivalent of base.

Compounds of formula I, in which X, Y, Z, m, n and R are as defined above and wherein G is $C_1$-$C_6$alkyl, $C_2$-$C_6$alkenyl, $C_3$-$C_6$alkynyl or a latentiating group of the formula $CH_2$—$X^f$—$R^h$, may be prepared by treatment of a compound of formula II, in which X, Y, Z, m, n and R are as defined above, with a compound of formula G-Y" wherein Y" is a halogen (especially bromine or iodine), sulfonate (especially mesylate or tosylate) or a sulfate preferably in the presence of a base, under known conditions.

Compounds of formula III, or salts thereof, in which X, Y, Z, m, n and G are as defined above,

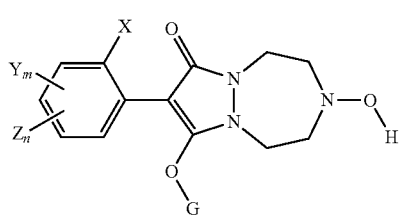

(III)

can be obtained by catalytic hydrogenation of compounds of formula I, in which X, Y, Z, m, n and G are as defined above and in which R is represented by a benzyl group.

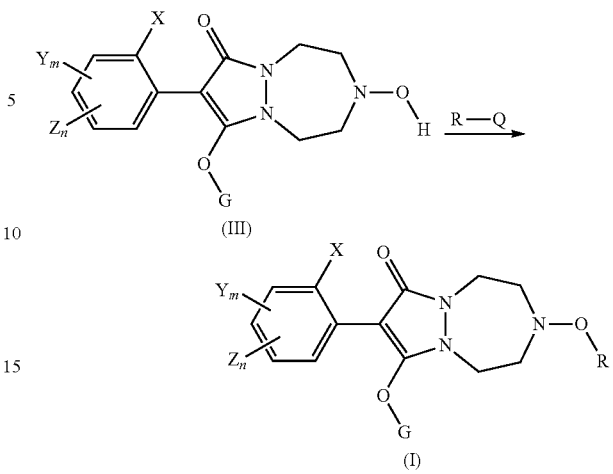

Compounds of formula I, in which X, Y, Z, m, n, R and G are as defined above, can be obtained by treating compounds of formula III, in which X, Y, Z, m, n and G are as defined above, with an alkylating agent R-Q, wherein R represents the alkyl group to be incorporated and Q represents a nucleofuge, in the presence of at least one equivalent of a base, and optionally in the presence of a suitable solvent.

Compounds of formula II, wherein X, Y, Z, m, n and R are as defined above, may be prepared via the cyclisation of compounds of formula IV,

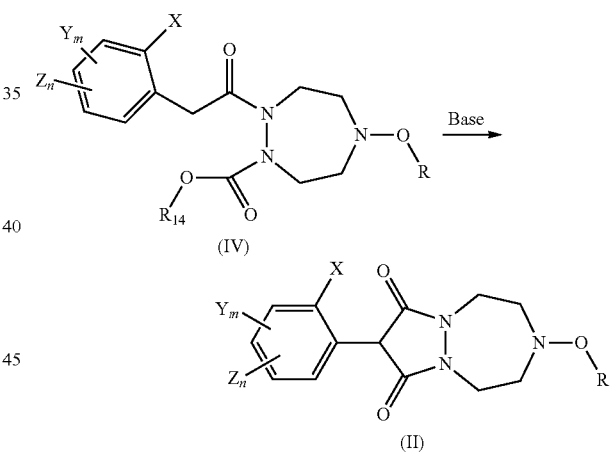

or salts thereof, wherein $R_{14}$ is $C_{1-6}$alkyl, $C_{1-6}$haloalkyl, $C_{2-6}$alkenyl, phenyl or benzyl, and in which phenyl or the phenyl ring of the benzyl group may be substituted by $C_{1-4}$alkyl, halogen, $C_{1-4}$haloalkyl, $C_{1-4}$alkoxy or by nitro, preferably in the presence of base, and optionally in the presence of a suitable solvent, in analogy to known methods described, for example, in WO 09/049851. X, Y, Z, m, n and R are as defined above. Examples of suitable bases include metal hydrides or metal alkoxides, such as sodium hydride, sodium methoxide, sodium or potassium tert-butoxide. Examples of suitable solvents include for example toluene, xylene, ethers such as tetrahydrofuran or N,N-dimethylformamide.

Compounds of formula IV, which are novel and thus constitute another subject of the invention, and in which X, Y, Z, m, n, R and $R_{14}$ are as defined above, may be prepared by reacting oxy triazepane derivatives of formula V, wherein R and $R_{14}$ are as defined above,

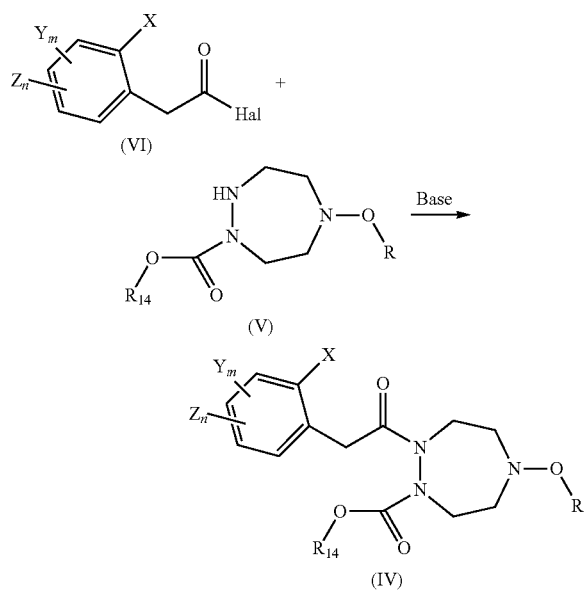

or salts thereof, with phenylacetyl halides of formula VI, wherein X, Y, Z, m and n are as defined above, and wherein Hal is fluorine, chlorine or bromine (preferably chlorine), preferably in the presence of base in a suitable solvent, in analogy to known methods described, for example, in WO 09/049851. The base may be inorganic such as an alkali metal carbonate or hydroxide or a metal hydride, or an organic base such as a tertiary amine or metal alkoxide. Examples of suitable inorganic bases include sodium carbonate, sodium or potassium hydroxide, sodium hydride, and suitable organic bases include trialkylamines such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. The reaction may be performed optionally in presence of an acylation catalyst, such as for example 4-dimethylaminopyridine.

Phenylacetyl halides of formula VI, wherein Hal is fluorine, chlorine or bromine (preferably chlorine) and in which X, Y, Z, m and n are as defined above, are known compounds or can be prepared by known methods, described for example in WO 09/049851.

Oxytriazepane derivatives of the formula V, which are novel and thus constitute another subject of the invention, and wherein R and $R_{14}$ are as defined above,

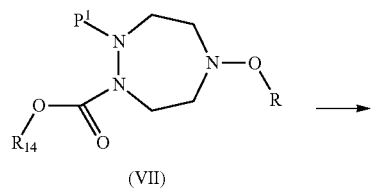

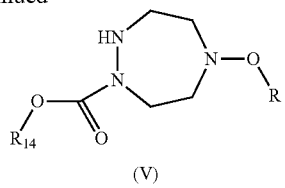

may be prepared from precursor compounds of the formula VII, or salts thereof, in which R and $R_{14}$ are as defined above, and wherein $P^1$ is formyl, $C_{1-6}$alkylcarbonyl (preferably such as acetyl and pivaloyl), $C_{1-6}$cycloalkylcarbonyl, $C_{1-6}$haloalkylcarbonyl (preferably such as trifluoroacetyl), $C_{2-6}$alkenylcarbonyl, $C_{2-6}$alkenyloxycarbonyl, $C_{1-6}$alkoxycarbonyl (preferably such as methoxycarbonyl, ethoxycarbonyl, and t-butoxycarbonyl), $C_{1-6}$haloalkoxycarbonyl (preferably such as trichloroethoxycarbonyl), optionally substituted arylcarbonyl (preferably such as benzoyl), optionally substituted aryloxycarbonyl (preferably such as phenyloxycarbonyl), optionally substituted aryl($C_{1-6}$)alkoxycarbonyl (preferably such a benzyloxycarbonyl, and p-nitrobenzyloxycarbonyl), carbamoyl (preferably such as N.N-dimethyl carbamoyl and N.N-diethyl carbamoyl) or a removable amino protective group. In the particular case where $P^1$ is identical to the fragment —C(O)O$R_{14}$ (symmetrically protected hydrazine derivatives VII), wherein $R_{14}$ is as defined above, even preferably wherein $R_{14}$ is methyl or ethyl, mono deprotection may be achieved, for example, under basic saponification conditions in analogy to P. Baranger, J. Levisalles, Bulletin de la Societe Chimique de France (1957), 704-8. In situations where compounds of the formula VII form orthogonally (differentially) protected hydrazine derivatives, the formation of derivatives of the formula V may benefit from reaction conditions selectively deprotecting the group $P^1$ and leaving the fragment —C(O)O$R_{14}$ unaffected. Such a particular situation is preferred with $P^1$ representing t-butoxycarbonyl (known as the BOC group) or benzyloxycarbonyl (carboxybenzyl, known as the Cbz or Z group). Derivatives of the formula V may be prepared from compounds of the formula VII, wherein $P^1$ is t-butoxycarbonyl, by treatment with strong acids (e.g. trifluoroacetic acid, hydrogen chloride, hydrogen bromide) in solvents like dichloromethane, diethyl ether, tetrahydrofuran, ethyl acetate or dioxane as described in, for example, Bioorganic & Medicinal Chemistry 17 (2009) 4241-4256; or Tetrahedron 65 (2009) 9961-9966; or Heterocycles 78 (2009) 2755-2768. Hydrogen chloride may also be generated in situ by using acetyl chloride in methanol (forming anhydrous HCl in methanol) or thionyl chloride in methanol. Derivatives of the formula V may be prepared from compounds of the formula VII, wherein $P^1$ is benzyloxycarbonyl, by hydrogenolysis (catalytic hydrogenation) in solvents like methanol, ethanol or ethyl acetate, optionally in presence of water or base, as described in, for example, Bioorganic & Medicinal Chemistry 10 (2002) 953-961; or Journal of Heterocyclic chemistry 38 (2001) 613-616.

The compounds VII and V can be reacted and/or isolated as free bases or as salts (e.g. a hydrohalide salt, more specifically a hydrochloride or hydrobromide salt, or any other equivalent salt).

Compounds of the formula VII, wherein R, $R_{14}$ and $P^1$ are as defined above, may be prepared by cyclocondensation of compounds of the formula VIII, or salts thereof, wherein R is as defined above, and in which $LG^1$ and $LG^2$ independently of each other represent a leaving group such as a halogen (preferably chlorine, bromine or iodine; even more preferably chlorine) or a sulfonate —OSO$_2$R$^{su}$, wherein R$^{su}$ is C$_{1-6}$alkyl, C$_{1-6}$haloalkyl, phenyl, C$_{1-6}$alkylphenyl or halophenyl (preferably mesylate [R$^{su}$=CH$_3$], tosylate [R$^{su}$=p-tolyl] or trifluoromethanesulfonate [triflate, R$^{su}$=CF$_3$]; even more preferably mesylate),

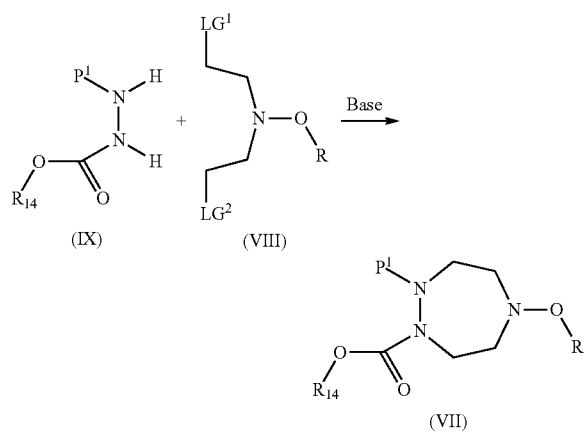

with symmetrically or orthogonally protected hydrazines of the formula IX, wherein P$^1$ and R$_{14}$ are as defined above, preferably in the presence of base in a suitable solvent. The base may be inorganic such as an alkali metal carbonate or hydroxide or a metal hydride, or an organic base such as a tertiary amine or metal alkoxide. Examples of suitable inorganic bases include sodium or potassium carbonate, sodium or potassium hydroxide, sodium hydride, and suitable organic bases include amine bases such as 1,4-diazobicyclo[2.2.2]octane and 1,8-diazabicyclo[5.4.0]undec-7-ene, or sodium methoxide, sodium ethoxide, or potassium t-butoxide. Preferred bases include potassium carbonate, sodium or potassium hydroxide and sodium hydride. Suitable solvents for this reaction are selected to be compatible with the reagents and include ethers or toluene, and polar organic solvents such as dimethyl sulfoxide, N,N-dimethylformamide, N,N-dimethylacetamide and acetonitrile, and alcohols such as methanol, ethanol and t-butanol. Typical condensation reaction conditions may be applied in analogy to Bioorganic & Medicinal Chemistry 17 (2009) 4241-4256; or Chem. Pharm. Bull. 58 (2010) 1001-1002. Improvements in terms of yield for this step may be achieved, for example, by the addition of potassium or sodium iodide, quaternary ammonium salts (e.g. tetrabutyl ammonium iodide) or a crown ether (e.g. 18-crown-6).

A biphasic system, involving aqueous concentrated sodium or potassium hydroxide (25-50%) and an inert solvent such as toluene, dichloromethane or 1,2-dichloroethane, may be used alternatively for the N,N'-bis alkylation of compounds of the formula IX under phase transfer conditions, in analogy, for example, to J. Fluorine Chem 130 (2009) 1001-1010; or Tetrahedron 65 (2009) 9961-9966; or J. Heterocyclic Chem. 38 (2001) 613-616. Ammonium halides, such as tetraethyl- and tetrabutyl ammonium chloride, bromide or iodide, or benzyltriethyl ammonium chloride, bromide or iodide, or aliquats [see C. M. Starks, J. Amer. Chem. 93, 195 (1971)] are typically used as phase transfer catalysts.

Symmetrically or orthogonally protected hydrazines of the formula IX, wherein P$^1$ and R$_{14}$ are as defined above, are known compounds or can be prepared by known methods. Tert-butyl methyl hydrazinedicarboxylate for example is described in Org. Lett. 12 (2010) 2028-2031; and tert-butyl ethyl hydrazinedicarboxylate is described in Tetrahedron 65 (2009) 9961-9966. Di-tert-butyl hydrazine-1,2-dicarboxylate for example is further described in Tetrahedron 64 (2008) 6788-6793.

Compounds of the formula VIII, wherein R is as defined above, and in which LG$^1$ and LG$^2$ independently of each other represent a leaving group such as a halogen (preferably chlorine, bromine or iodine; even more preferably chlorine), are known compounds or can be prepared by known methods. N,N-Bis-(2-chloro-ethyl)-O-methyl-hydroxylamine for example is described in E. R. H. Jones, W. Wilson, J. Chem. Soc. 547-552 (1949).

Compounds of the formula VIII, wherein R is as defined above, and in which LG$^1$ and LG$^2$ independently of each other represent a leaving group such as sulfonate —OSO$_2$R$^{su}$, wherein R$^{su}$ is C$_{1-6}$alkyl, C$_{1-6}$haloalkyl, phenyl, C$_{1-6}$alkylphenyl or halophenyl (preferably mesylate [R$^{su}$=CH$_3$], tosylate [R$^{su}$=p-tolyl] or trifluoromethanesulfonate [triflate, R$^{su}$=CF$_3$]; even more preferably mesylate), may be prepared by treatment of a bis-alcohol of the formula X,

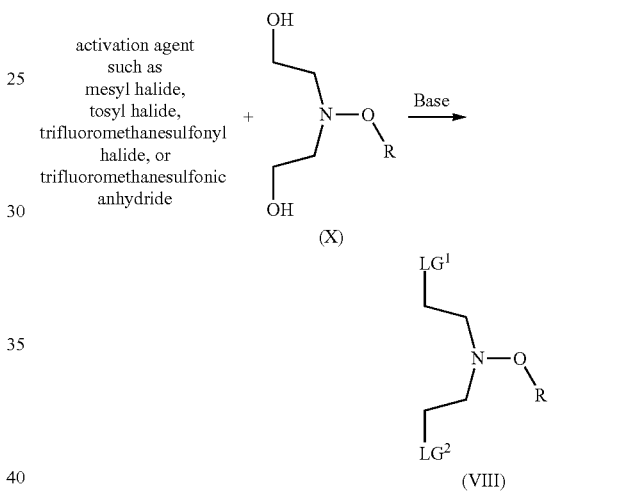

LG$^1$ and/or LG$^2$ is OSO$_2$CH$_3$, OSO$_2$(4-CH$_3$—C$_6$H$_4$), OSO$_2$CF$_3$ or salts thereof, with an activation agent (at least two equivalents) such as a mesyl halide (e.g. methanesulfonyl chloride), a tosyl halide (e.g. p-toluenenesulfonyl chloride), a trifluoromethanesulfonyl halide (e.g. trifluoromethanesulfonyl chloride) or agents such as trifluoromethanesulfonic anhydride or N-phenylbis(trifluoromethanesulfonimide [N-phenyltriflimide], in presence of a base (inorganic or organic), such as, for example, potassium carbonate, triethylamine, diisopropylethylamine or pyridine, in solvents such as, for example, dichloromethane, ethers such as tetrahydrofuran, ethyl acetate, acetonitrile or N, N-dimethylformamide.

Compounds of the formula X, or salts thereof, wherein R is as defined above, are known compounds or can be prepared by known methods. 2-[(2-Hydroxy-ethyl)-methoxy-amino]-ethanol for example is described in N. Sikder, A. K. Sikder, Polish J. Chem. 74, 1697-1706 (2000) and E. R. H. Jones, W. Wilson, J. Chem. Soc. 547-552 (1949); or 2-[ethoxy-(2-hydroxy-ethyl)-amino]-ethanol is described in L. W. Jones, G. R. Burns, J. Am. Chem. Soc. 47, 2966-2973 (1925).

Alternatively, compounds of formula IV, wherein X, Y, Z, m, n, R and R$_{14}$ are as defined above, may also be prepared by cyclocondensation of compounds of the formula VIII, wherein R, LG$^1$ and LG$^2$ are as defined above,

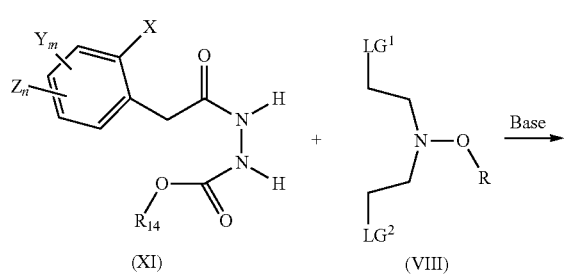

(XI) + (VIII) →Base→

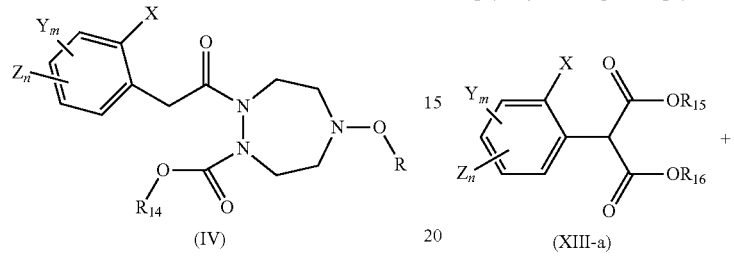

(IV)

or salts thereof, with N,N'-differentially functionalized hydrazines of the formula XI, wherein X, Y, Z, m, n and $R_{14}$ are as defined above, preferably in the presence of base in a suitable solvent. The choices of base and solvent for this transformation are analogous to the conditions described above for the conversion of compounds of the formula IX and VIII into compounds of the formula VII.

Compounds of formula XI, wherein X, Y, Z, m, n and $R_{14}$ are as defined above, may be prepared by reacting hydrazine derivatives of formula XII, wherein $R_{14}$ is as defined above,

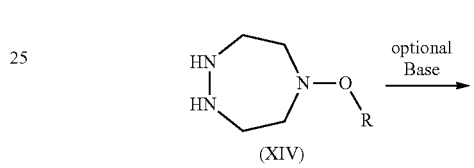

(VI) + (XII) →Base→

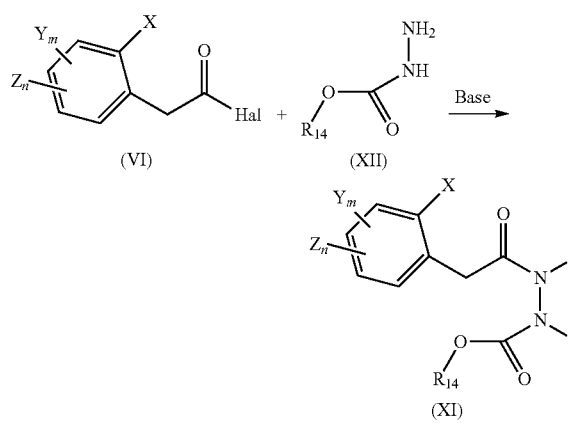

(XI)

or salts thereof, with phenylacetyl halides of formula VI, wherein X, Y, Z, m and n are as defined above, and wherein Hal is fluorine, chlorine or bromine (preferably chlorine), preferably in the presence of base in a suitable solvent by known methods. The choices of base and solvent for this transformation are analogous to the conditions described above for the conversion of compounds of the formula VI and V into compounds of the formula IV. The reaction may be performed optionally in presence of an acylation catalyst, such as for example 4-dimethylaminopyridine.

Hydrazine derivatives of formula XII, wherein $R_{14}$ is as defined above, or salts thereof, are known compounds, in instances commercially available, or can be prepared by known methods. Hydrazinecarboxylic acid ethyl ester (ethyl carbazate) for example is described in Organic Syntheses 51 (1971) 121-127; and hydrazinecarboxylic acid methyl ester (methyl carbazate) is described in Berichte der Deutschen Chemischen Gesellschaft 44 (1912) 3018-27.

Alternatively, compounds of formula II, wherein X, Y, Z, m, n and R are as defined above, may also be prepared via the condensation/cyclisation of compounds of formula XIII-a, wherein X, Y, Z, m and n are as defined above and wherein $R_{15}$ and $R_{16}$ independently of each other are $C_{1-6}$alkyl, $C_{1-6}$haloalkyl, $C_{2-6}$alkenyl, phenyl or benzyl, and in which phenyl or the phenyl ring of the benzyl group may be substituted by $C_{1-4}$alkyl, halogen, $C_{1-4}$haloalkyl, $C_{1-4}$alkoxy or by nitro,

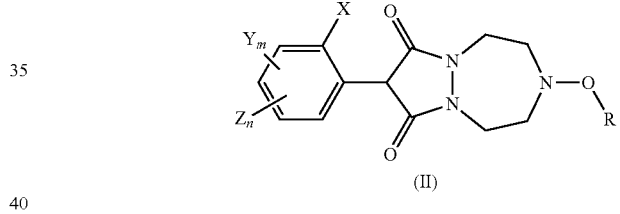

(XIII-a) +

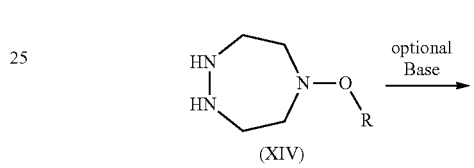

(XIV) →optional Base→

(II)

with hydrazine derivatives of the formula XIV, or salts thereof, wherein R is as defined above, in an inert organic solvent, such as toluene, xylene (all isomers), 1,2-dichloroethane or chlorobenzene, optionally in the presence of a base, preferably nitrogen bases such as triethylamine and pyridine, and optionally under inert atmosphere (e.g. under nitrogen or argon atmosphere) in analogy to known methods described, for example, in WO 99/47525 or WO 01/17973.

Compounds of formula XIII-a, wherein X, Y, Z, m and n are as defined above and wherein $R_{15}$ and $R_{16}$ independently of each other are $C_{1-6}$alkyl, $C_{1-6}$haloalkyl, $C_{2-6}$alkenyl, phenyl or benzyl, and in which phenyl or the phenyl ring of the benzyl group may be substituted by $C_{1-4}$alkyl, halogen, $C_{1-4}$haloalkyl, $C_{1-4}$alkoxy or by nitro, are known compounds or can be prepared by known methods in analogy, for example, to WO 99/47525 or WO 01/17973.

Alternatively, compounds of formula II, wherein X, Y, Z, m, n and R are as defined above, may also be prepared via the condensation/cyclisation of compounds of formula XIII-b, wherein X, Y, Z, m and n are as defined above and wherein $R_{17}$, $R_{18}$, $R_{19}$ and $R_{20}$ independently of each other are hydrogen, $C_{1-6}$alkyl, $C_{1-6}$haloalkyl, $C_{2-6}$alkenyl, phenyl or benzyl, and in which phenyl or the phenyl ring of the benzyl group may be substituted by $C_{1-4}$alkyl, halogen, $C_{1-4}$haloalkyl, $C_{1-4}$alkoxy or by nitro,

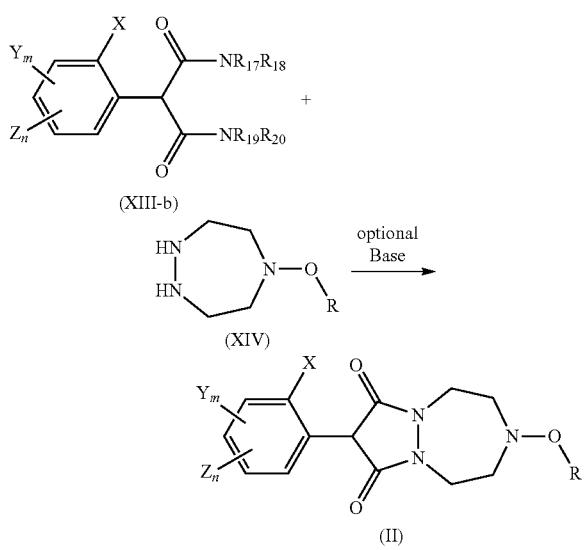

with hydrazine derivatives of the formula XIV, or salts thereof, wherein R is as defined above, in an inert organic solvent, such as toluene, xylene (all isomers), 1,2-dichloroethane or chlorobenzene, optionally in the presence of a base, preferably nitrogen bases such as triethylamine and pyridine, and optionally under inert atmosphere (e.g. under nitrogen or argon atmosphere) in analogy to known methods described, for example, in WO 00/78881.

Compounds of formula XIII-b, wherein X, Y, Z, m and n are as defined above and wherein $R_{17}$, $R_{18}$, $R_{19}$ and $R_{20}$ independently of each other are hydrogen, $C_{1-6}$alkyl, $C_{2-6}$alkenyl, phenyl or benzyl, and in which phenyl or the phenyl ring of the benzyl group may be substituted by $C_{1-4}$alkyl, halogen, $C_{1-4}$haloalkyl, $C_{1-4}$alkoxy or by nitro, are known compounds or can be prepared by known methods in analogy, for example, to WO 00/78881.

Hydrazine derivatives of formula XIV, which are novel and thus constitute another subject of the invention, and wherein R is as defined above,

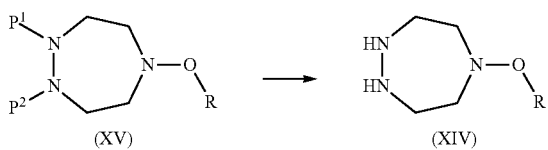

may be prepared from precursor compounds of the formula XV, or salts thereof, wherein $P^1$ and $P^2$ independently of each other are formyl, $C_{1-6}$alkylcarbonyl (preferably such as acetyl and pivaloyl), $C_{1-6}$cycloalkylcarbonyl, $C_{1-6}$haloalkylcarbonyl (preferably such as trifluoroacetyl), $C_{2-6}$alkenylcarbonyl, $C_{2-6}$alkenyloxycarbonyl, $C_{1-6}$alkoxycarbonyl (preferably such as methoxycarbonyl, ethoxycarbonyl, and t-butoxycarbonyl), $C_{1-6}$haloalkoxycarbonyl (preferably such as trichloroethoxycarbonyl), optionally substituted arylcarbonyl (preferably such as benzoyl), optionally substituted aryloxycarbonyl (preferably such as phenyloxycarbonyl), optionally substituted aryl($C_{1-6}$)alkoxycarbonyl (preferably such a benzyloxycarbonyl, and p-nitrobenzyloxycarbonyl), carbamoyl (preferably such as N.N-dimethyl carbamoyl and N.N-diethyl carbamoyl) or a removable amino protective group. 'Amino protecting groups' is referring to any amino protecting group known to a person skilled in the art, as described for example in P. G. M. Wuts, T. W. Green, Greene's Protective Groups in Organic Synthesis, Fourth Edition, John Wiley & Sons, 2007. This term is preferably referring to formyl, $C_{1-6}$alkylcarbonyl (e.g. acetyl, pivaloyl), $C_{1-6}$haloalkylcarbonyl (e.g. trifluoroacetyl), $C_{1-6}$alkoxycarbonyl (e.g. methoxycarbonyl, ethoxycarbonyl or t-butoxycarbonyl [known as the BOC group]), $C_{1-6}$haloalkoxycarbonyl (e.g. trichloroethoxycarbonyl), optionally substituted arylcarbonyl (e.g. benzoyl), optionally substituted aryloxycarbonyl (e.g. phenyloxycarbonyl), optionally substituted aryl ($C_{1-6}$)alkylcarbonyl (e.g. benzyloxycarbonyl [equivalent to carboxybenzyl], known as the Cbz or Z group; or p-nitrobenzyloxycarbonyl), carbamoyl (e.g. N.N-dimethyl carbamoyl and N.N-diethyl carbamoyl).

It is usually preferred that $P^1$ is identical to $P^2$ (symmetrically protected hydrazine derivatives XV). The removal of the groups $P^1$ and $P^2$ (deprotection) may be achieved, for example, by reacting a compound of the formula XV in the presence of a base or an acid in an inert solvent, as described for example in WO 03/051853 and WO 06/045587. In the preferred situation where $P^1$ and/or $P^2$ represent acetyl or t-butoxycarbonyl (known as the BOC group), derivatives of the formula XIV may be prepared from compounds of the formula XV, by treatment with strong acids (e.g. trifluoroacetic acid, hydrogen chloride, hydrogen bromide) in solvents like dichloromethane, diethyl ether, tetrahydrofuran, ethyl acetate or dioxane as described in, for example, Bioorganic & Medicinal Chemistry 17 (2009) 4241-4256; or Tetrahedron 65 (2009) 9961-9966; or Heterocycles 78 (2009) 2755-2768. Hydrogen chloride may also be generated in situ by using acetyl chloride in methanol (forming anhydrous HCl in methanol, as described for example in WO 01/17973) or thionyl chloride in methanol. In the preferred situation where $P^1$ and $P^2$ represent benzyloxy-carbonyl (carboxybenzyl, known as the Cbz or Z group), derivatives of the formula XIV may be prepared from compounds of the formula XV, by hydrogenolysis (catalytic hydrogenation) in solvents like methanol, ethanol or ethyl acetate, optionally in presence of water or base, in analogy to, for example, Bioorganic & Medicinal Chemistry 10 (2002) 953-961; or Journal of Heterocyclic chemistry 38 (2001) 613-616.

The compounds XIV and XV can be reacted and/or isolated as free bases or as salts (e.g. a hydrohalide salt, more specifically a hydrochloride or hydrobromide salt, or any other equivalent salt).

Compounds of the formula XV, which are novel and thus constitute another subject of the invention, and wherein $P^1$, $P^2$ and R are as defined above, may be prepared by cyclocondensation of compounds of the formula VIII, wherein R, $LG^1$ and $LG^2$ are as defined above,

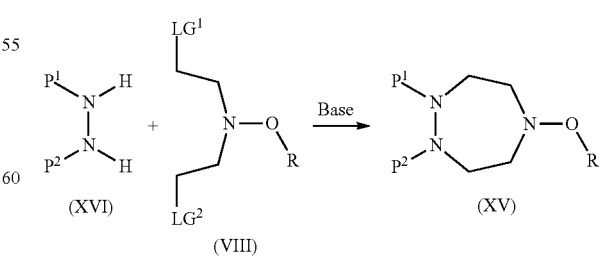

or salts thereof, with symmetrically or orthogonally protected hydrazines of the formula XVI, wherein $P^1$ and $P^2$ are the same or different, and are as defined above, preferably in the presence of base in a suitable solvent. The choices of base and solvent for this transformation are analogous to the conditions described above for the conversion of compounds of the formula IX and VIII into compounds of the formula VII. Typical reaction conditions may be further applied in analogy to WO 99/47525, WO 01/17973, WO 03/051853 and WO 06/045587.

Symmetrically or orthogonally protected hydrazines of the formula XVI, wherein $P^1$ and $P^2$ are the same or different, and are as defined above, are known compounds or can be prepared by known methods as described above for the preparation of compounds of the formula VII.

Alternatively, compounds of formula II, wherein X, Y, Z, m, n and R are as defined above, may also be prepared via the condensation/cyclisation of compounds of formula XVII, wherein Hal is fluorine, chlorine or bromine (preferably chlorine; then defining a substituted chlorocarbonylketene) and in which X, Y, Z, m and n are as defined above,

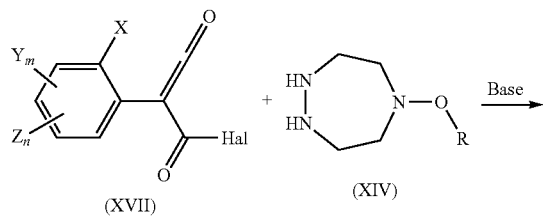

(XVII)        (XIV)

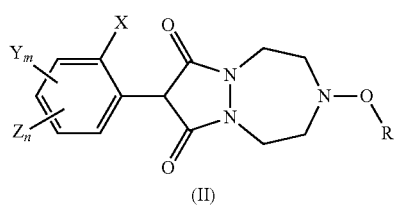

(II)

with hydrazine derivatives of the formula XIV, or salts thereof, wherein R is as defined above, in an inert organic solvent, such as toluene, xylene (all isomers), ethers or dichloromethane, in the presence of a base as hydrogen halide scavenger (e.g. triethylamine or pyridine), and optionally under inert atmosphere, in analogy to known methods described, for example, in EP 508126 (1992).

Compounds of formula XVII, wherein Hal is fluorine, chlorine or bromine (preferably chlorine) and in which X, Y, Z, m and n are as defined above, are known compounds or can be prepared by known methods in analogy, for example, to S. Nakanishi, K. Butler, Org. Prep. Proced. Int. 7, 155-158 (1975).

The compounds VIII, X, XII, XIV and XV can be reacted and/or isolated as free bases or as salts (e.g. a hydrohalide salt, more specifically a hydrochloride or hydrobromide salt, or any other equivalent salt).

Compounds of the formula IV, V, XIV and XV, and salts thereof, are novel, have been specifically designed for the synthesis of the compounds of the formula I and as such form a further aspect of the invention. Thus compounds of the formula IV

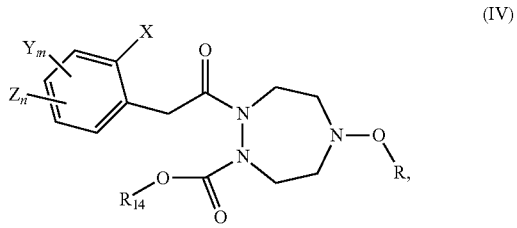

and salts thereof, wherein X, Y, Z, m, n and R have the meanings assigned to them above, and $R_{14}$ is $C_{1-6}$alkyl, $C_{1-6}$haloalkyl, $C_{2-6}$alkenyl, phenyl or benzyl; and compounds of the formula V

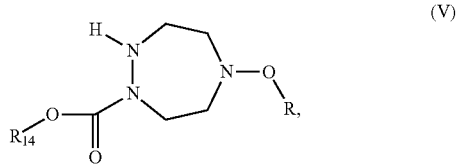

and salts thereof, wherein R has the meanings assigned to it above, and $R_{14}$ is $C_{1-6}$alkyl, $C_{1-6}$haloalkyl, $C_{2-6}$alkenyl, phenyl or benzyl; and compounds of the formula XIV

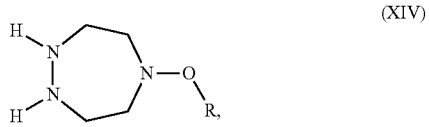

and salts thereof, wherein R has the meanings assigned to it above; and compounds of the formula XV

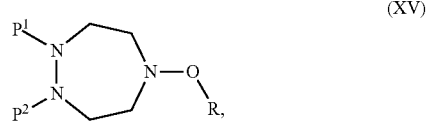

and salts thereof, wherein R has the meanings assigned to it above, and in which $P^1$ and $P^2$ independently of each other are formyl, $C_{1-6}$alkylcarbonyl, $C_{1-6}$cycloalkylcarbonyl, $C_{1-6}$haloalkylcarbonyl, $C_{2-6}$alkenylcarbonyl, $C_{2-6}$alkenyloxycarbonyl, $C_{1-6}$alkoxycarbonyl, $C_{1-6}$haloalkoxycarbonyl, optionally substituted arylcarbonyl, optionally substituted aryloxycarbonyl, optionally substituted aryl($C_{1-6}$)alkoxycarbonyl, carbamoyl or a removable amino protective group are novel.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 16 below can be prepared according to the methods described above. The examples which follow are intended to illustrate the invention and show preferred compounds of formula I.

TABLE 1

This table discloses the 178 compounds T1.001 to T1.178 of the formula Ia:

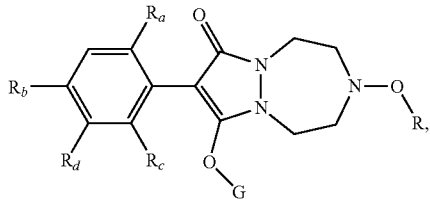

(Ia)

wherein R is CH₃, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | CH₃ | H | H | H |
| T1.004 | CH₂CH₃ | H | H | H |
| T1.005 | OCH₃ | H | H | H |
| T1.006 | Br | Cl | H | H |
| T1.007 | Cl | Br | H | H |
| T1.008 | Cl | Cl | H | H |
| T1.009 | Cl | CH₃ | H | H |
| T1.010 | CH₃ | Cl | H | H |
| T1.011 | CH₃ | CH₃ | H | H |
| T1.012 | Cl | H | Cl | H |
| T1.013 | Cl | H | CH₃ | H |
| T1.014 | Cl | H | CH₂CH₃ | H |
| T1.015 | Cl | H | OCH₃ | H |
| T1.016 | CH₃ | H | CH₃ | H |
| T1.017 | CH₃ | H | CH₂CH₃ | H |
| T1.018 | CH₃ | H | OCH₃ | H |
| T1.019 | CH₂CH₃ | H | CH₂CH₃ | H |
| T1.020 | CH₂CH₃ | H | OCH₃ | H |
| T1.021 | OCH₃ | H | OCH₃ | H |
| T1.022 | Br | H | H | Cl |
| T1.023 | Br | H | H | CH₃ |
| T1.024 | Br | H | H | 4-Cl—C₆H₄ |
| T1.025 | Cl | H | H | Cl |
| T1.026 | Cl | H | H | CH₃ |
| T1.027 | Cl | H | H | 4-Cl—C₆H₄ |
| T1.028 | CH₃ | H | H | Br |
| T1.029 | CH₃ | H | H | Cl |
| T1.030 | CH₃ | H | H | CH₃ |
| T1.031 | CH₃ | H | H | C₆H₅ |
| T1.032 | CH₃ | H | H | 4-Cl—C₆H₄ |
| T1.033 | CH₂CH₃ | H | H | CH₃ |
| T1.034 | CH₂CH₃ | H | H | 4-Cl—C₆H₄ |
| T1.035 | OCH₃ | H | H | CH₃ |
| T1.036 | OCH₃ | H | H | 4-Cl—C₆H₄ |
| T1.037 | Cl | H | Cl | Br |
| T1.038 | CH₃ | H | CH₃ | Br |
| T1.039 | CH₃ | H | CH₃ | Cl |
| T1.040 | CH₃ | H | CH₃ | 4-Cl—C₆H₄ |
| T1.041 | Br | Cl | H | CH₃ |
| T1.042 | Br | CH₃ | H | CH₃ |
| T1.043 | Cl | Cl | H | Cl |
| T1.044 | Cl | Br | H | CH₃ |
| T1.045 | Cl | Cl | H | CH₃ |
| T1.046 | Cl | CH₃ | H | Cl |
| T1.047 | Cl | CH₃ | H | CH₃ |
| T1.048 | CH₃ | Br | H | CH₃ |
| T1.049 | CH₃ | Cl | H | CH₃ |
| T1.050 | CH₃ | CH₃ | H | CH₃ |
| T1.051 | CH₃ | CH₃ | H | 4-Cl—C₆H₄ |
| T1.052 | Br | Br | CH₃ | H |
| T1.053 | Br | Cl | CH₃ | H |
| T1.054 | Br | CH₃ | Br | H |
| T1.055 | Br | CH₃ | Cl | H |
| T1.056 | Cl | Br | CH₃ | H |
| T1.057 | Cl | Cl | Cl | H |
| T1.058 | Cl | Cl | CH₃ | H |
| T1.059 | Cl | CH₃ | Cl | H |
| T1.060 | Cl | CH₃ | CH₂CH₃ | H |
| T1.061 | Cl | CH₃ | OCH₃ | H |
| T1.062 | Cl | 4-Cl—C₆H₄ | Cl | H |
| T1.063 | Cl | 4-Cl—C₆H₄ | CH₃ | H |
| T1.064 | Cl | 4-Cl—C₆H₄ | CH₂CH₃ | H |
| T1.065 | Cl | 4-Cl—C₆H₄ | OCH₃ | H |
| T1.066 | CH₃ | Br | CH₃ | H |
| T1.067 | CH₃ | Cl | CH₃ | H |
| T1.068 | CH₃ | CH₃ | Br | H |
| T1.069 | CH₃ | CH₃ | Cl | H |
| T1.070 | CH₃ | CH₃ | CH₃ | H |
| T1.071 | CH₃ | CH₃ | CH₂CH₃ | H |
| T1.072 | CH₃ | CH₃ | OCH₃ | H |
| T1.073 | CH₃ | 4-Cl—C₆H₄ | CH₃ | H |
| T1.074 | CH₃ | 4-Cl—C₆H₄ | CH₂CH₃ | H |
| T1.075 | CH₃ | 4-Cl—C₆H₄ | OCH₃ | H |
| T1.076 | CH₂CH₃ | Br | Br | H |
| T1.077 | CH₂CH₃ | Br | Cl | H |
| T1.078 | CH₂CH₃ | Br | CH₃ | H |
| T1.079 | CH₂CH₃ | Br | CH₂CH₃ | H |
| T1.080 | CH₂CH₃ | Br | OCH₃ | H |
| T1.081 | CH₂CH₃ | Cl | Br | H |
| T1.082 | CH₂CH₃ | Cl | Cl | H |
| T1.083 | CH₂CH₃ | Cl | CH₃ | H |
| T1.084 | CH₂CH₃ | Cl | CH₂CH₃ | H |
| T1.085 | CH₂CH₃ | Cl | OCH₃ | H |
| T1.086 | CH₂CH₃ | CH₃ | Br | H |
| T1.087 | CH₂CH₃ | CH₃ | Cl | H |
| T1.088 | CH₂CH₃ | CH₃ | CH₂CH₃ | H |
| T1.089 | CH₂CH₃ | CH₃ | OCH₃ | H |
| T1.090 | CH₂CH₃ | CH₂CH₃ | CH₃ | H |
| T1.091 | CH₂CH₃ | CH₂CH₃ | CH₂CH₃ | H |
| T1.092 | CH₂CH₃ | 4-Cl—C₆H₄ | Br | H |
| T1.093 | CH₂CH₃ | 4-Cl—C₆H₄ | CH₂CH₃ | H |
| T1.094 | CH₂CH₃ | 4-Cl—C₆H₄ | OCH₃ | H |
| T1.095 | OCH₃ | Br | CH₃ | H |
| T1.096 | OCH₃ | Cl | CH₃ | H |
| T1.097 | OCH₃ | CH₃ | Br | H |
| T1.098 | OCH₃ | CH₃ | Cl | H |
| T1.099 | OCH₃ | CH₃ | OCH₃ | H |
| T1.100 | OCH₃ | 4-Cl—C₆H₄ | OCH₃ | H |
| T1.101 | CH₃ | CH₃ | CH₃ | F |
| T1.102 | CH₃ | CH₃ | CH₃ | Cl |
| T1.103 | CH₃ | CH₃ | CH₃ | Br |
| T1.104 | CH₃ | CH₃ | CH₃ | CH₃ |
| T1.105 | CH₃ | CH₃ | CH₃ | 4-Cl—C₆H₄ |
| T1.106 | Cl | CH₃ | CH₃ | CH₃ |
| T1.107 | CH₃ | Cl | CH₃ | CH₃ |
| T1.108 | CH₃ | CH₃ | Cl | CH₃ |
| T1.109 | CH₂CH₃ | CH₃ | CH₃ | CH₃ |
| T1.110 | OCH₃ | CH₃ | CH₃ | CH₃ |
| T1.111 | Cyclo-C3 | CH₃ | CH₃ | CH₃ |
| T1.112 | CH₃ | CH₃ | Cyclo-C3 | H |
| T1.113 | CH₃ | F | H | Br |
| T1.114 | CH₃ | CH₃ | H | Br |
| T1.115 | CH₂CH₃ | CH₃ | H | CH₃ |
| T1.116 | OCH₃ | CH₃ | H | CH₃ |
| T1.117 | Cyclo-C3 | CH₃ | H | CH₃ |
| T1.118 | CH₂CH₃ | Cl | H | CH₃ |
| T1.119 | OCH₃ | Cl | H | CH₃ |
| T1.120 | Cyclo-C3 | Cl | H | CH₃ |

TABLE 1-continued

This table discloses the 178 compounds T1.001 to T1.178 of the formula Ia:

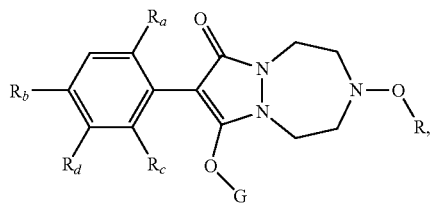

wherein R is $CH_3$, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.121 | Cl | H | $CH_3$ | $CH_3$ |
| T1.122 | $CH_3$ | H | $CH_3$ | $CH_3$ |
| T1.123 | $CH_2CH_3$ | H | $CH_3$ | $CH_3$ |
| T1.124 | $OCH_3$ | H | $CH_3$ | $CH_3$ |
| T1.125 | Cyclo-C3 | H | $CH_3$ | $CH_3$ |
| T1.126 | F | H | Cl | $CH_3$ |
| T1.127 | Cl | H | F | $CH_3$ |
| T1.128 | H | $CH_3$ | $CH_3$ | $CH_3$ |
| T1.129 | Br | $CH_3$ | $CH_3$ | $CH_3$ |
| T1.130 | $CH_3$ | H | Cl | $CH_3$ |
| T1.131 | $CH_3$ | H | Br | $CH_3$ |
| T1.132 | Br | H | $CH_3$ | $CH_3$ |
| T1.133 | $CH_3$ | $CH=CH_2$ | $CH_3$ | H |
| T1.134 | $CH_3$ | $CH_3$ | $CH=CH_2$ | H |
| T1.135 | $CH_3$ | $C\equiv CH$ | $CH_3$ | H |
| T1.136 | $CH_3$ | $CH_3$ | $C\equiv CH$ | H |
| T1.137 | $CH_3$ | I | $CH_3$ | H |
| T1.138 | $CH_3$ | $CH_3$ | I | H |
| T1.139 | $CH_3$ | $CH_3$ | H | I |
| T1.140 | $CH_3$ | $CF_3$ | $CH_3$ | H |
| T1.141 | $CH_3$ | $CH_3$ | $CF_3$ | H |
| T1.142 | $CH_3$ | $CHF_2$ | $CH_3$ | H |
| T1.143 | $CH_3$ | $CH_3$ | $CHF_2$ | H |
| T1.144 | $CH_3$ | Cyclo-C3 | $CH_3$ | H |
| T1.145 | $CH=CH_2$ | $CH_3$ | $CH=CH_2$ | H |
| T1.146 | $C\equiv CH$ | $CH_3$ | $C\equiv CH$ | H |
| T1.147 | Cl | H | H | 4-F—$C_6H_4$ |
| T1.148 | $CH_3$ | H | H | 4-F—$C_6H_4$ |
| T1.149 | $CH_2CH_3$ | H | H | 4-F—$C_6H_4$ |
| T1.150 | $OCH_3$ | H | H | 4-F—$C_6H_4$ |
| T1.151 | $CH_3$ | H | $CH_3$ | 4-F—$C_6H_4$ |
| T1.152 | $CH_3$ | $CH_3$ | H | 4-F—$C_6H_4$ |
| T1.153 | $CH_3$ | $CH_3$ | $CH_3$ | 4-F—$C_6H_4$ |
| T1.154 | $CH_2CH_3$ | H | $CH_2CH_3$ | 4-Cl—$C_6H_4$ |
| T1.155 | $CH_2CH_3$ | H | $CH_2CH_3$ | 4-F—$C_6H_4$ |
| T1.156 | $CH_2CH_3$ | H | $CH_3$ | 4-Cl—$C_6H_4$ |
| T1.157 | $CH_2CH_3$ | H | $CH_3$ | 4-F—$C_6H_4$ |
| T1.158 | $CH_3$ | H | $CH_2CH_3$ | 4-Cl—$C_6H_4$ |
| T1.159 | $CH_3$ | H | $CH_2CH_3$ | 4-F—$C_6H_4$ |
| T1.160 | Cl | H | $CH_3$ | 4-Cl—$C_6H_4$ |
| T1.161 | Cl | H | $CH_3$ | 4-F—$C_6H_4$ |
| T1.162 | $CH_3$ | H | Cl | 4-Cl—$C_6H_4$ |
| T1.163 | $CH_3$ | H | Cl | 4-F—$C_6H_4$ |
| T1.164 | Cl | 4-F—$C_6H_4$ | Cl | H |
| T1.165 | $CH_3$ | 4-F—$C_6H_4$ | $CH_3$ | H |
| T1.166 | $CH_3$ | 4-F—$C_6H_4$ | $CH_2CH_3$ | H |
| T1.167 | $CH_3$ | 4-F—$C_6H_4$ | $OCH_3$ | H |
| T1.168 | $CH_2CH_3$ | 4-F—$C_6H_4$ | $CH_2CH_3$ | H |
| T1.169 | $CH_2CH_3$ | 4-F—$C_6H_4$ | $OCH_3$ | H |
| T1.170 | $OCH_3$ | 4-F—$C_6H_4$ | $OCH_3$ | H |
| T1.171 | Cl | $C_6H_5$ | Cl | H |
| T1.172 | $CH_3$ | $C_6H_5$ | $CH_3$ | H |
| T1.173 | $CH_3$ | $C_6H_5$ | $CH_2CH_3$ | H |
| T1.174 | $CH_3$ | $C_6H_5$ | $OCH_3$ | H |
| T1.175 | $CH_2CH_3$ | $C_6H_5$ | $CH_2CH_3$ | H |
| T1.176 | $CH_2CH_3$ | $C_6H_5$ | $OCH_3$ | H |
| T1.177 | $OCH_3$ | $C_6H_5$ | $OCH_3$ | H |
| T1.178 | $CH_3$ | $CH_3$ | $CH_3$ | $C_6H_5$ |

Cyclo-C3 means cyclopropyl.

Table 2: This table discloses the 178 compounds T2.001 to T2.178 of the formula Ia, wherein R is $CH_2CH_3$, G is hydrogen and $R_a$, $R_b$, $R_c$ and $R_d$ are as defined in Table 1.

Table 3: This table discloses the 178 compounds T3.001 to T3.178 of the formula Ia, wherein R is n-$C_3H_7$, G is hydrogen and $R_a$, $R_b$, $R_c$ and $R_d$ are as defined in Table 1.

Table 4: This table discloses the 178 compounds T4.001 to T4.178 of the formula Ia, wherein R is i-$C_3H_7$, G is hydrogen and $R_a$, $R_b$, $R_c$ and $R_d$ are as defined in Table 1.

Table 5: This table discloses the 178 compounds T5.001 to T5.178 of the formula Ia, wherein R is allyl, G is hydrogen and $R_a$, $R_b$, $R_c$ and $R_d$ are as defined in Table 1.

Table 6: This table discloses the 178 compounds T6.001 to T6.178 of the formula Ia, wherein R is propargyl, G is hydrogen and $R_a$, $R_b$, $R_c$ and $R_d$ are as defined in Table 1.

Table 7: This table discloses the 178 compounds T7.001 to T7.178 of the formula Ia, wherein R is benzyl, G is hydrogen and $R_a$, $R_b$, $R_c$ and $R_d$ are as defined in Table 1.

Table 8: This table discloses the 178 compounds T8.001 to T8.178 of the formula Ia, wherein R is hydrogen, G is hydrogen and $R_a$, $R_b$, $R_c$ and $R_d$ are as defined in Table 1.

Table 9: This table discloses the 178 compounds T9.001 to T9.178 of the formula Ia, wherein R is $CH_2OCH_3$, G is hydrogen and $R_a$, $R_b$, $R_c$ and $R_d$ are as defined in Table 1.

Table 10: This table discloses the 178 compounds T10.001 to T10.178 of the formula Ia, wherein R is $CH_2CH_2OCH_3$, G is hydrogen and $R_a$, $R_b$, $R_c$ and $R_d$ are as defined in Table 1.

Table 11: This table discloses the 178 compounds T11.001 to T11.178 of the formula Ia, wherein R is $CH_2OCH_2CH_3$, G is hydrogen and $R_a$, $R_b$, $R_c$ and $R_d$ are as defined in Table 1.

Table 12: This table discloses the 178 compounds T12.001 to T12.178 of the formula Ia, wherein R is $CH_2OC_2H_4OCH_3$, G is hydrogen and $R_a$, $R_b$, $R_c$ and $R_d$ are as defined in Table 1.

Table 13: This table discloses the 178 compounds T13.001 to T13.178 of the formula Ia, wherein R is $CH_2CF_3$, G is hydrogen and $R_a$, $R_b$, $R_c$ and $R_d$ are as defined in Table 1.

Table 14: This table discloses the 178 compounds T14.001 to T14.178 of the formula Ia, wherein R is $CH_2CN$, G is hydrogen and $R_a$, $R_b$, $R_c$ and $R_d$ are as defined in Table 1.

Table 15: This table discloses the 178 compounds T15.001 to T15.178 of the formula Ia, wherein R is $CH_3$, G is ethoxycarbonyl and $R_a$, $R_b$, $R_c$ and $R_d$ are as defined in Table 1.

Table 16: This table discloses the 178 compounds T16.001 to T16.178 of the formula Ia, wherein R is $CH_3$, G is pivaloyl and $R_a$, $R_b$, $R_c$ and $R_d$ are as defined in Table 1.

In one aspect of the invention, the compounds according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compounds of formula I can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula I include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:
from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp., *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens;* from the order Homoptera, for example,

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp., *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopol-*

*ophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate;* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp., *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; and from the order Thysanura, for example,

*Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or *sorghum*; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus;* toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerant to abiotic stress include those that have enhanced tolerance to drought, high salt, high temperature, chill, frost, or light radiation, for example through expression of NF-YB or other proteins known in the art.

Crops that exhibit enhanced yield or quality include those with improved flowering or fruit ripening properties (such as delayed ripening); modified oil, starch, amino acid, fatty acid, vitamin, phenolic or other content (such as Vistive™ soybean variety); enhanced nutrient utilisation (such as improved nitrogen assimilation); and enhanced quality plant product (such as higher quality cotton fibre).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore provides a method of combating and controlling insects, acarines, nematodes or molluscs which comprises applying an insecticidally, acaricidally, nematicidally or molluscicidally effective amount of a compound of formula I, or a composition containing a compound of formula I, to a pest, a locus of pest, or to a plant susceptible to attack by a pest. The compounds of formula I are preferably used against insects or acarines.

The term "plant" as used herein includes seedlings, bushes and trees.

In another aspect, the compounds according to the invention can be used to control weeds in crops of useful plants. Such crops preferably include especially cereals, in particular wheat and barley, rice, corn, rape, sugarbeet, sugarcane, soybean, cotton, sunflower, peanut and plantation crops.

In this connection, the term "crops" is preferably to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The invention therefore provides a method of controlling grasses and weeds in crops of useful plants, which comprises applying a herbicidally effective amount of a compound of formula I, or of a composition comprising such a compound, to the plants or to the locus thereof.

The invention also relates to pesticidal and herbicidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Preferably, for pesticidal and in particular for insecticidal uses, examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl¬ naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl) phosphate, tris-n-octyl phosphate and tris-butoxyethyl phosphate, where tris-(2-ethylhexyl) phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{13}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

As a rule, the compositions comprise 0.1 to 99%, especially 0.1 to 95%, of active ingredient of the formula I and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Preferred compositions, in particular for pesticidal uses, are composed as follows (%=percent by weight):
Emulsifiable Concentrates:
active ingredient: 1 to 95%, preferably 5 to 50%, more preferably 5 to 20%
surfactant: 1 to 30%, preferably 10 to 20%
solvent: 5 to 98%, preferably 70 to 85%
Dusts:
active ingredient: 0.1 to 10%, preferably 2 to 5%,
solid carrier: 99.9 to 90%, preferably 99.9 to 99%
Suspension Concentrates:
active ingredient: 5 to 75%, preferably 10 to 50%, more preferably 10 to 40%
water: 94 to 24%, preferably 88 to 30%
surfactant: 1 to 40%, preferably 2 to 30%
Oil-Based Suspension Concentrates:
active ingredient: 2 to 75%, preferably 5 to 50%, more preferably 10 to 25%
oil: 94 to 24%, preferably 88 to 30%
surfactant: 1 to 40%, preferably 2 to 30%

Wettable Powders:

active ingredient: 0.5 to 90%, preferably 1 to 80%, more preferably 25 to 75% surfactant: 0.5 to 20%, preferably 1 to 15% solid carrier: 5 to 99%, preferably 15 to 98%

Granulates:

active ingredient: 0.5 to 30%, preferably 3 to 25%, more preferably 3 to 15% solid carrier: 99.5 to 70%, preferably 97 to 85%

FORMULATION EXAMPLES (%=PERCENT BY WEIGHT) IN PARTICULAR FOR PESTICIDAL USES

Example F1

Emulsion Concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

Wettable Powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8a

Suspension Concentrate

| | |
|---|---:|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

Example F8b

Suspension Concentrate

| | |
|---|---:|
| Active ingredient | 10% |
| Naphthalenesulfonic acid, sodium salt condensed with formaldehyde | 2% |
| Solution of an acrylic graft copolymer in water and propyleneglycole | 8% |
| Silicone antifoam emulsion | 0.5% |
| DL-propanediol-(1,2) | 3% |
| Heteropolysaccharide | 0.5% |
| 1,2-Benzisothiazol-3-one | 0.2% |
| Water | 75.8% |

The finely ground active ingredient is mixed intimately with the additives. Suspensions of any desired concentration can be prepared from the thus resulting suspension concentrate by dilution with water.

Example F9

Powders for Dry Seed Treatment

| | a) | b) | c) |
|---|---:|---:|---:|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Example F10

Flowable Concentrate for Seed Treatment

| | |
|---|---:|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Example F11a

Oil-Based Suspension Concentrate (Based on a Vegetable Oil)

| | |
|---|---:|
| Active ingredient | 10% |
| Tristyrylphenole with 16 moles EO | 10% |
| Block copolymer of polyhydroxystearic acid and polyalkylene glycols | 2% |
| AEROSIL 200 | 1% |
| Rape seed oil methyl ester | 12% |
| Oleic acid | 65% |

Example F11b

Oil-Based Suspension Concentrate (Based on a Mineral Oil)

| | |
|---|---:|
| Active ingredient | 10% |
| Ethoxylated alcohols, C16-18 and C18-unsatd | 5% |
| Dodecyl-benzene sulfonic acid Ca-salt linear | 2.5% |
| 2-Pyrrolidinone, 1-ethenylhexadecyl-, homopolymer | 1% |
| Organophilic clay | 1% |
| Mixture of petroleum | 80.5% |

The finely ground active ingredient is mixed intimately with the additives. Suspensions of any desired concentration can be prepared from the thus resulting suspension concentrate by dilution with water.

Preferably, the term "active ingredient" used above refers to one of the compounds selected from Tables 1 to 16 shown above. It also refers to mixtures of the compound of formula I, in particular a compound selected from said Tables 1 to 16, with other insecticides, fungicides, herbicides, safeners, adjuvants and the like, which mixtures are specifically disclosed below.

The compounds of formula I according to the invention, when used as herbicides, can be applied in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means.

Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alcohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{13}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulphate; Sodium lauryl sulphate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations, in particular for herbicidal uses, have the following representative compositions:

(%=percent by weight):

Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

FORMULATION EXAMPLES (%=PERCENT BY WEIGHT) IN PARTICULAR FOR HERBICIDAL USES

F1. Emulsifiable Concentrates

|  | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

F3. Wettable Powders

The active ingredient is thoroughly mixed with the adjuvants and the mixture is thoroughly ground in a suitable mill, yielding wettable powders which can be diluted with water to give suspensions of any desired concentration.

F4. Coated Granules

|  | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

F5. Coated Granules

|  | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

F6. Extruded Granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Water-Dispersible Granules

|  | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% |  |
| Sodium sulphate |  |  | 4% | 5% |
| kaolin | 48% | 30% | 30% |  |

The active ingredient is mixed and ground with the adjuvants and the mixture is moistened with water. The resulting mixture is extruded and then dried in a stream of air.

F8. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F9. Suspension Concentrates

|  | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Preferably, the term "active ingredient" as used in these examples refers to one of the compounds selected from Tables 1 to 16 shown above. It can also refer to mixtures of the compound of formula I, in particular a compound selected from said Tables 1 to 16, with other insecticides, fungicides, herbicides, safeners, adjuvants and the like, which mixtures are specifically disclosed below.

The pesticidal and herbicidal compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO08/017388, which can enhance the efficacy of the inventive compounds; or other active ingredients for achieving specific effects, for example ammonium or phosphonium salts, in particular halides, (hydrogen)sulphates, nitrates, (hydrogen)carbonates, citrates, tartrates, formiates and acetates, as described in WO07/068427 and WO07/068428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests and weeds of the abovementioned type, such as spraying, atomizing, dusting, brushing on, dressing, scattering or pouring—which are to be selected to suit the intended aims of the prevailing circumstances—and the use of the compositions for controlling pests and weeds of the abovementioned type are other subjects of the invention. Typical rates of concentration are between 0.1 and 1000 ppm, preferably between 0.1 and 500 ppm, of active ingredient. The pesticidal rate of application per hectare is generally 1 to 2000 g of active ingredient per hectare, in particular 10 to 1000 g/ha, preferably 10 to 600 g/ha. The herbicidal rate of application is typically 1 to 2000, preferably 1 to 1000, more preferably 1 to 500 g/ha.

A preferred method of application in the field of crop protection is application to the foliage of the plants (foliar application), it being possible to select frequency and rate of application to match the danger of infestation with the pest or weed in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The pesticidal and herbicidal compositions according to the invention are also suitable for the protection of plant propagation material, for example seeds. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

Further methods of application of the compositions according to the invention comprise drip application onto the soil, dipping of parts of plants such as roots bulbs or tubers, drenching the soil, as well as soil injection. These methods are known in the art.

In order to apply a compound of formula I as an insecticide, acaricide, nematicide or molluscicide to a pest, a locus of pest, or to a plant susceptible to attack by a pest, a compound of formula I is usually formulated into a composition which includes, in addition to the compound of formula I, a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula I. The composition is generally used for the control of pests such that a compound of formula I is applied at a rate of from 0.1 g to 10 kg per hectare, preferably from 1 g to 6 kg per hectare, more preferably from 1 g to 1 kg per hectare.

When used in a seed dressing, a compound of formula I is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula I and a suitable carrier or diluent therefor.

In a still further aspect the invention provides a method of combating and controlling pests at a locus which comprises treating the pests or the locus of the pests with an insecticidally, acaricidally, nematicidally or molluscicidally effective amount of a composition comprising a compound of formula I.

In order to apply a compound of formula I as a herbicide, a compound of formula I is usually formulated, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The herbicides may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the herbicidal compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, de-aromatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulphate; Sodium lauryl sulphate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The herbicidal formulations may also comprise additional active substances, for example further herbicides, herbicide safeners, plant growth regulators, fungicides or insecticides. The composition can comprise a herbicidally effective amount of a compound of formula I, and optionally a further herbicide as mixture partner for the compound of formula I, or optionally a safener, or both.

The herbicidal compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I as herbicides may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

In another aspect, the invention provides a herbicidal composition, which comprises a herbicidally effective amount of a compound of formula I, and optionally a further herbicide as mixture partner for the compound of formula I.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the mixture partner of the compound of formula I together with one of the safeners mentioned above.

In still another aspect, the invention provides a method of controlling grasses and weeds in crops of useful plants, which comprises applying a herbicidally effective amount of a compound of formula I, or of a composition comprising such a compound, to the plants or to the locus thereof.

The pesticidal and herbicidal compositions of the invention can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula I.

Dustable powders (DP) may be prepared by mixing a compound of formula I with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula I with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula I and one or more powdered solid diluents or carriers, or from pre-formed blank granules by absorbing a compound of formula I (or a solution thereof, in a suitable agent) in a porous granular material (such as pumice, attapulgite clays, fuller's earth, kieselguhr, diatomaceous earths or ground corn cobs) or by adsorbing a compound of formula I (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula I in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula I in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula I is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula I. SCs may be prepared by ball or bead milling the solid compound of formula I in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula I may be dry milled and added to water, containing agents hereinbefore described, to produce the desired end product.

Oil-based suspension concentrate (OD) may be prepared similarly by suspending finely divided insoluble solid particles of a compound of formula I in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, anti-oxidants, dyestuffs, and/or inert filler materials. An OD is intended and suitable for dilution with water before use to produce a spray solution with sufficient stability to allow spray application through appropriate equipment.

Aerosol formulations comprise a compound of formula I and a suitable propellant (for example n-butane). A compound of formula I may also be dissolved or dispersed in a suitable medium (for example water or a water miscible liquid, such as n-propanol) to provide compositions for use in non-pressurised, hand-actuated spray pumps.

A compound of formula I may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula I and, optionally, a carrier or diluent therefor. The polymeric shell may be produced by either an interfacial polycondensation reaction or by a coacervation procedure. The compositions may provide for controlled release of the compound of formula I and they may be used for seed treatment. A compound of formula I may also be formulated in a biodegradable polymeric matrix to provide a slow, controlled release of the compound.

A compound of formula I may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier).

A composition of the present invention may include one or more additives to improve the biological performance of the composition (for example by improving wetting, retention or distribution on surfaces; resistance to rain on treated surfaces; or uptake or mobility of a compound of formula I). Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula I). Increasing the effect of a compound of formula I may for example be achieved by adding ammonium and/or phosphonium salts, and/or optionally at least one penetration promotor such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula I may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula I (for example 0.0001 to 10%, by weight) depending upon the purpose for which they are to be used.

A compound of formula I may be used in mixtures with fertilisers (for example nitrogen-, potassium- or phosphorus-containing fertilisers, and more particularly ammonium nitrate and/or urea fertilizers). Suitable formulation types include granules of fertiliser. The mixtures suitably contain up to 25% by weight of the compound of formula I.

The invention therefore also provides a fertiliser composition comprising a fertiliser and a compound of formula I.

The compositions of this invention may contain other compounds having biological activity, for example micronutrients or compounds having fungicidal activity or which possess plant growth regulating, herbicidal, safening, insecticidal, nematicidal or acaricidal activity.

The compound of formula I may be the sole active ingredient of the composition or it may be admixed with one or more additional active ingredients such as a pesticide (insect, acarine, mollusc and nematode pesticide), fungicide, synergist, herbicide, safener or plant growth regulator where appropriate. The activity of the compositions according to the invention may thereby be broadened considerably and may have surprising advantages which can also be described, in a wider sense, as synergistic activity. An additional active ingredient may: provide a composition having a broader spectrum of activity or increased persistence at a locus; provide a composition demonstrating better plant/crop tolerance by reducing phytotoxicity; provide a composition controlling insects in their different development stages; synergise the activity or complement the activity (for example by increasing the speed of effect or overcoming repellency) of the compound of formula I; or help to overcome or prevent the development of resistance to individual components. The particular additional active ingredient will depend upon the intended utility of the composition.

Examples of suitable pesticides include the following:
a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, or spinosad, spinetoram or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds such as imidacloprid, thiacloprid, acetamiprid, clothianidin, nitenpyram, dinotefuran or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine or pyrifluquinazon;
r) Spirotetramat, spirodiclofen or spiromesifen;
s) Flubendiamide, chloranthraliniprole, or cyanthraniliprole;
t) Cyenopyrafen or cyflumetofen; or
u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

The following mixtures of the compounds of formula I with active ingredients are preferred, wherein, preferably, the term "COMPOUND OF FORMULA I" refers to a compound selected from the Tables 1 to 16:

an adjuvant selected from the group of substances consisting of an oil of vegetable or animal origin, a mineral oil, alkyl esters of such oils or mixtures of such oils, and petroleum oils (alternative name) (628)+COMPOUND OF FORMULA I, an acaricide selected from the group of substances consisting of 1,1-bis(4-chloro-phenyl)-2-ethoxyethanol (IUPAC name) (910)+COMPOUND OF FORMULA I, 2,4-dichlorophenyl benzenesulfonate (IUPAC/Chemical Abstracts name) (1059)+COMPOUND OF FORMULA I, 2-fluoro-N-methyl-N-1-naphthylacetamide (IUPAC name) (1295)+COMPOUND OF FORMULA I, 4-chlorophenyl phenyl sulfone (IUPAC name) (981)+COMPOUND OF FORMULA I, abamectin (1)+COMPOUND OF FORMULA I, acequinocyl (3)+COMPOUND OF FORMULA I, acetoprole [CCN]+COMPOUND OF FORMULA I, acrinathrin (9)+COMPOUND OF FORMULA I, aldicarb (16)+COMPOUND OF FORMULA I, aldoxycarb (863)+COMPOUND OF FORMULA I, alpha-cypermethrin (202)+COMPOUND OF FORMULA I, amidithion (870)+COMPOUND OF FORMULA I, amidoflumet [CCN]+COMPOUND OF FORMULA I, amidothioate (872)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, aramite (881)+COMPOUND OF FORMULA I, arsenous oxide (882)+COMPOUND OF FORMULA I, AVI 382 (compound code)+COMPOUND OF FORMULA I, AZ 60541 (compound code)+COMPOUND OF FORMULA I, azinphos-ethyl (44)+COMPOUND OF FORMULA I, azinphos-methyl (45)+COMPOUND OF FORMULA I, azobenzene (IUPAC name) (888)+COMPOUND OF FORMULA I, azocyclotin (46)+COMPOUND OF FORMULA I, azothoate (889)+COMPOUND OF FORMULA I, benomyl (62)+COMPOUND OF FORMULA I, benoxafos (alternative name) [CCN]+COMPOUND OF FORMULA I, benzoximate (71)+COMPOUND OF FORMULA I, benzyl benzoate (IUPAC name) [CCN]+COMPOUND OF FORMULA I, bifenazate (74)+COMPOUND OF FORMULA I, bifenthrin (76)+COMPOUND OF FORMULA I, binapacryl (907)+COMPOUND OF FORMULA I, brofenvalerate (alternative name)+COMPOUND OF FORMULA I, bromocyclen (918)+COMPOUND OF FORMULA I, bromophos (920)+COMPOUND OF FORMULA I, bromophos-ethyl (921)+COMPOUND OF FORMULA I, bromopropylate (94)+COMPOUND OF FORMULA I, buprofezin (99)+COMPOUND OF FORMULA I, butocarboxim (103)+COMPOUND OF FORMULA I, butoxycarboxim (104)+COMPOUND OF FORMULA I, butylpyridaben (alternative name)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbophenothion (947)+COMPOUND OF FORMULA I, CGA 50'439 (development code) (125)+COMPOUND OF FORMULA I, chinomethionat (126)+COMPOUND OF FORMULA I, chlorbenside (959)+COMPOUND OF FORMULA I, chlordimeform (964)+COMPOUND OF FORMULA I, chlordimeform hydrochloride (964)+COMPOUND OF FORMULA I, chlorfenapyr (130)+COMPOUND OF FORMULA I, chlorfenethol (968)+COMPOUND OF FORMULA I, chlorfenson (970)+COMPOUND OF FORMULA I, chlorfensulphide (971)+COMPOUND OF FORMULA I, chlorfenvinphos (131)+COMPOUND OF FORMULA I, chlorobenzilate (975)+COMPOUND OF FORMULA I, chloromebuform (977)+COMPOUND OF FORMULA I, chloromethiuron (978)+COMPOUND OF FORMULA I, chloropropylate (983)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, cinerin I (696)+COMPOUND OF FORMULA I, cinerin II (696)+COMPOUND OF FORMULA I, cinerins (696)+COMPOUND OF FORMULA I, clofentezine (158)+COMPOUND OF FORMULA I, closantel (alternative name) [CCN]+COMPOUND OF FORMULA I, coumaphos (174)+COMPOUND OF FORMULA I, crotamiton (alternative name) [CCN]+COMPOUND OF FORMULA I, crotoxyphos (1010)+COMPOUND OF FORMULA I, cufraneb (1013)+COMPOUND OF FORMULA I, cyanthoate (1020)+COMPOUND OF FORMULA I, cyenopyrafen [CCN]+COMPOUND OF FORMULA I, cyflumetofen (CAS Reg. No.: 400882-07-7)+COMPOUND OF FORMULA I, cyhalothrin (196)+COMPOUND OF FORMULA I, cyhexatin (199)+COMPOUND OF FORMULA I, cypermethrin (201)+COMPOUND OF FORMULA I, DCPM (1032)+COMPOUND OF FORMULA I, DDT (219)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diazinon (227)+COMPOUND OF FORMULA I, dichlofluanid (230)+COMPOUND OF FORMULA I, dichlorvos (236)+COMPOUND OF FORMULA I, dicliphos (alternative name)+COMPOUND OF FORMULA I, dicofol (242)+COMPOUND OF FORMULA I, dicrotophos (243)+COMPOUND OF FORMULA I, dienochlor (1071)+COMPOUND OF FORMULA I, diflovidazin [CCN]+COMPOUND OF FORMULA I, dimefox (1081)+COMPOUND OF FORMULA I, dimethoate (262)+COMPOUND OF FORMULA I, dinactin (alternative name) (653)+COMPOUND OF FORMULA I, dinex (1089)+COMPOUND OF FORMULA I, dinex-diclexine (1089)+COMPOUND OF FORMULA I, dinobuton (269)+COMPOUND OF FORMULA I, dinocap (270)+COMPOUND OF FORMULA I, dinocap-4 [CCN]+COMPOUND OF FORMULA I, dinocap-6 [CCN]+COMPOUND OF FORMULA I, dinocton (1090)+COMPOUND OF FORMULA I, dino-penton (1092)+COMPOUND OF FORMULA I, dinosulfon (1097)+COMPOUND OF FORMULA I, dinoterbon (1098)+

COMPOUND OF FORMULA I, dioxathion (1102)+COMPOUND OF FORMULA I, diphenyl sulfone (IUPAC name) (1103)+COMPOUND OF FORMULA I, disulfiram (alternative name) [CCN]+COMPOUND OF FORMULA I, disulfoton (278)+COMPOUND OF FORMULA I, DNOC (282)+COMPOUND OF FORMULA I, dofenapyn (1113)+COMPOUND OF FORMULA I, doramectin (alternative name) [CCN]+COMPOUND OF FORMULA I, endosulfan (294)+COMPOUND OF FORMULA I, endothion (1121)+COMPOUND OF FORMULA I, EPN (297)+COMPOUND OF FORMULA I, eprinomectin (alternative name) [CCN]+COMPOUND OF FORMULA I, ethion (309)+COMPOUND OF FORMULA I, ethoate-methyl (1134)+COMPOUND OF FORMULA I, etoxazole (320)+COMPOUND OF FORMULA I, etrimfos (1142)+COMPOUND OF FORMULA I, fenazaflor (1147)+COMPOUND OF FORMULA I, fenazaquin (328)+COMPOUND OF FORMULA I, fenbutatin oxide (330)+COMPOUND OF FORMULA I, fenothiocarb (337)+COMPOUND OF FORMULA I, fenpropathrin (342)+COMPOUND OF FORMULA I, fenpyrad (alternative name)+COMPOUND OF FORMULA I, fenpyroximate (345)+COMPOUND OF FORMULA I, fenson (1157)+COMPOUND OF FORMULA I, fentrifanil (1161)+COMPOUND OF FORMULA I, fenvalerate (349)+COMPOUND OF FORMULA I, fipronil (354)+COMPOUND OF FORMULA I, fluacrypyrim (360)+COMPOUND OF FORMULA I, fluazuron (1166)+COMPOUND OF FORMULA I, flubenzimine (1167)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenoxuron (370)+COMPOUND OF FORMULA I, flumethrin (372)+COMPOUND OF FORMULA I, fluorbenside (1174)+COMPOUND OF FORMULA I, fluvalinate (1184)+COMPOUND OF FORMULA I, FMC 1137 (development code) (1185)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, gamma-HCH (430)+COMPOUND OF FORMULA I, glyodin (1205)+COMPOUND OF FORMULA I, halfenprox (424)+COMPOUND OF FORMULA I, heptenophos (432)+COMPOUND OF FORMULA I, hexadecyl cyclopropanecarboxylate (IUPAC/Chemical Abstracts name) (1216)+COMPOUND OF FORMULA I, hexythiazox (441)+COMPOUND OF FORMULA I, IKA 2002 (CAS Reg. No.: 211923-74-9)+COMPOUND OF FORMULA I, iodomethane (IUPAC name) (542)+COMPOUND OF FORMULA I, isocarbophos (alternative name) (473)+COMPOUND OF FORMULA I, isopropyl 0-(methoxyaminothiophosphoryl)salicylate (IUPAC name) (473)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, lindane (430)+COMPOUND OF FORMULA I, lufenuron (490)+COMPOUND OF FORMULA I, malathion (492)+COMPOUND OF FORMULA I, malonoben (1254)+COMPOUND OF FORMULA I, mecarbam (502)+COMPOUND OF FORMULA I, mephosfolan (1261)+COMPOUND OF FORMULA I, mesulfen (alternative name) [CCN]+COMPOUND OF FORMULA I, methacrifos (1266)+COMPOUND OF FORMULA I, methamidophos (527)+COMPOUND OF FORMULA I, methidathion (529)+COMPOUND OF FORMULA I, methiocarb (530)+COMPOUND OF FORMULA I, methomyl (531)+COMPOUND OF FORMULA I, methyl bromide (537)+COMPOUND OF FORMULA I, metolcarb (550)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naled (567)+COMPOUND OF FORMULA I, NC-184 (compound code)+COMPOUND OF FORMULA I, NC-512 (compound code)+COMPOUND OF FORMULA I, niflundide (1309)+COMPOUND OF FORMULA I, nikkomycins (alternative name) [CCN]+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, omethoate (594)+COMPOUND OF FORMULA I, oxamyl (602)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, parathion (615)+COMPOUND OF FORMULA I, permethrin (626)+COMPOUND OF FORMULA I, petroleum oils (alternative name) (628)+COMPOUND OF FORMULA I, phenkapton (1330)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosphamidon (639)+COMPOUND OF FORMULA I, phoxim (642)+COMPOUND OF FORMULA I, pirimiphos-methyl (652)+COMPOUND OF FORMULA I, polychloroterpenes (traditional name) (1347)+COMPOUND OF FORMULA I, polynactins (alternative name) (653)+COMPOUND OF FORMULA I, proclonol (1350)+COMPOUND OF FORMULA I, profenofos (662)+COMPOUND OF FORMULA I, promacyl (1354)+COMPOUND OF FORMULA I, propargite (671)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothoate (1362)+COMPOUND OF FORMULA I, pyflubumide+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridaphenthion (701)+COMPOUND OF FORMULA I, pyrimidifen (706)+COMPOUND OF FORMULA I, pyrimitate (1370)+COMPOUND OF FORMULA I, quinalphos (711)+COMPOUND OF FORMULA I, quintiofos (1381)+COMPOUND OF FORMULA I, R-1492 (development code) (1382)+COMPOUND OF FORMULA I, RA-17 (development code) (1383)+COMPOUND OF FORMULA I, rotenone (722)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, sophamide (1402)+COMPOUND OF FORMULA I, spirodiclofen (738)+COMPOUND OF FORMULA I, spiromesifen (739)+COMPOUND OF FORMULA I, SSI-121 (development code) (1404)+COMPOUND OF FORMULA I, sulfiram (alternative name) [CCN]+COMPOUND OF FORMULA I, sulfluramid (750)+COMPOUND OF FORMULA I, sulfotep (753)+COMPOUND OF FORMULA I, sulfur (754)+COMPOUND OF FORMULA I, SZI-121 (development code) (757)+COMPOUND OF FORMULA I, tau-fluvalinate (398)+COMPOUND OF FORMULA I, tebufenpyrad (763)+COMPOUND OF FORMULA I, TEPP (1417)+COMPOUND OF FORMULA I, terbam (alternative name)+COMPOUND OF FORMULA I, tetrachlorvinphos (777)+COMPOUND OF FORMULA I, tetradifon (786)+COMPOUND OF FORMULA I, tetranactin (alternative name) (653)+COMPOUND OF FORMULA I, tetrasul (1425)+COMPOUND OF FORMULA I, thiafenox (alternative name)+COMPOUND OF FORMULA I, thiocarboxime (1431)+COMPOUND OF FORMULA I, thiofanox (800)+COMPOUND OF FORMULA I, thiometon (801)+COMPOUND OF FORMULA I, thioquinox (1436)+COMPOUND OF FORMULA I, thuringiensin (alternative name) [CCN]+COMPOUND OF FORMULA I, triamiphos (1441)+COMPOUND OF FORMULA I, triarathene (1443)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trifenofos (1455)+COMPOUND OF FORMULA I, trinactin (alternative name) (653)+COMPOUND OF FORMULA I, vamidothion (847)+COMPOUND OF FORMULA I, vaniliprole [CCN] and YI-5302 (compound code)+COMPOUND OF FORMULA I, an algicide selected from the group of substances consisting of bethoxazin [CCN]+COMPOUND OF FORMULA I, copper dioctanoate (IUPAC name) (170)+COMPOUND OF FORMULA I, copper sulfate (172)+COMPOUND OF FORMULA I, cybutryne [CCN]+COMPOUND OF FORMULA I, dichlone (1052)+COMPOUND OF FORMULA I, dichlorophen (232)+COMPOUND OF FORMULA I, endothal (295)+COMPOUND OF FORMULA I, fentin (347)+COMPOUND OF FORMULA I, hydrated lime [CCN]+COMPOUND OF FORMULA I, nabam (566)+COMPOUND OF FORMULA I, quinoclamine (714)+COMPOUND OF FORMULA I, quinonamid (1379)+COMPOUND OF FORMULA I, simazine (730)+COMPOUND OF FORMULA I, triphenyltin acetate (IUPAC name) (347) and triphenyltin hydroxide (IUPAC name) (347)+COMPOUND OF FORMULA I, an anthelmintic selected from the group of substances consisting of abamectin (1)+COMPOUND OF FORMULA I, crufomate (1011)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ivermectin (alternative name) [CCN]+COMPOUND OF FORMULA I, milbemycin oxime (alternative name) [CCN]+COMPOUND OF FORMULA I, moxidectin (alternative name) [CCN]+COMPOUND OF FORMULA I, piperazine [CCN]+COMPOUND OF FORMULA I, selamectin (alternative name) [CCN]+COMPOUND OF FORMULA I, spinosad (737) and thiophanate (1435)+COMPOUND OF FORMULA I, an avicide selected from the group of substances consisting of chloralose (127)+COMPOUND OF FORMULA I, endrin (1122)+COMPOUND OF FORMULA I, fenthion (346)+COMPOUND OF FORMULA I, pyridin-4-amine (IUPAC name) (23) and strychnine (745)+COMPOUND OF FORMULA I, a bactericide selected from the group of substances consisting of 1-hydroxy-1H-pyridine-2-thione (IUPAC name) (1222)+COMPOUND OF FORMULA I, 4-(quinoxalin-2-ylamino)benzenesulfonamide (IUPAC name) (748)+COMPOUND OF FORMULA I, 8-hydroxyquinoline sulfate (446)+COMPOUND OF FORMULA I, bronopol (97)+COMPOUND OF FORMULA I, copper dioctanoate (IUPAC name) (170)+COMPOUND OF FORMULA I, copper hydroxide (IUPAC name) (169)+COMPOUND OF FORMULA I, cresol [CCN]+COMPOUND OF FORMULA I, dichlorophen (232)+COMPOUND OF FORMULA I, dipyrithione (1105)+COMPOUND OF FORMULA I, dodicin (1112)+COMPOUND OF FORMULA I, fenaminosulf (1144)+COMPOUND OF FORMULA I, formaldehyde (404)+COMPOUND OF FORMULA I, hydrargaphen (alternative name) [CCN]+COMPOUND OF FORMULA I, kasugamycin (483)+COMPOUND OF FORMULA I, kasugamycin hydrochloride hydrate (483)+COMPOUND OF FORMULA I, nickel bis(dimethyldithiocarbamate) (IUPAC name) (1308)+COMPOUND OF FORMULA I, nitrapyrin (580)+COMPOUND OF FORMULA I, octhilinone (590)+COMPOUND OF FORMULA I, oxolinic acid (606)+COMPOUND OF FORMULA I, oxytetracycline (611)+COMPOUND OF FORMULA I, potassium hydroxyquinoline sulfate (446)+COMPOUND OF FORMULA I, probenazole (658)+COMPOUND OF FORMULA I, streptomycin (744)+COMPOUND OF FORMULA I, streptomycin sesquisulfate (744)+COMPOUND OF FORMULA I, tecloftalam (766)+COMPOUND OF FORMULA I, and thiomersal (alternative name) [CCN]+COMPOUND OF FORMULA I, a biological agent selected from the group of substances consisting of *Adoxophyes orana* GV (alternative name) (12)+COMPOUND OF FORMULA I, *Agrobacterium radiobacter* (alternative name) (13)+COMPOUND OF FORMULA I, *Amblyseius* spp. (alternative name) (19)+COMPOUND OF FORMULA I, *Anagrapha falcifera* NPV (alternative name) (28)+COMPOUND OF FORMULA I, *Anagrus atomus* (alternative name) (29)+COMPOUND OF FORMULA I, *Aphelinus abdominalis* (alternative name) (33)+COMPOUND OF FORMULA I, *Aphidius colemani* (alternative name) (34)+COMPOUND OF FORMULA I, *Aphidoletes aphidimyza* (alternative name) (35)+COMPOUND OF FORMULA I, *Autographa californica* NPV (alternative name) (38)+COMPOUND OF FORMULA I, *Bacillus firmus* (alternative name) (48)+COMPOUND OF FORMULA I, *Bacillus sphaericus* Neide (scientific name) (49)+COMPOUND OF FORMULA I, *Bacillus thuring-*

*iensis* Berliner (scientific name) (51)+COMPOUND OF FORMULA I, *Bacillus thuringiensis* subsp. *aizawai* (scientific name) (51)+COMPOUND OF FORMULA I, *Bacillus thuringiensis* subsp. *israelensis* (scientific name) (51)+COMPOUND OF FORMULA I, *Bacillus thuringiensis* subsp. *japonensis* (scientific name) (51)+COMPOUND OF FORMULA I, *Bacillus thuringiensis* subsp. *kurstaki* (scientific name) (51)+COMPOUND OF FORMULA I, *Bacillus thuringiensis* subsp. *tenebrionis* (scientific name) (51)+COMPOUND OF FORMULA I, *Beauveria bassiana* (alternative name) (53)+COMPOUND OF FORMULA I, *Beauveria brongniartii* (alternative name) (54)+COMPOUND OF FORMULA I, *Chrysoperla carnea* (alternative name) (151)+COMPOUND OF FORMULA I, *Cryptolaemus montrouzieri* (alternative name) (178)+COMPOUND OF FORMULA I, *Cydia pomonella* GV (alternative name) (191)+COMPOUND OF FORMULA I, *Dacnusa sibirica* (alternative name) (212)+COMPOUND OF FORMULA I, *Diglyphus isaea* (alternative name) (254)+COMPOUND OF FORMULA I, *Encarsia formosa* (scientific name) (293)+COMPOUND OF FORMULA I, *Eretmocerus eremicus* (alternative name) (300)+COMPOUND OF FORMULA I, *Helicoverpa zea* NPV (alternative name) (431)+COMPOUND OF FORMULA I, *Heterorhabditis bacteriophora* and *H. megidis* (alternative name) (433)+COMPOUND OF FORMULA I, *Hippodamia convergens* (alternative name) (442)+COMPOUND OF FORMULA I, *Leptomastix dactylopii* (alternative name) (488)+COMPOUND OF FORMULA I, *Macrolophus caliginosus* (alternative name) (491)+COMPOUND OF FORMULA I, *Mamestra brassicae* NPV (alternative name) (494)+COMPOUND OF FORMULA I, *Metaphycus helvolus* (alternative name) (522)+COMPOUND OF FORMULA I, *Metarhizium anisopliae* var. *acridum* (scientific name) (523)+COMPOUND OF FORMULA I, *Metarhizium anisopliae* var. *anisopliae* (scientific name) (523)+COMPOUND OF FORMULA I, *Neodiprion sertifer* NPV and *N. lecontei* NPV (alternative name) (575)+COMPOUND OF FORMULA I, *Orius* spp. (alternative name) (596)+COMPOUND OF FORMULA I, *Pasteuria usgae* (alternative name)+COMPOUND OF FORMULA I, *Paecilomyces fumosoroseus* (alternative name) (613)+COMPOUND OF FORMULA I, *Phytoseiulus persimilis* (alternative name) (644)+COMPOUND OF FORMULA I, *Spodoptera exigua* multicapsid nuclear polyhedrosis virus (scientific name) (741)+COMPOUND OF FORMULA I, *Steinernema bibionis* (alternative name) (742)+COMPOUND OF FORMULA I, *Steinernema carpocapsae* (alternative name) (742)+COMPOUND OF FORMULA I, *Steinernema feltiae* (alternative name) (742)+COMPOUND OF FORMULA I, *Steinernema glaseri* (alternative name) (742)+COMPOUND OF FORMULA I, *Steinernema riobrave* (alternative name) (742)+COMPOUND OF FORMULA I, *Steinernema riobravis* (alternative name) (742)+COMPOUND OF FORMULA I, *Steinernema scapterisci* (alternative name) (742)+COMPOUND OF FORMULA I, *Steinernema* spp. (alternative name) (742)+COMPOUND OF FORMULA I, *Trichoderma* spp. (alternative name)+COMPOUND OF FORMULA I, *Trichogramma* spp. (alternative name) (826)+COMPOUND OF FORMULA I, *Typhlodromus occidentalis* (alternative name) (844) and *Verticillium lecanii* (alternative name) (848)+COMPOUND OF FORMULA I, a soil sterilant selected from the group of substances consisting of dimethyl disulfide (IUPAC name)+COMPOUND OF FORMULA I, iodomethane (IUPAC name) (542) and methyl bromide (537)+COMPOUND OF FORMULA I, a chemosterilant selected from the group of substances consisting of apholate [CCN]+COMPOUND OF FORMULA I, bisazir (alternative name) [CCN]+COMPOUND OF FORMULA I, busulfan (alternative name) [CCN]+COMPOUND OF FORMULA I, diflubenzuron (250)+COMPOUND OF FORMULA I, dimatif (alternative name) [CCN]+COMPOUND OF FORMULA I, hemel [CCN]+COMPOUND OF FORMULA I, hempa [CCN]+COMPOUND OF FORMULA I, metepa [CCN]+COMPOUND OF FORMULA I, methiotepa [CCN]+COMPOUND OF FORMULA I, methyl apholate [CCN]+COMPOUND OF FORMULA I, morzid [CCN]+COMPOUND OF FORMULA I, penfluron (alternative name) [CCN]+COMPOUND OF FORMULA I, tepa [CCN]+COMPOUND OF FORMULA I, thiohempa (alternative name) [CCN]+COMPOUND OF FORMULA I, thiotepa (alternative name) [CCN]+COMPOUND OF FORMULA I, tretamine (alternative name) [CCN] and uredepa (alternative name) [CCN]+COMPOUND OF FORMULA I, an insect pheromone selected from the group of substances consisting of (E)-dec-5-en-1-yl acetate with (E)-dec-5-en-1-ol (IUPAC name) (222)+COMPOUND OF FORMULA I, (E)-tridec-4-en-1-yl acetate (IUPAC name) (829)+COMPOUND OF FORMULA I, (E)-6-methylhept-2-en-4-ol (IUPAC name) (541)+COMPOUND OF FORMULA I, (E,Z)-tetradeca-4,10-dien-1-yl acetate (IUPAC name) (779)+COMPOUND OF FORMULA I, (Z)-dodec-7-en-1-yl acetate (IUPAC name) (285)+COMPOUND OF FORMULA I, (Z)-hexadec-11-enal (IUPAC name) (436)+COMPOUND OF FORMULA I, (Z)-hexadec-11-en-1-yl acetate (IUPAC name) (437)+COMPOUND OF FORMULA I, (Z)-hexadec-13-en-11-yn-1-yl acetate (IUPAC name) (438)+COMPOUND OF FORMULA I, (Z)-icos-13-en-10-one (IUPAC name) (448)+COMPOUND OF FORMULA I, (Z)-tetradec-7-en-1-al (IUPAC name) (782)+COMPOUND OF FORMULA I, (Z)-tetradec-9-en-1-ol (IUPAC name) (783)+COMPOUND OF FORMULA I, (Z)-tetradec-9-en-1-yl acetate (IUPAC name) (784)+COMPOUND OF FORMULA I, (7E,9Z)-dodeca-7,9-dien-1-yl acetate (IUPAC name) (283)+COMPOUND OF FORMULA I, (9Z,11E)-tetradeca-9,11-dien-1-yl acetate (IUPAC name) (780)+COMPOUND OF FORMULA I, (9Z,12E)-tetradeca-9,12-dien-1-yl acetate (IUPAC name) (781)+COMPOUND OF FORMULA I, 14-methyloctadec-1-ene (IUPAC name) (545)+COMPOUND OF FORMULA I, 4-methylnonan-5-ol with 4-methylnonan-5-one (IUPAC name) (544)+COMPOUND OF FORMULA I, alpha-multistriatin (alternative name) [CCN]+COMPOUND OF FORMULA I, brevicomin (alternative name) [CCN]+COMPOUND OF FORMULA I, codlelure (alternative name) [CCN]+COMPOUND OF FORMULA I, codlemone (alternative name) (167)+COMPOUND OF FORMULA I, cuelure (alternative name) (179)+COMPOUND OF FORMULA I, disparlure (277)+COMPOUND OF FORMULA I, (E,Z)-7,9-dodecadien-1-yl acetate (IUPAC name)+COMPOUND OF FORMULA I, dodec-8-en-1-yl acetate (IUPAC name) (286)+COMPOUND OF FORMULA I, dodec-9-en-1-yl acetate (IUPAC name) (287)+COMPOUND OF FORMULA I, dodeca-8+

COMPOUND OF FORMULA I, 10-dien-1-yl acetate (IUPAC name) (284)+COMPOUND OF FORMULA I, dominicalure (alternative name) [CCN]+COMPOUND OF FORMULA I, ethyl 4-methyloctanoate (IUPAC name) (317)+COMPOUND OF FORMULA I, eugenol (alternative name) [CCN]+COMPOUND OF FORMULA I, exosex SPTab (alternative name)+COMPOUND OF FORMULA I, frontalin (alternative name) [CCN]+COMPOUND OF FORMULA I, gossyplure (alternative name) (420)+COMPOUND OF FORMULA I, grandlure (421)+COMPOUND OF FORMULA I, grandlure I (alternative name) (421)+COMPOUND OF FORMULA I, grandlure II (alternative name) (421)+COMPOUND OF FORMULA I, grandlure III (alternative name) (421)+COMPOUND OF FORMULA I, grandlure IV (alternative name) (421)+COMPOUND OF FORMULA I, hexalure [CCN]+COMPOUND OF FORMULA I, imicyafos (alternative name) [CCN]+COMPOUND OF FORMULA I, ipsdienol (alternative name) [CCN]+COMPOUND OF FORMULA I, ipsenol (alternative name) [CCN]+COMPOUND OF FORMULA I, japonilure (alternative name) (481)+COMPOUND OF FORMULA I, lineatin (alternative name) [CCN]+COMPOUND OF FORMULA I, litlure (alternative name) [CCN]+COMPOUND OF FORMULA I, looplure (alternative name) [CCN]+COMPOUND OF FORMULA I, medlure [CCN]+COMPOUND OF FORMULA I, megatomoic acid (alternative name) [CCN]+COMPOUND OF FORMULA I, methyl eugenol (alternative name) (540)+COMPOUND OF FORMULA I, muscalure (563)+COMPOUND OF FORMULA I, octadeca-2,13-dien-1-yl acetate (IUPAC name) (588)+COMPOUND OF FORMULA I, octadeca-3,13-dien-1-yl acetate (IUPAC name) (589)+COMPOUND OF FORMULA I, orfralure (alternative name) [CCN]+COMPOUND OF FORMULA I, oryctalure (alternative name) (317)+COMPOUND OF FORMULA I, ostramone (alternative name) [CCN]+COMPOUND OF FORMULA I, siglure [CCN]+COMPOUND OF FORMULA I, sordidin (alternative name) (736)+COMPOUND OF FORMULA I, sulcatol (alternative name) [CCN]+COMPOUND OF FORMULA I, tetradec-11-en-1-yl acetate (IUPAC name) (785)+COMPOUND OF FORMULA I, trimedlure (839)+COMPOUND OF FORMULA I, trimedlure A (alternative name) (839)+COMPOUND OF FORMULA I, trimedlure $B_1$ (alternative name) (839)+COMPOUND OF FORMULA I, trimedlure $B_2$ (alternative name) (839)+COMPOUND OF FORMULA I, trimedlure C (alternative name) (839) and trunc-call (alternative name) [CCN]+COMPOUND OF FORMULA I, an insect repellent selected from the group of substances consisting of 2-(octylthio)-ethanol (IUPAC name) (591)+COMPOUND OF FORMULA I, butopyronoxyl (933)+COMPOUND OF FORMULA I, butoxy (polypropylene glycol) (936)+COMPOUND OF FORMULA I, dibutyl adipate (IUPAC name) (1046)+COMPOUND OF FORMULA I, dibutyl phthalate (1047)+COMPOUND OF FORMULA I, dibutyl succinate (IUPAC name) (1048)+COMPOUND OF FORMULA I, diethyltoluamide [CCN]+COMPOUND OF FORMULA I, dimethyl carbate [CCN]+COMPOUND OF FORMULA I, dimethyl phthalate [CCN]+COMPOUND OF FORMULA I, ethyl hexanediol (1137)+COMPOUND OF FORMULA I, hexamide [CCN]+COMPOUND OF FORMULA I, methoquin-butyl (1276)+COMPOUND OF FORMULA I, methylneodecanamide [CCN]+COMPOUND OF FORMULA I, oxamate [CCN] and picaridin [CCN]+COMPOUND OF FORMULA I, an insecticide selected from the group of substances consisting of 1-dichloro-1-nitroethane (IUPAC/Chemical Abstracts name) (1058)+COMPOUND OF FORMULA I, 1,1-dichloro-2,2-bis(4-ethylphenyl)ethane (IUPAC name) (1056), +COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1-bromo-2-chloroethane (IUPAC/Chemical Abstracts name) (916)+COMPOUND OF FORMULA I, 2,2,2-trichloro-1-(3,4-dichloro-phenyl)ethyl acetate (IUPAC name) (1451)+COMPOUND OF FORMULA I, 2,2-dichlorovinyl 2-ethylsulfinylethyl methyl phosphate (IUPAC name) (1066)+COMPOUND OF FORMULA I, 2-(1,3-dithiolan-2-yl)phenyl dimethylcarbamate (IUPAC/Chemical Abstracts name) (1109)+COMPOUND OF FORMULA I, 2-(2-butoxyethoxy)ethyl thiocyanate (IUPAC/Chemical Abstracts name) (935)+COMPOUND OF FORMULA I, 2-(4,5-dimethyl-1,3-dioxolan-2-yl)phenyl methylcarbamate (IUPAC/Chemical Abstracts name) (1084)+COMPOUND OF FORMULA I, 2-(4-chloro-3,5-xylyloxy)ethanol (IUPAC name) (986)+COMPOUND OF FORMULA I, 2-chlorovinyl diethyl phosphate (IUPAC name) (984)+COMPOUND OF FORMULA I, 2-imidazolidone (IUPAC name) (1225)+COMPOUND OF FORMULA I, 2-isovalerylindan-1,3-dione (IUPAC name) (1246)+COMPOUND OF FORMULA I, 2-methyl(prop-2-ynyl)aminophenyl methylcarbamate (IUPAC name) (1284)+COMPOUND OF FORMULA I, 2-thiocyanatoethyl laurate (IUPAC name) (1433)+COMPOUND OF FORMULA I, 3-bromo-1-chloroprop-1-ene (IUPAC name) (917)+COMPOUND OF FORMULA I, 3-methyl-1-phenylpyrazol-5-yl dimethyl-carbamate (IUPAC name) (1283)+COMPOUND OF FORMULA I, 4-methyl (prop-2-ynyl)amino-3,5-xylyl methylcarbamate (IUPAC name) (1285)+COMPOUND OF FORMULA I, 5,5-dimethyl-3-oxocyclohex-1-enyl dimethylcarbamate (IUPAC name) (1085)+COMPOUND OF FORMULA I, abamectin (1)+COMPOUND OF FORMULA I, acephate (2)+COMPOUND OF FORMULA I, acetamiprid (4)+COMPOUND OF FORMULA I, acethion (alternative name) [CCN]+COMPOUND OF FORMULA I, acetoprole [CCN]+COMPOUND OF FORMULA I, acrinathrin (9)+COMPOUND OF FORMULA I, acrylonitrile (IUPAC name) (861)+COMPOUND OF FORMULA I, afidopyropen or coprapidpen+compound of formula I, alanycarb (15)+COMPOUND OF FORMULA I, aldicarb (16)+COMPOUND OF FORMULA I, aldoxycarb (863)+COMPOUND OF FORMULA I, aldrin (864)+COMPOUND OF FORMULA I, allethrin (17)+COMPOUND OF FORMULA I, allosamidin (alternative name) [CCN]+COMPOUND OF FORMULA I, allyxycarb (866)+COMPOUND OF FORMULA I, alpha-cypermethrin (202)+COMPOUND OF FORMULA I, alpha-ecdysone (alternative name) [CCN]+COMPOUND OF FORMULA I, alpha-endosulfan [CCN]+COMPOUND OF FORMULA I, aluminium phosphide (640)+COMPOUND OF FORMULA I, amidithion (870)+COMPOUND OF FORMULA I, amidothioate (872)+COMPOUND OF FORMULA I, aminocarb (873)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, anabasine (877)+COMPOUND OF FORMULA I, athidathion (883)+COMPOUND OF FORMULA I, AVI 382 (compound code)+COMPOUND OF FORMULA I, AZ 60541 (compound code)+COMPOUND OF FORMULA I, azadirachtin (alternative name) (41)+COMPOUND OF FORMULA I, azamethiphos (42)+COMPOUND OF FORMULA I, azinphos-ethyl (44)+COMPOUND OF FORMULA I, azinphos-methyl (45)+COMPOUND OF FORMULA I, azothoate (889)+COMPOUND OF FORMULA I, Bacillus thuringiensis delta endotoxins (alternative name) (52)+COMPOUND OF FORMULA I, barium hexafluorosilicate (alternative name) [CCN]+COMPOUND OF FORMULA I, barium polysulfide (IUPAC/Chemical Abstracts name) (892)+COMPOUND OF FORMULA I, barthrin [CCN]+COMPOUND OF FORMULA I, Bayer 22/190 (development code) (893)+COMPOUND OF FORMULA I, Bayer 22408 (development code) (894)+COMPOUND OF FORMULA I, bendiocarb (58)+COMPOUND OF FORMULA I, benfuracarb (60)+COMPOUND OF FORMULA I, bensultap (66)+COMPOUND OF FORMULA I, beta-cyfluthrin (194)+COMPOUND OF FORMULA I, beta-cypermethrin (203)+COMPOUND OF FORMULA I, bifenthrin (76)+COMPOUND OF FORMULA I, bioallethrin (78)+COMPOUND OF FORMULA I, bioallethrin S-cyclopentenyl isomer (alternative name) (79)+COMPOUND OF FORMULA I, bioethanomethrin [CCN]+COMPOUND OF FORMULA I, biopermethrin (908)+COMPOUND OF FORMULA I, bioresmethrin (80)+COMPOUND OF FORMULA I, bis(2-chloroethyl) ether (IUPAC name) (909)+COMPOUND OF FORMULA I, bistrifluron (83)+COMPOUND OF FORMULA I, borax (86)+COMPOUND OF FORMULA I, brofenvalerate (alternative name)+COMPOUND OF FORMULA I, bromfenvinfos (914)+COMPOUND OF FORMULA I, bromocyclen (918)+COMPOUND OF FORMULA I, bromo-DDT (alternative name) [CCN]+COMPOUND OF FORMULA I, bromophos (920)+COMPOUND OF FORMULA I, bromophos-ethyl (921)+COMPOUND OF FORMULA I, bufencarb (924)+COMPOUND OF FORMULA I, buprofezin (99)+COMPOUND OF FORMULA I, butacarb (926)+COMPOUND OF FORMULA I, butathiofos (927)+COMPOUND OF FORMULA I, butocarboxim (103)+COMPOUND OF FORMULA I, butonate (932)+COMPOUND OF FORMULA I, butoxycarboxim (104)+COMPOUND OF FORMULA I, butylpyridaben (alternative name)+COMPOUND OF FORMULA I, cadusafos (109)+COMPOUND OF FORMULA I, calcium arsenate [CCN]+COMPOUND OF FORMULA I, calcium cyanide (444)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbon disulfide (IUPAC/Chemical Abstracts name) (945)+COMPOUND OF FORMULA I, carbon tetrachloride (IUPAC name) (946)+COMPOUND OF FORMULA I, carbophenothion (947)+COMPOUND OF FORMULA I, carbosulfan (119)+COMPOUND OF FORMULA I, cartap (123)+COMPOUND OF FORMULA I, cartap hydrochloride (123)+COMPOUND OF FORMULA I, celangulin (alternative name)+COMPOUND OF FORMULA I, cevadine (alternative name) (725)+COMPOUND OF FORMULA I, chlorantraniliprole [CCN]+COMPOUND OF FORMULA I, chlorbicyclen (960)+COMPOUND OF FORMULA I, chlordane (128)+COMPOUND OF FORMULA I, chlordecone (963)+COMPOUND OF FORMULA I, chlordimeform (964)+COMPOUND OF FORMULA I, chlordimeform hydrochloride (964)+COMPOUND OF FORMULA I, chlorethoxyfos (129)+COMPOUND OF FORMULA I, chlorfenapyr (130)+COMPOUND OF FORMULA I, chlorfenvinphos (131)+COMPOUND OF FORMULA I, chlorfluazuron (132)+COMPOUND OF FORMULA I, chlormephos (136)+COMPOUND OF FORMULA I, chloroform [CCN]+COMPOUND OF FORMULA I, chloropicrin (141)+COMPOUND OF FORMULA I, chlorphoxim (989)+COMPOUND OF FORMULA I, chlorprazophos (990)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, chromafenozide (150)+COMPOUND OF FORMULA I, cinerin I (696)+COMPOUND OF FORMULA I, cinerin II (696)+COMPOUND OF FORMULA I, cinerins (696)+COMPOUND OF FORMULA I, cis-resmethrin (alternative name)+COMPOUND OF FORMULA I, cismethrin (80)+COMPOUND OF FORMULA I, clocythrin (alternative name)+COMPOUND OF FORMULA I, cloethocarb (999)+COMPOUND OF FORMULA I, closantel (alternative name) [CCN]+COMPOUND OF FORMULA I, clothianidin (165)+COMPOUND OF FORMULA I, copper acetoarsenite [CCN]+COMPOUND OF FORMULA I, copper arsenate [CCN]+COMPOUND OF FORMULA I, copper oleate [CCN]+COMPOUND OF FORMULA I, coumaphos (174)+COMPOUND OF FORMULA I, coumithoate (1006)+COMPOUND OF FORMULA I, crotamiton (alternative name) [CCN]+COMPOUND OF FORMULA I, crotoxyphos (1010)+COMPOUND OF FORMULA I, crufomate (1011)+COMPOUND OF FORMULA I, cryolite (alternative name) (177)+COMPOUND OF FORMULA I, CS 708 (development code) (1012)+COMPOUND OF FORMULA I, cyanofenphos (1019)+COMPOUND OF FORMULA I, cyanophos (184)+COMPOUND OF FORMULA I, cyanthoate (1020)+COMPOUND OF FORMULA I, cyantraniliprole [CCN]+COMPOUND OF FORMULA I, cyclethrin [CCN]+COMPOUND OF FORMULA I, cycloprothrin (188)+COMPOUND OF FORMULA I, cyfluthrin (193)+COMPOUND OF FORMULA I, cyhalothrin (196)+COMPOUND OF FORMULA I, cypermethrin (201)+COMPOUND OF FORMULA I, cyphenothrin (206)+COMPOUND OF FORMULA I, cyromazine (209)+COMPOUND OF FORMULA I, cythioate (alternative name) [CCN]+COMPOUND OF FORMULA I, d-limonene (alternative name) [CCN]+COMPOUND OF FORMULA I, d-tetramethrin (alternative name) (788)+COMPOUND OF FORMULA I, DAEP (1031)+COMPOUND OF FORMULA I, dazomet (216)+COMPOUND OF FORMULA I, DDT (219)+COMPOUND OF FORMULA I, decarbofuran (1034)+COMPOUND OF FORMULA I, deltamethrin (223)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diamidafos (1044)+COMPOUND OF FORMULA I, diazinon (227)+COMPOUND OF FORMULA I, dicapthon (1050)+COMPOUND OF FORMULA I, dichlofenthion (1051)+COMPOUND OF FORMULA I, dichlorvos (236)+COMPOUND OF FORMULA I, dicliphos (alternative name)+COMPOUND OF FORMULA I, dicresyl (alternative name) [CCN]+COMPOUND OF FORMULA I, dicrotophos (243)+COMPOUND OF FORMULA I, dicyclanil (244)+COMPOUND OF FORMULA I, dieldrin (1070)+COMPOUND OF FORMULA I, diethyl 5-methylpyrazol-3-yl phosphate (IUPAC name) (1076)+COMPOUND OF FORMULA I, diflubenzuron (250)+COMPOUND OF FORMULA I, dilor (alternative name) [CCN]+COMPOUND OF FORMULA I, dimefluthrin [CCN]+COMPOUND OF FORMULA I, dimefox (1081)+COMPOUND OF FORMULA I, dimetan (1085)+COMPOUND OF FORMULA I, dimethoate (262)+COMPOUND OF FORMULA I, dimethrin (1083)+COMPOUND OF FORMULA I, dimethylvinphos (265)+COMPOUND OF FORMULA I, dimetilan (1086)+COMPOUND OF FORMULA I, dinex (1089)+COMPOUND OF FORMULA I, dinex-diclexine (1089)+COMPOUND OF FORMULA I, dinoprop (1093)+COMPOUND OF FORMULA I, dinosam (1094)+COMPOUND OF FORMULA I, dinoseb (1095)+COMPOUND OF FORMULA I, dinotefuran (271)+COMPOUND OF FORMULA I, diofenolan (1099)+COMPOUND OF FORMULA I, dioxabenzofos (1100)+COMPOUND OF FORMULA I, dioxacarb (1101)+COMPOUND OF FORMULA I, dioxathion (1102)+COMPOUND OF FORMULA I, disulfoton (278)+COMPOUND OF FORMULA I, dithicrofos (1108)+COMPOUND OF FORMULA I, DNOC (282)+COMPOUND OF FORMULA I, doramectin (alternative name) [CCN]+COMPOUND OF FORMULA I, DSP (1115)+COMPOUND OF FORMULA I, ecdysterone (alternative name) [CCN]+COMPOUND OF FORMULA I, EI 1642 (development code) (1118)+COMPOUND OF FORMULA I, emamectin (291)+COMPOUND OF FORMULA I, emamectin benzoate (291)+COMPOUND OF FORMULA I, EMPC (1120)+COMPOUND OF FORMULA I, empenthrin (292)+COMPOUND OF FORMULA I, endosulfan (294)+COMPOUND OF FORMULA I, endothion (1121)+COMPOUND OF FORMULA I, endrin (1122)+COMPOUND OF FORMULA I, EPBP (1123)+COMPOUND OF FORMULA I, EPN (297)+COMPOUND OF FORMULA I, epofenonane (1124)+COMPOUND OF FORMULA I, eprinomectin (alternative name) [CCN]+COMPOUND OF FORMULA I, eremophilone oil+COMPOUND OF FORMULA I, esfenvalerate (302)+COMPOUND OF FORMULA I, etaphos (alternative name) [CCN]+COMPOUND OF FORMULA I, ethiofencarb (308)+COMPOUND OF FORMULA I, ethion (309)+COMPOUND OF FORMULA I, ethiprole (310)+COMPOUND OF FORMULA I, ethoate-methyl (1134)+COMPOUND OF FORMULA I, ethoprophos (312)+COMPOUND OF FORMULA I, ethyl formate (IUPAC name) [CCN]+COMPOUND OF FORMULA I, ethyl-DDD (alternative name) (1056)+COMPOUND OF FORMULA I, ethylene dibromide (316)+COMPOUND OF FORMULA I, ethylene dichloride (chemical name) (1136)+COMPOUND OF FORMULA I, ethylene oxide [CCN]+COMPOUND OF FORMULA I, etofenprox (319)+COMPOUND OF FORMULA I, etrimfos (1142)+COMPOUND OF FORMULA I, EXD (1143)+COMPOUND OF FORMULA I, famphur (323)+COMPOUND OF FORMULA I, fenamiphos (326)+COMPOUND OF FORMULA I, fenazaflor (1147)+COMPOUND OF FORMULA I, fenchlorphos (1148)+COMPOUND OF FORMULA I, fenethacarb (1149)+COMPOUND OF FORMULA I, fenfluthrin (1150)+COMPOUND OF FORMULA I, fenitrothion (335)+COMPOUND OF FORMULA I, fenobucarb (336)+COMPOUND OF FORMULA I, fenoxacrim (1153)+COMPOUND OF FORMULA I, fenoxycarb (340)+COMPOUND OF FORMULA I, fenpirithrin (1155)+COMPOUND OF FORMULA I, fenpropathrin (342)+COMPOUND OF FORMULA I, fenpyrad (alternative name)+COMPOUND OF FORMULA I, fensulfothion (1158)+COMPOUND OF FORMULA I, fenthion (346)+COMPOUND OF FORMULA I, fenthion-ethyl [CCN]+COMPOUND OF FORMULA I, fenvalerate (349)+COMPOUND OF FORMULA I, fipronil (354)+COMPOUND OF FORMULA I, flometoquin [CCN]+COMPOUND OF FORMULA I, flonicamid (358)+COMPOUND OF FORMULA I, flubendiamide (CAS. Reg. No.: 272451-65-7)+COMPOUND OF FORMULA I, flucofuron (1168)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, fluensulfone [CCN]+COMPOUND OF FORMULA I, flufenerim [CCN]+COMPOUND OF FORMULA I, flufenoxuron (370)+COMPOUND OF FORMULA I, flufenprox (1171)+COMPOUND OF FORMULA I, flufiprole [CCN]+COMPOUND OF FORMULA I, flumethrin (372)+COMPOUND OF FORMULA I, flupyradifurone [CCN]+COMPOUND OF FORMULA I, fluvalinate (1184)+COMPOUND OF FORMULA I, FMC 1137 (development code) (1185)+COMPOUND OF FORMULA I, fonofos (1191)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, fosmethilan (1194)+COMPOUND OF FORMULA I, fospirate (1195)+COMPOUND OF FORMULA I, fosthiazate (408)+COMPOUND OF FORMULA I, fosthietan (1196)+COMPOUND OF FORMULA I, furathiocarb (412)+COMPOUND OF FORMULA I, furethrin (1200)+COMPOUND OF FORMULA I, gamma-cyhalothrin (197)+COMPOUND OF FORMULA I, gamma-HCH (430)+COMPOUND OF FORMULA I, guazatine (422)+COMPOUND OF FORMULA I, guazatine acetates (422)+COMPOUND OF FORMULA I, GY-81 (development code) (423)+COMPOUND OF FORMULA I, halfenprox (424)+COMPOUND OF FORMULA I, halofenozide (425)+COMPOUND OF FORMULA I, HCH (430)+COMPOUND OF FORMULA I, HEOD (1070)+COMPOUND OF FORMULA I, heptachlor (1211)+COMPOUND OF FORMULA I, heptenophos (432)+COMPOUND OF FORMULA I, heterophos [CCN]+COMPOUND OF FORMULA I, hexaflumuron (439)+COMPOUND OF FORMULA I, HHDN (864)+COMPOUND OF FORMULA I, hydramethylnon (443)+COMPOUND OF FORMULA I, hydrogen cyanide (444)+COMPOUND OF FORMULA I, hydroprene (445)+COMPOUND OF FORMULA I, hyquincarb (1223)+COMPOUND OF FORMULA I, imidacloprid (458)+COMPOUND OF FORMULA I, imiprothrin (460)+COMPOUND OF FORMULA I, indoxacarb (465)+COMPOUND OF FORMULA I, iodomethane (IUPAC name) (542)+COMPOUND OF FORMULA I, IPPA-152004 (compound code)+COMPOUND OF FORMULA I, IPSP (1229)+COMPOUND OF FORMULA I, isazofos (1231)+COMPOUND OF FORMULA I, isobenzan (1232)+COMPOUND OF FORMULA I, isocarbophos (alternative name) (473)+COMPOUND OF FORMULA I, isodrin (1235)+COMPOUND OF FORMULA I, isofenphos (1236)+COMPOUND OF FORMULA I, isolane (1237)+COMPOUND OF FORMULA I, isoprocarb (472)+COMPOUND OF FORMULA I, isopropyl O-(methoxyaminothiophosphoryl)salicylate (IUPAC name) (473)+COMPOUND OF FORMULA I, isoprothiolane (474)+COMPOUND OF FORMULA I, isothioate (1244)+COMPOUND OF FORMULA I, isoxathion (480)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, juvenile hormone I (alternative name) [CCN]+COMPOUND OF FORMULA I, juvenile hormone II (alternative name) [CCN]+COMPOUND OF FORMULA I, juvenile hormone III (alternative name) [CCN]+COMPOUND OF FORMULA I, kelevan (1249)+COMPOUND OF FORMULA I, kinoprene (484)+COMPOUND OF FORMULA I, lambda-cyhalothrin (198)+COMPOUND OF FORMULA I, lead arsenate [CCN]+COMPOUND OF FORMULA I, lepimectin (CCN)+COMPOUND OF FORMULA I, leptophos (1250)+COMPOUND OF FORMULA I, lindane (430)+COMPOUND OF FORMULA I, lirimfos (1251)+COMPOUND OF FORMULA I, lufenuron (490)+COMPOUND OF FORMULA I, lythidathion (1253)+COMPOUND OF FORMULA I, m-cumenyl methylcarbamate (IUPAC name) (1014)+COMPOUND OF FORMULA I, magnesium phosphide (IUPAC name) (640)+COMPOUND OF FORMULA I, malathion (492)+COMPOUND OF FORMULA I, malonoben (1254)+COMPOUND OF FORMULA I, mazidox (1255)+COMPOUND OF FORMULA I, mecarbam (502)+COMPOUND OF FORMULA I, mecarphon (1258)+COMPOUND OF FORMULA I, menazon (1260)+COMPOUND OF FORMULA I, mephosfolan (1261)+COMPOUND OF FORMULA I, mercurous chloride (513)+COMPOUND OF FORMULA I, mesulfenfos (1263)+COMPOUND OF FORMULA I, metaflumizone (CCN)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methacrifos (1266)+COMPOUND OF FORMULA I, methamidophos (527)+COMPOUND OF FORMULA I, methanesulfonyl fluoride (IUPAC/Chemical Abstracts name) (1268)+COMPOUND OF FORMULA I, methidathion (529)+COMPOUND OF FORMULA I, methiocarb (530)+COMPOUND OF FORMULA I, methocrotophos (1273)+COMPOUND OF FORMULA I, methomyl (531)+COMPOUND OF FORMULA I, methoprene (532)+COMPOUND OF FORMULA I, methoquin-butyl (1276)+COMPOUND OF FORMULA I, methothrin (alternative name) (533)+COMPOUND OF FORMULA I, methoxychlor (534)+COMPOUND OF FORMULA I, methoxyfenozide (535)+COMPOUND OF FORMULA I, methyl bromide (537)+COMPOUND OF FORMULA I, methyl isothiocyanate (543)+COMPOUND OF FORMULA I, methylchloroform (alternative name) [CCN]+COMPOUND OF FORMULA I, methylene chloride [CCN]+COMPOUND OF FORMULA I, metofluthrin [CCN]+COMPOUND OF FORMULA I, metolcarb (550)+COMPOUND OF FORMULA I, metoxadiazone (1288)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, mirex (1294)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naftalofos (alternative name) [CCN]+COMPOUND OF FORMULA I, naled (567)+COMPOUND OF FORMULA I, naphthalene (IUPAC/Chemical Abstracts name) (1303)+COMPOUND OF FORMULA I, NC-170 (development code) (1306)+COMPOUND OF FORMULA I, NC-184 (compound code)+COMPOUND OF FORMULA I, nicotine (578)+COMPOUND OF FORMULA I, nicotine sulfate (578)+COMPOUND OF FORMULA I, nifluridide (1309)+COMPOUND OF FORMULA I, nitenpyram (579)+COMPOUND OF FORMULA I, nithiazine (1311)+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, nornicotine (traditional name) (1319)+COMPOUND OF FORMULA I, novaluron (585)+COMPOUND OF FORMULA I, noviflumuron (586)+COMPOUND OF FORMULA I, O-5-dichloro-4-iodophenyl O-ethyl ethylphosphonothioate (IUPAC name) (1057)+COMPOUND OF FORMULA I, O,O-diethyl O-4-methyl-2-oxo-2H-chromen-7-yl phosphorothioate (IUPAC name) (1074)+COMPOUND OF FORMULA I, O,O-diethyl O-6-methyl-2-propylpyrimidin-4-yl phosphorothioate (IUPAC name) (1075)+COMPOUND OF FORMULA I, O,O,O',O'-tetrapropyl dithiopyrophosphate (IUPAC name) (1424)+COMPOUND OF FORMULA I, oleic acid (IUPAC name) (593)+COMPOUND OF FORMULA I, omethoate (594)+COMPOUND OF FORMULA I, oxamyl (602)+COMPOUND OF FORMULA I, oxydemeton-methyl (609)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, para-dichlorobenzene [CCN]+COMPOUND OF FORMULA I, parathion (615)+COMPOUND OF FORMULA I, parathion-methyl (616)+COMPOUND OF FORMULA I, penfluron (alternative name) [CCN]+ COMPOUND OF FORMULA I, pentachlorophenol (623)+COMPOUND OF FORMULA I, pentachlorophenyl laurate (IUPAC name) (623)+COMPOUND OF FORMULA I, permethrin (626)+COMPOUND OF FORMULA I, petroleum oils (alternative name) (628)+COMPOUND OF FORMULA I, PH 60-38 (development code) (1328)+COMPOUND OF FORMULA I, phenkapton (1330)+COMPOUND OF FORMULA I, phenothrin (630)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosnichlor (1339)+COMPOUND OF FORMULA I, phosphamidon (639)+COMPOUND OF FORMULA I, phosphine (IUPAC name) (640)+COMPOUND OF FORMULA I, phoxim (642)+COMPOUND OF FORMULA I, phoxim-methyl (1340)+COMPOUND OF FORMULA I, pirimetaphos (1344)+COMPOUND OF FORMULA I, pirimicarb (651)+COMPOUND OF FORMULA I, pirimiphos-ethyl (1345)+COMPOUND OF FORMULA I, pirimiphos-methyl (652)+COMPOUND OF FORMULA I, polychlorodicyclopentadiene isomers (IUPAC name) (1346)+COMPOUND OF FORMULA I, polychloroterpenes (traditional name) (1347)+COMPOUND OF FORMULA I, potassium arsenite [CCN]+COMPOUND OF FORMULA I, potassium thiocyanate [CCN]+COMPOUND OF FORMULA I, prallethrin (655)+COMPOUND OF FORMULA I, precocene I (alternative name) [CCN]+COMPOUND OF FORMULA I, precocene II (alternative name) [CCN]+COMPOUND OF FORMULA I, precocene III (alternative name) [CCN]+COMPOUND OF FORMULA I, primidophos (1349)+COMPOUND OF FORMULA I, profenofos (662)+COMPOUND OF FORMULA I, profluthrin [CCN]+COMPOUND OF FORMULA I, promacyl (1354)+COMPOUND OF FORMULA I, promecarb (1355)+COMPOUND OF FORMULA I, propaphos (1356)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothiofos (686)+COMPOUND OF FORMULA I, prothoate (1362)+COMPOUND OF FORMULA I, protrifenbute [CCN]+COMPOUND OF FORMULA I, pymetrozine (688)+COMPOUND OF FORMULA I, pyraclofos (689)+COMPOUND OF FORMULA I, pyrafluprole [CCN]+COMPOUND OF FORMULA I, pyrazophos (693)+COMPOUND OF FORMULA I, pyresmethrin (1367)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridalyl (700)+COMPOUND OF FORMULA I, pyridaphenthion (701)+COMPOUND OF FORMULA I, pyrifluquinazon [CCN]+COMPOUND OF FORMULA I, pyrimidifen (706)+COMPOUND OF FORMULA I, pyrimitate (1370)+COMPOUND OF FORMULA I, pyriprole [CCN]+COMPOUND OF FORMULA I, pyriproxyfen (708)+COMPOUND OF FORMULA I, quassia (alternative name) [CCN]+COMPOUND OF FORMULA I, quinalphos (711)+COMPOUND OF FORMULA I, quinalphos-methyl (1376)+COMPOUND OF FORMULA I, quinothion (1380)+COMPOUND OF FORMULA I, quintiofos (1381)+COMPOUND OF FORMULA I, R-1492 (development code) (1382)+COMPOUND OF FORMULA I, rafoxanide (alternative name) [CCN]+COMPOUND OF FORMULA I, resmethrin (719)+COMPOUND OF FORMULA I, rotenone (722)+COMPOUND OF FORMULA I, RU 15525 (development code) (723)+COMPOUND OF FORMULA I, RU 25475 (development code) (1386)+COMPOUND OF FORMULA I, ryania (alternative name) (1387)+COMPOUND OF FORMULA I, ryanodine (traditional name) (1387)+COMPOUND OF FORMULA I, sabadilla (alternative name) (725)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, SI-0205 (compound code)+COMPOUND OF FORMULA I, SI-0404 (compound code)+COMPOUND OF FORMULA I, SI-0405 (compound code)+COMPOUND OF FORMULA I, silafluofen (728)+COMPOUND OF FORMULA I, SN 72129 (development code) (1397)+COMPOUND OF FORMULA I, sodium arsenite [CCN]+COMPOUND OF FORMULA I, sodium cyanide (444)+COMPOUND OF FORMULA I, sodium fluoride (IUPAC/Chemical Abstracts name) (1399)+COMPOUND OF FORMULA I, sodium hexafluorosilicate (1400)+COMPOUND OF FORMULA I, sodium pentachlorophenoxide (623)+COMPOUND OF FORMULA I, sodium selenate (IUPAC name) (1401)+COMPOUND OF FORMULA I, sodium thiocyanate [CCN]+COMPOUND OF FORMULA I, sophamide (1402)+COMPOUND OF FORMULA I, spinetoram [CCN]+COMPOUND OF FORMULA I, spinosad (737)+COMPOUND OF FORMULA I, spiromesifen (739)+COMPOUND OF FORMULA I, spirotetramat [CCN]+COMPOUND OF FORMULA I, sulcofuron (746)+COMPOUND OF FORMULA I, sulcofuron-sodium (746)+COMPOUND OF FORMULA I, sulfluramid (750)+COMPOUND OF FORMULA I, sulfotep (753)+COMPOUND OF FORMULA I, sulfoxaflor [CCN]+COMPOUND OF FORMULA I, sulfuryl fluoride (756)+COMPOUND OF FORMULA I, sulprofos (1408)+COMPOUND OF FORMULA I, tar oils (alternative name) (758)+COMPOUND OF FORMULA I, tau-fluvalinate (398)+COMPOUND OF FORMULA I, tazimcarb (1412)+COMPOUND OF FORMULA I, TDE (1414)+COMPOUND OF FORMULA I, tebufenozide (762)+COMPOUND OF FORMULA I, tebufenpyrad (763)+COMPOUND OF FORMULA I, tebupirimfos (764)+COMPOUND OF FORMULA I, teflubenzuron (768)+COMPOUND OF FORMULA I, tefluthrin (769)+COMPOUND OF FORMULA I, temephos (770)+COMPOUND OF FORMULA I, TEPP (1417)+COMPOUND OF FORMULA I, terallethrin (1418)+COMPOUND OF FORMULA I, terbam (alternative name)+COMPOUND OF FORMULA I, terbufos (773)+COMPOUND OF FORMULA I, tetrachloroethane [CCN]+COMPOUND OF FORMULA I, tetrachlorvinphos (777)+COMPOUND OF FORMULA I, tetramethrin (787)+COMPOUND OF FORMULA I, tetramethylfluthrin (CAS. Reg. No.: 84937-88-2)+COMPOUND OF FORMULA I, theta-cypermethrin (204)+COMPOUND OF FORMULA I, thiacloprid (791)+COMPOUND OF FORMULA I, thiafenox (alternative name)+COMPOUND OF FORMULA I, thiamethoxam (792)+COMPOUND OF FORMULA I, thicrofos (1428)+COMPOUND OF FORMULA I, thiocarboxime (1431)+COMPOUND OF FORMULA I, thiocyclam (798)+COMPOUND OF FORMULA I, thiocyclam hydrogen oxalate (798)+COMPOUND OF FORMULA I, thiodicarb (799)+COMPOUND OF FORMULA I, thiofanox (800)+COMPOUND OF FORMULA I, thiometon (801)+COMPOUND OF FORMULA I, thionazin (1434)+COMPOUND OF FORMULA I, thiosultap (803)+COMPOUND OF FORMULA I, thiosultap-sodium (803)+COMPOUND OF FORMULA I, thuringiensin (alternative name) [CCN]+COMPOUND OF FORMULA I, tolfenpyrad (809)+COMPOUND OF FORMULA I, tralomethrin (812)+COMPOUND OF FORMULA I, transfluthrin (813)+COMPOUND OF FORMULA I, transpermethrin (1440)+COMPOUND OF FORMULA I, triamiphos (1441)+COMPOUND OF FORMULA I, triazamate (818)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trichlormetaphos-3 (alternative name) [CCN]+COMPOUND OF FORMULA I, trichloronat (1452)+COMPOUND OF FORMULA I, trifenofos (1455)+COMPOUND OF FORMULA I, triflumuron (835)+COMPOUND OF FORMULA I, trimethacarb (840)+COMPOUND OF FORMULA I, triprene (1459)+COMPOUND OF FORMULA I, vamidothion (847)+COMPOUND OF FORMULA I, vaniliprole [CCN]+COMPOUND OF FORMULA I, veratridine (alternative name) (725)+COMPOUND OF FORMULA I, veratrine (alternative name) (725)+COMPOUND OF FORMULA I, XMC (853)+COMPOUND OF FORMULA I, xylylcarb (854)+COMPOUND OF FORMULA I, YI-5302 (compound code)+COMPOUND OF FORMULA I, zeta-cypermethrin (205)+COMPOUND OF FORMULA I, zetamethrin (alternative name)+COMPOUND OF FORMULA I, zinc phosphide (640)+COMPOUND OF FORMULA I, zolaprofos (1469), ZJ0967 (development code)+COMPOUND OF FORMULA I, ZJ3757 (development code)+COMPOUND OF FORMULA I, and ZXI 8901 (development code) (858)+COMPOUND OF FORMULA I, a molluscicide selected from the group of substances consisting of bis(tributyltin) oxide (IUPAC name) (913)+COMPOUND OF FORMULA I, bromoacetamide [CCN]+COMPOUND OF FORMULA I, calcium arsenate [CCN]+COMPOUND OF FORMULA I, cloethocarb (999)+COMPOUND OF FORMULA I, copper acetoarsenite [CCN]+COMPOUND OF FORMULA I, copper sulfate (172)+COMPOUND OF FORMULA I, fentin (347)+COMPOUND OF FORMULA I, ferric phosphate (IUPAC name) (352)+COMPOUND OF FORMULA I, metaldehyde (518)+COMPOUND OF FORMULA I, methiocarb (530)+COMPOUND OF FORMULA I, niclosamide (576)+COMPOUND OF FORMULA I, niclosamide-olamine (576)+COMPOUND OF FORMULA I, pentachlorophenol (623)+COMPOUND OF FORMULA I, sodium pentachlorophenoxide (623)+COMPOUND OF FORMULA I, tazimcarb (1412)+COMPOUND OF FORMULA I, thiodicarb (799)+COMPOUND OF FORMULA I, tralopyril [CCN]+COMPOUND OF FORMULA I, tributyltin oxide (913)+COMPOUND OF FORMULA I, trifenmorph (1454)+COMPOUND OF FORMULA I, trimethacarb (840)+COMPOUND OF FORMULA I, triphenyltin acetate (IUPAC name) (347) and triphenyltin hydroxide (IUPAC name) (347)+COMPOUND OF FORMULA I, a nematicide selected from the group of substances consisting of AKD-3088 (compound code)+COMPOUND OF FORMULA I, 1,2-dibromo-3-chloropropane (IUPAC/Chemical Abstracts name) (1045)+COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1,3-dichloropropene (233)+COMPOUND OF FORMULA I, 3,4-dichlorotetrahydrothiophene 1,1-dioxide (IUPAC/Chemical Abstracts name) (1065)+COMPOUND OF FORMULA I, 3-(4-chlorophenyl)-5-methylrhodanine (IUPAC name) (980)+COMPOUND OF FORMULA I, 5-methyl-6-thioxo-1,3,5-thiadiazinan-3-ylacetic acid (IUPAC name) (1286)+COMPOUND OF FORMULA I, 6-isopentenylaminopurine (alternative name) (210)+COMPOUND OF FORMULA I, abamectin (1)+COMPOUND OF FORMULA I, acetoprole [CCN]+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, AZ 60541 (compound code)+COMPOUND OF FORMULA I, benclothiaz [CCN]+COMPOUND OF FORMULA I, benomyl (62)+COMPOUND OF FORMULA I, butylpyridaben (alternative name)+COMPOUND OF FORMULA I, cadusafos (109)+COMPOUND OF FORMULA I, carbofuran (118)+COMPOUND OF FORMULA I, carbon disulfide (945)+COMPOUND OF FORMULA I, carbosulfan (119)+COMPOUND OF FORMULA I, chloropicrin (141)+COMPOUND OF FORMULA I, chlorpyrifos (145)+COMPOUND OF FORMULA I, cloethocarb (999)+COMPOUND OF FORMULA I, cytokinins (alternative name) (210)+COMPOUND OF FORMULA I, dazomet (216)+COMPOUND OF FORMULA I, DBCP (1045)+COMPOUND OF FORMULA I, DCIP (218)+COMPOUND OF FORMULA I, diamidafos (1044)+COMPOUND OF FORMULA I, dichlofenthion (1051)+COMPOUND OF FORMULA I, dicliphos (alternative name)+COMPOUND OF FORMULA I, dimethoate (262)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ethoprophos (312)+COMPOUND OF FORMULA I, ethylene dibromide (316)+COMPOUND OF FORMULA I, fenamiphos (326)+COMPOUND OF FORMULA I, fenpyrad (alternative name)+COMPOUND OF FORMULA I, fensulfothion (1158)+COMPOUND OF FORMULA I, fluensulfone (CAS. Reg. No.: 318290-98-1)+COMPOUND OF FORMULA I, fosthiazate (408)+COMPOUND OF FORMULA I, fosthietan (1196)+COMPOUND OF FORMULA I, furfural (alternative name) [CCN]+COMPOUND OF FORMULA I, GY-81 (development code) (423)+COMPOUND OF FORMULA I, heterophos [CCN]+COMPOUND OF FORMULA I, imicyafos [CCN]+COMPOUND OF FORMULA I, imicyafos (alternative name) [CCN]+COMPOUND OF FORMULA I, iodomethane (IUPAC name) (542)+COMPOUND OF FORMULA I, isamidofos (1230)+COMPOUND OF FORMULA I, isazofos (1231)+COMPOUND OF FORMULA I, ivermectin (alternative name) [CCN]+COMPOUND OF FORMULA I, kinetin (alternative name) (210)+COMPOUND OF FORMULA I, mecarphon (1258)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methyl bromide (537)+COMPOUND OF FORMULA I, methyl isothiocyanate (543)+COMPOUND OF FORMULA I, milbemycin oxime (alternative name) [CCN]+COMPOUND OF FORMULA I, moxidectin (alternative name) [CCN]+COMPOUND OF FORMULA I, Myrothecium verrucaria composition (alternative name) (565)+COMPOUND OF FORMULA I, NC-184 (compound code)+COMPOUND OF FORMULA I, oxamyl (602)+COMPOUND OF FORMULA I, phorate (636)+COMPOUND OF FORMULA I, phosphamidon (639)+COMPOUND OF FORMULA I, phosphocarb [CCN]+COMPOUND OF FORMULA I, sebufos (alternative name)+COMPOUND OF FORMULA I, selamectin (alternative name) [CCN]+COMPOUND OF FORMULA I, spinosad (737)+COMPOUND OF FORMULA I, terbam (alternative name)+COMPOUND OF FORMULA I, terbufos (773)+COMPOUND OF FORMULA I, tetrachlorothiophene (IUPAC/Chemical Abstracts name) (1422)+COMPOUND OF FORMULA I, thiafenox (alternative name)+COMPOUND OF FORMULA I, thionazin (1434)+COMPOUND OF FORMULA I, triazophos (820)+COMPOUND OF FORMULA I, triazuron (alternative name)+COMPOUND OF FORMULA I, xylenols [CCN]+COMPOUND OF FORMULA I, YI-5302 (compound code) and zeatin (alternative name) (210)+COMPOUND OF FORMULA I, a nitrification inhibitor selected from the group of substances consisting of potassium ethylxanthate [CCN] and nitrapyrin (580)+COMPOUND OF FORMULA I, a plant activator selected from the group of substances consisting of acibenzolar (6)+COMPOUND OF FORMULA I, acibenzolar-S-methyl (6)+COMPOUND OF FORMULA I, probenazole (658) and *Reynoutria sachalinensis* extract (alternative name) (720)+COMPOUND OF FORMULA I, a rodenticide selected from the group of substances consisting of 2-isovalerylindan-1,3-dione (IUPAC name) (1246)+COMPOUND OF FORMULA I, 4-(quinoxalin-2-ylamino)benzenesulfonamide (IUPAC name) (748)+COMPOUND OF FORMULA I, alpha-chlorohydrin [CCN]+COMPOUND OF FORMULA I, aluminium phosphide (640)+COMPOUND OF FORMULA I, antu (880)+COMPOUND OF FORMULA I, arsenous oxide (882)+COMPOUND OF FORMULA I, barium carbonate (891)+COMPOUND OF FORMULA I, bisthiosemi (912)+COMPOUND OF FORMULA I, brodifacoum (89)+COMPOUND OF FORMULA I, bromadiolone (91)+COMPOUND OF FORMULA I, bromethalin (92)+COMPOUND OF FORMULA I, calcium cyanide (444)+COMPOUND OF FORMULA I, chloralose (127)+COMPOUND OF FORMULA I, chlorophacinone (140)+COMPOUND OF FORMULA I, cholecalciferol (alternative name) (850)+COMPOUND OF FORMULA I, colecalciferol+COMPOUND OF FORMULA I, coumachlor (1004)+COMPOUND OF FORMULA I, coumafuryl (1005)+COMPOUND OF FORMULA I, coumatetralyl (175)+COMPOUND OF FORMULA I, crimidine (1009)+COMPOUND OF FORMULA I, difenacoum (246)+COMPOUND OF FORMULA I, difethialone (249)+COMPOUND OF FORMULA I, diphacinone (273)+COMPOUND OF FORMULA I, ergocalciferol (301)+COMPOUND OF FORMULA I, flocoumafen (357)+COMPOUND OF FORMULA I, fluoroacetamide (379)+COMPOUND OF FORMULA I, flupropadine (1183)+COMPOUND OF FORMULA I, flupropadine hydrochloride (1183)+COMPOUND OF FORMULA I, gamma-HCH (430)+COMPOUND OF FORMULA I, HCH (430)+COMPOUND OF FORMULA I, hydrogen cyanide (444)+COMPOUND OF FORMULA I, iodomethane (IUPAC name) (542)+COMPOUND OF FORMULA I, lindane (430)+COMPOUND OF FORMULA I, magnesium phosphide (IUPAC name) (640)+COMPOUND OF FORMULA I, methyl bromide (537)+COMPOUND OF FORMULA I, norbormide (1318)+COMPOUND OF FORMULA I, phosacetim (1336)+COMPOUND OF FORMULA I, phosphine (IUPAC name) (640)+COMPOUND OF FORMULA I, phosphorus [CCN]+COMPOUND OF FORMULA I, pindone (1341)+COMPOUND OF FORMULA I, potassium arsenite [CCN]+COMPOUND OF FORMULA I, pyrinuron (1371)+COMPOUND OF FORMULA I, scilliroside (1390)+COMPOUND OF FORMULA I, sodium arsenite [CCN]+COMPOUND OF FORMULA I, sodium cyanide (444)+COMPOUND OF FORMULA I, sodium fluoroacetate (735)+COMPOUND OF FORMULA I, strychnine (745)+COMPOUND OF FORMULA I, thallium sulfate [CCN]+COMPOUND OF FORMULA I, warfarin (851) and zinc phosphide (640)+COMPOUND OF FORMULA I, a synergist selected from the group of substances consisting of 2-(2-butoxyethoxy)-ethyl piperonylate (IUPAC name) (934)+COMPOUND OF FORMULA I, 5-(1,3-benzodioxol-5-yl)-3-hexylcyclohex-2-enone (IUPAC name) (903)+COMPOUND OF FORMULA I, farnesol with nerolidol (alternative name) (324)+COMPOUND OF FORMULA I, MB-599 (development code) (498)+COMPOUND OF FORMULA I, MGK 264 (development code) (296)+COMPOUND OF FORMULA I, piperonyl butoxide (649)+COMPOUND OF FORMULA I, piprotal (1343)+COMPOUND OF FORMULA I, propyl isomer (1358)+COMPOUND OF FORMULA I, S421 (development code) (724)+COMPOUND OF FORMULA I, sesamex (1393)+COMPOUND OF FORMULA I, sesasmolin (1394) and sulfoxide (1406)+COMPOUND OF FORMULA I, an animal repellent selected from the group of substances consisting of anthraquinone (32)+COMPOUND OF FORMULA I, chloralose (127)+COMPOUND OF FORMULA I, copper naphthenate [CCN]+COMPOUND OF FORMULA I, copper oxychloride (171)+COMPOUND OF FORMULA I, diazinon (227)+COMPOUND OF FORMULA I, dicyclopentadiene (chemical name) (1069)+COMPOUND OF FORMULA I, guazatine (422)+COMPOUND OF FORMULA I, guazatine acetates (422)+COMPOUND OF FORMULA I, methiocarb (530)+COMPOUND OF FORMULA I, pyridin-4-amine (IUPAC name) (23)+COMPOUND OF FORMULA I, thiram (804)+COMPOUND OF FORMULA I, trimethacarb (840)+COMPOUND OF FORMULA I, zinc naphthenate [CCN] and ziram (856)+COMPOUND OF FORMULA I, a virucide selected from the group of substances consisting of imanin (alternative name) [CCN] and ribavirin (alternative name) [CCN]+COMPOUND OF FORMULA I,
a wound protectant selected from the group of substances consisting of mercuric oxide (512)+COMPOUND OF FORMULA I, octhilinone (590) and thiophanate-methyl (802)+COMPOUND OF FORMULA I,
an insecticide selected from the group consisting of the compound of the formula A-1

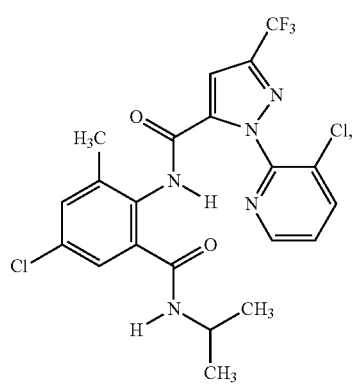

(A-1) + COMPOUND OF FORMULA I the formula A-2

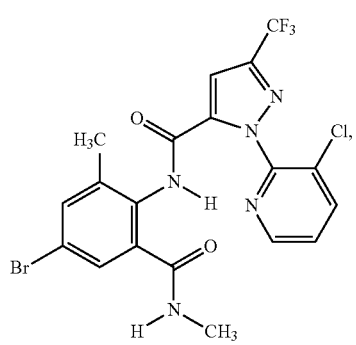

(A-2) + COMPOUND OF FORMULA I the formula A-3

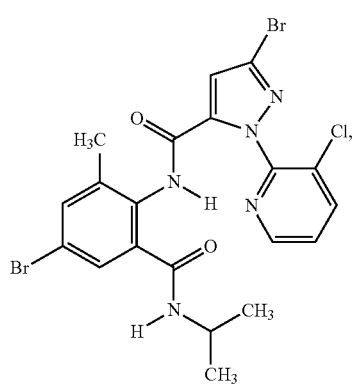

(A-3) + COMPOUND OF FORMULA I the formula A-4

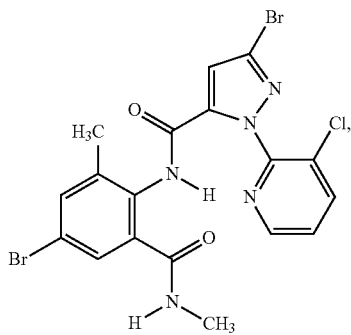

(A-4) + COMPOUND OF FORMULA I the formula A-5

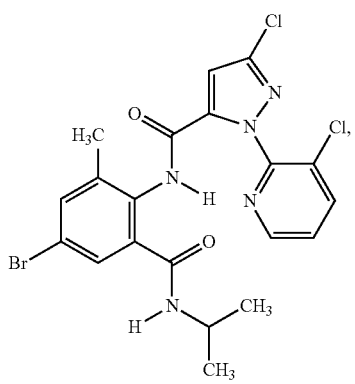

(A-5) + COMPOUND OF FORMULA I the formula A-6

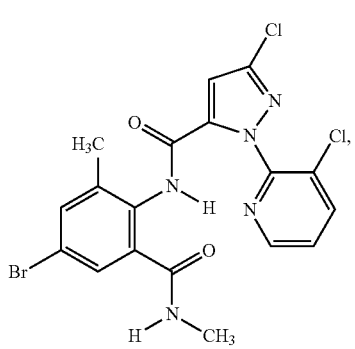

(A-6) + COMPOUND OF FORMULA I the formula A-7
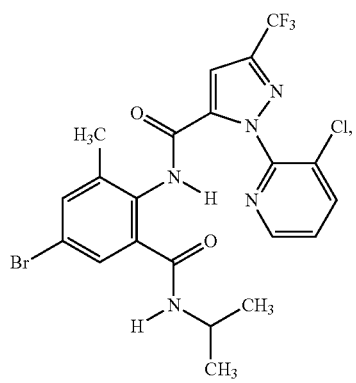
(A-7) + COMPOUND OF FORMULA I
the formula A-8
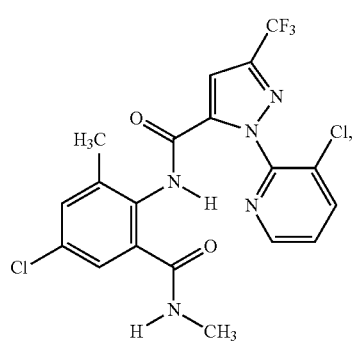
(A-8) + COMPOUND OF FORMULA I
the formula A-9
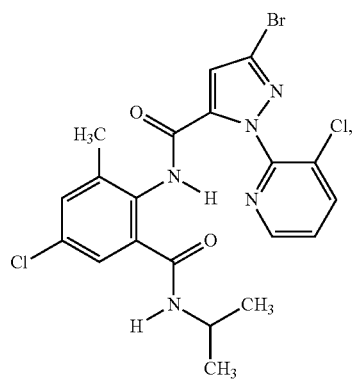
(A-9) + COMPOUND OF FORMULA I
the formula A-10
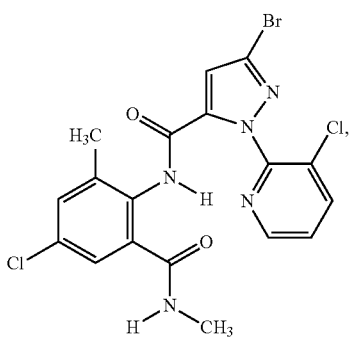
(A-10) + COMPOUND OF FORMULA I
the formula A-11
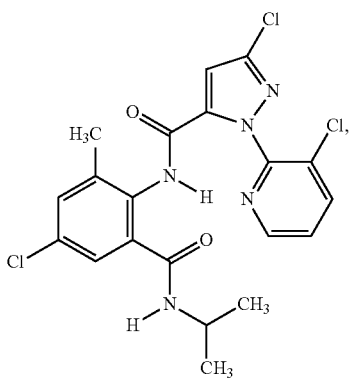
(A-11) + COMPOUND OF FORMULA I
the formula A-12
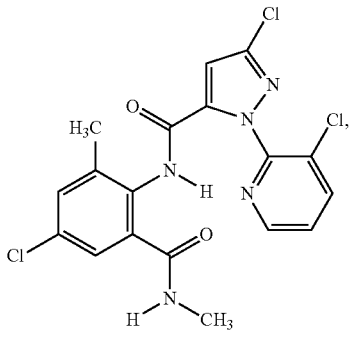
(A-12) + COMPOUND OF FORMULA I the formula A-13
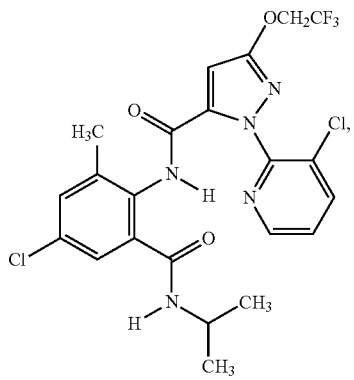
(A-13) + COMPOUND OF FORMULA I
the formula A-14
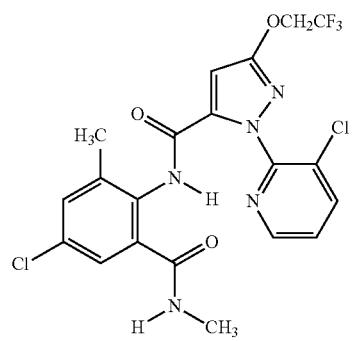 
(A-14)  + COMPOUND OF FORMULA I,
the formula A-15
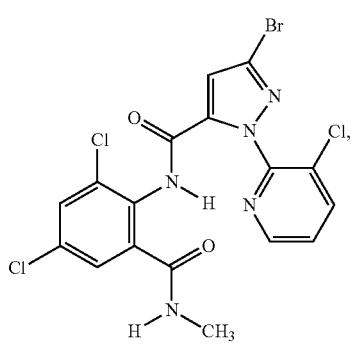
(A-15) + COMPOUND OF FORMULA I
the formula A-16
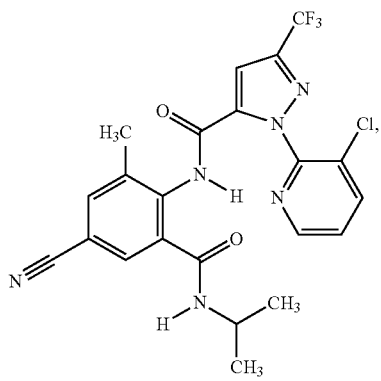
(A-16) + COMPOUND OF FORMULA I
the formula A-17
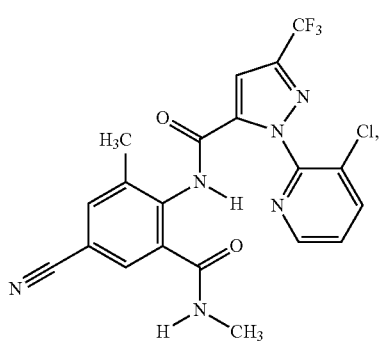
(A-17) + COMPOUND OF FORMULA I
the formula A-18
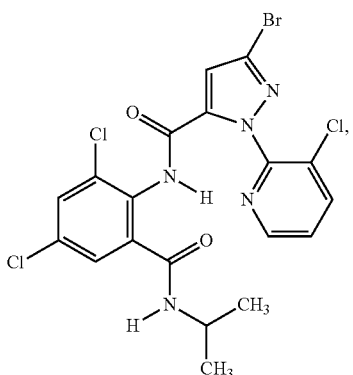
(A-18) + COMPOUND OF FORMULA I the formula A-19
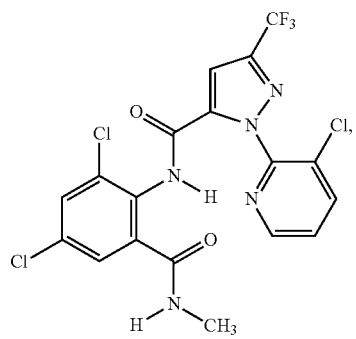
(A-19) + COMPOUND OF FORMULA I
the formula A-20
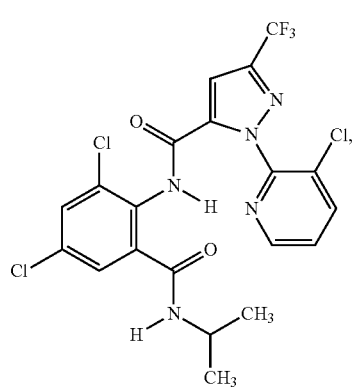
(A-20) + COMPOUND OF FORMULA I
the formula A-21
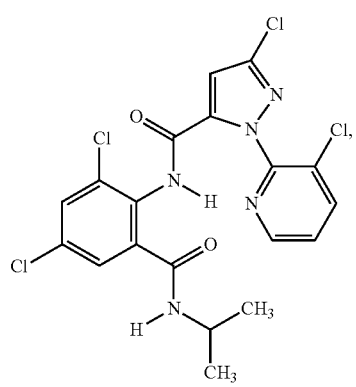
(A-21) + COMPOUND OF FORMULA I
the formula A-22
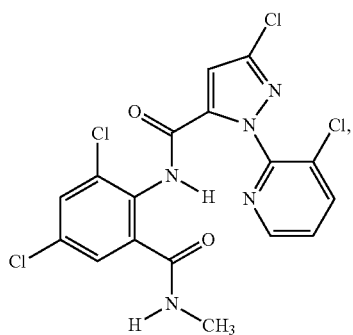
(A-22) + COMPOUND OF FORMULA I
the formula A-23
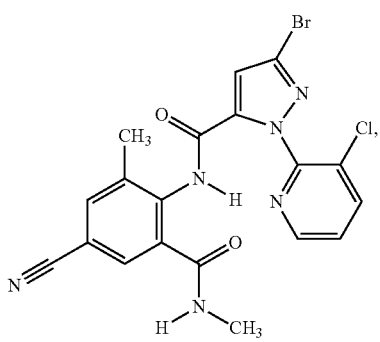
(A-23) + COMPOUND OF FORMULA I
the formula A-24
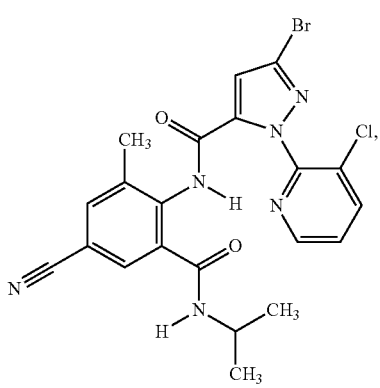
(A-24) + COMPOUND OF FORMULA I the formula A-25

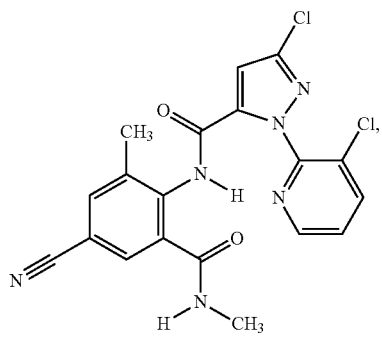

(A-25) + COMPOUND OF FORMULA I the formula A-26

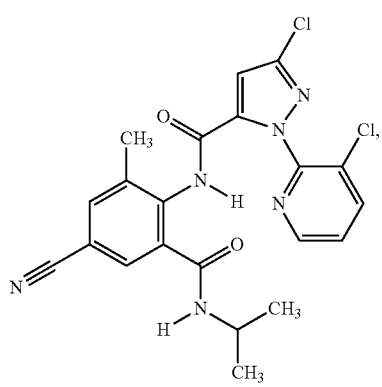

(A-26) + COMPOUND OF FORMULA I and the formula A-27

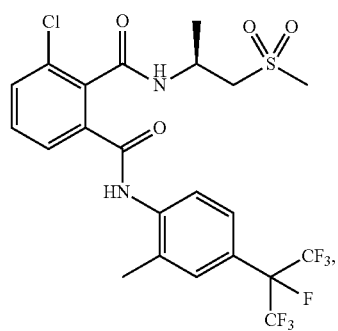

(A-27) + COMPOUND OF FORMULA I an insecticide selected from the group consisting of the compound of the formula A-28

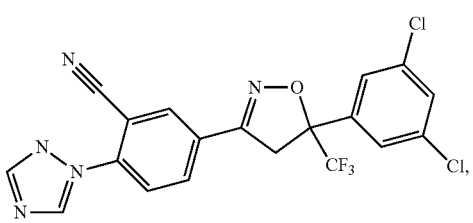

(A-28) + COMPOUND OF FORMULA I and the formula A-29

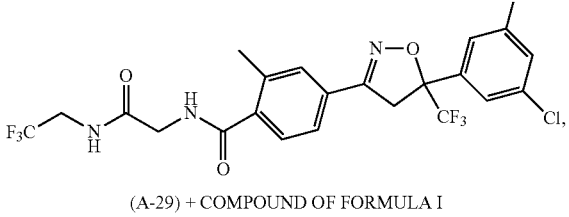

(A-29) + COMPOUND OF FORMULA I and the formula A-30

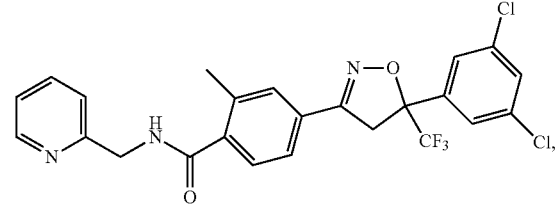

(A-30) + COMPOUND OF FORMULA I an insecticide selected from the group consisting of the compound of the formula A-31 [BYI2960 (development code)]

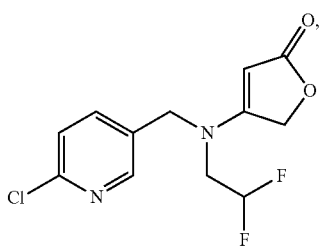

(A-31) + COMPOUND OF FORMULA I the formula A-32

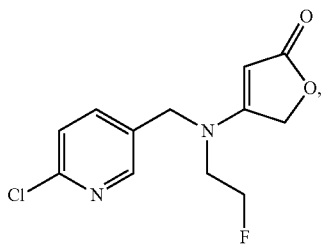

(A-32) + COMPOUND OF FORMULA I the formula A-33

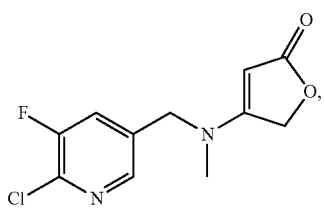

(A-33) + COMPOUND OF FORMULA I and an insecticide of the formula A-34 [SYN 876 (compound code)]

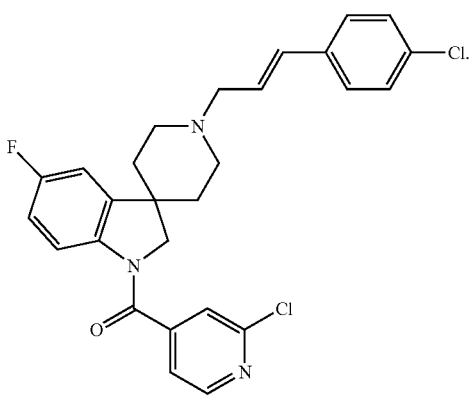

(A-34) + COMPOUND OF FORMULA I

The references in brackets behind the active ingredients, e.g. [3878-19-1] refer to the Chemical Abstracts Registry number. The compounds of the formula A-1 to A-26 are described in WO 03/015518 or in WO 04/067528. The compound of the formula A-27 is described in WO 06/022225 and in WO 07/112844. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The compounds of formula I according to the invention can also be used in combination with one or more fungicides. In particular, in the following mixtures of the compounds of formula I with fungicides, the term COMPOUND OF FORMULA I preferably refers to a compound selected from one of the Tables 1 to 16:

COMPOUND OF FORMULA I+(E)-N-methyl-2-[2-(2,5-dimethylphenoxymethyl)phenyl]-2-methoxy-iminoacetamide (SSF-129), COMPOUND OF FORMULA I+4-bromo-2-cyano-N,N-dimethyl-6-trifluoromethylbenzimidazole-1-sulphonamide, COMPOUND OF FORMULA I+α-[N-(3-chloro-2,6-xylyl)-2-methoxyacetamido]-γ-butyrolactone, COMPOUND OF FORMULA I+4-chloro-2-cyano-N,N-dimethyl-5-p-tolylimidazole-1-sulfonamide (IKF-916, cyamidazosulfamid), COMPOUND OF FORMULA I+3-5-dichloro-N-(3-chloro-1-ethyl-1-methyl-2-oxopropyl)-4-methylbenzamide (RH-7281, zoxamide), COMPOUND OF FORMULA I+N-allyl-4,5,-dimethyl-2-trimethylsilylthiophene-3-carboxamide (MON65500), COMPOUND OF FORMULA I+N-(1-cyano-1,2-dimethylpropyl)-2-(2,4-dichlorophenoxy)propionamide (AC382042), COMPOUND OF FORMULA I+N-(2-methoxy-5-pyridyl)-cyclopropane carboxamide, COMPOUND OF FORMULA I+acibenzolar, COMPOUND OF FORMULA I+alanycarb, COMPOUND OF FORMULA I+aldimorph, COMPOUND OF FORMULA I+ametoctradin, COMPOUND OF FORMULA I+amisulbrom, COMPOUND OF FORMULA I+anilazine, COMPOUND OF FORMULA I+azaconazole, COMPOUND OF FORMULA I+azoxystrobin, COMPOUND OF FORMULA I+benalaxyl, COMPOUND OF FORMULA I+benalaxyl-M, COMPOUND OF FORMULA I+benomyl, COMPOUND OF FORMULA I+benthiavalicarb, COMPOUND OF FORMULA I+benzodiflupyr, COMPOUND OF FORMULA I+benzovindiflupyr, COMPOUND OF FORMULA I+biloxazol, COMPOUND OF FORMULA I+bitertanol, COMPOUND OF FORMULA I+bixafen, COMPOUND OF FORMULA I+blasticidin S, COMPOUND OF FORMULA I+boscalid, COMPOUND OF FORMULA I+bromuconazole, COMPOUND OF FORMULA I+bupirimate, COMPOUND OF FORMULA I+captafol, COMPOUND OF FORMULA I+captan, COMPOUND OF FORMULA I+carbendazim, COMPOUND OF FORMULA I+carbendazim chlorhydrate, COMPOUND OF FORMULA I+carboxin, COMPOUND OF FORMULA I+carpropamid, carvone, COMPOUND OF FORMULA I+CGA41396, COMPOUND OF FORMULA I+CGA41397, COMPOUND OF FORMULA I+chinomethionate, COMPOUND OF FORMULA I+chlazafenone, COMPOUND OF FORMULA I+chlorodincarb, COMPOUND OF FORMULA I+chlorothalonil, COMPOUND OF FORMULA I+chlorozolinate, COMPOUND OF FORMULA I+clozylacon, COMPOUND OF FORMULA I+copper containing compounds such as copper oxychloride, copper oxyquinolate, copper sulphate, copper tallate and Bordeaux mixture, COMPOUND OF FORMULA I+coumoxystrobin, COMPOUND OF FORMULA I+cyazofamid, COMPOUND OF FORMULA I+cyflufenamid, COMPOUND OF FORMULA I+cymoxanil, COMPOUND OF FORMULA I+cyproconazole, COMPOUND OF FORMULA I+cyprodinil, COMPOUND OF FORMULA I+debacarb, COMPOUND OF FORMULA I+di-2-pyridyl disulphide 1,1'-dioxide, COMPOUND OF FORMULA I+dicloaminostrobin, COMPOUND OF FORMULA I+diclofenoxystrobin, COMPOUND OF FORMULA I+dichlofluanid, COMPOUND OF FORMULA I+diclomezine, COMPOUND OF FORMULA I+dicloran, COMPOUND OF FORMULA I+diethofencarb, COMPOUND OF FORMULA I+difenoconazole, COMPOUND OF FORMULA I+difenzoquat, COMPOUND OF FORMULA I+diflumetorim, COMPOUND OF FORMULA I+O,O-di-iso-propyl-S-benzyl thiophosphate, COMPOUND OF FORMULA I+dimefluazole, COMPOUND OF FORMULA I+dimetconazole, COMPOUND OF FORMULA I+dimethomorph, COMPOUND OF FORMULA I+dimethirimol, COMPOUND OF FORMULA I+dimoxystrobin, COMPOUND OF FORMULA I+diniconazole, COMPOUND OF FORMULA I+dinocap, COMPOUND OF FORMULA I+dithianon, COMPOUND OF FORMULA I+dodecyl dimethyl ammonium chloride, COMPOUND OF FORMULA I+dodemorph, COMPOUND OF FORMULA I+dodine, COMPOUND OF FORMULA I+doguadine, COMPOUND OF FORMULA I+edifenphos, COMPOUND OF FORMULA I+enoxastrobin, COMPOUND OF FORMULA I+epoxiconazole, COMPOUND OF FORMULA I+ethirimol, COMPOUND OF FORMULA I+ethyl(Z)—N-benzyl-N([methyl(methyl-thioethylideneaminooxycarbonyl)amino]thio)-β-alaninate, COMPOUND OF FORMULA I+etridiazole, COMPOUND OF FORMULA I+famoxadone, COMPOUND OF FORMULA I+fenamidone (RPA407213), COMPOUND OF FORMULA I+fenaminstrobin, COMPOUND OF FORMULA I+fenarimol, COMPOUND OF FORMULA I+fenbuconazole, COMPOUND OF FORMULA I+fenfuram, COMPOUND OF FORMULA I+fenhexamid (KBR2738), COMPOUND OF FORMULA I+fenoxanil, COMPOUND OF FORMULA I+fenoxystrobin, COMPOUND OF FORMULA I+fenpiclonil, COMPOUND OF FORMULA I+fenpropidin, COMPOUND OF FORMULA I+fenpropimorph, COMPOUND OF FORMULA I+fenpyrazamine, COMPOUND OF FORMULA I+fenpyrazamine/ipfenpyrazolone, COMPOUND OF FORMULA I+fentin acetate, COMPOUND OF FORMULA I+fentin hydroxide, COMPOUND OF FORMULA I+ferbam, COMPOUND OF FORMULA I+ferimzone, COMPOUND OF FORMULA I+fluazinam, COMPOUND OF FORMULA I+fludioxonil, COMPOUND OF FORMULA I+flufenoxystrobin, COMPOUND OF FORMULA I+flumetover, COMPOUND OF FORMULA I+flumorph, COMPOUND OF FORMULA I+fluopicolide, COMPOUND OF FORMULA I+fluopyram, COMPOUND OF FORMULA I+fluoxastrobin, COMPOUND OF FORMULA I+fluoroimide, COMPOUND OF FORMULA I+fluquinconazole, COMPOUND OF FORMULA I+flusilazole, COMPOUND OF FORMULA I+flutianil, COMPOUND OF FORMULA I+flutolanil, COMPOUND OF FORMULA I+flutriafol, COMPOUND OF FORMULA I+fluxapyroxad, COMPOUND OF FORMULA I+folpet, COMPOUND OF FORMULA I+fosetyl, COMPOUND OF FORMULA I+fosetyl-aluminium, COMPOUND OF FORMULA I+fuberidazole, COMPOUND OF FORMULA I+furalaxyl, COMPOUND OF FORMULA I+furametpyr, COMPOUND OF FORMULA I+guazatine, COMPOUND OF FORMULA I+hexaconazole, COMPOUND OF FORMULA I+hydroxyisoxazole, COMPOUND OF FORMULA I+hymexazole, COMPOUND OF FORMULA I+imazalil, COMPOUND OF FORMULA I+imibenconazole, COMPOUND OF FORMULA I+iminoctadine, COMPOUND OF FORMULA I+iminoctadine triacetate, COMPOUND OF FORMULA I+ipconazole, COMPOUND OF FORMULA I+iprobenfos, COMPOUND OF FORMULA I+iprodione, COMPOUND OF FORMULA I+iprovalicarb (SZX0722), COMPOUND OF FORMULA I+isofetamid, COMPOUND OF FORMULA I+isopropanyl butyl carbamate, COMPOUND OF FORMULA I+isoprothiolane, COMPOUND OF FORMULA I+isopyrazam, COMPOUND OF FORMULA I+isotianil, COMPOUND OF FORMULA I+kasugamycin, COMPOUND OF FORMULA I+kresoxim-methyl, COMPOUND OF FORMULA I+LY186054, COMPOUND OF FORMULA I+LY211795, COMPOUND OF FORMULA I+LY248908, COMPOUND OF FORMULA I+mancozeb, COMPOUND OF FORMULA I+mandipropamid, COMPOUND OF FORMULA I+maneb, COMPOUND OF FORMULA I+mefenoxam, COMPOUND OF FORMULA I+mepanipyrim, COMPOUND OF FORMULA I+mepronil, COMPOUND OF FORMULA I+meptyldinocap, COMPOUND OF FORMULA I+metalaxyl, COMPOUND OF FORMULA I+metconazole, COMPOUND OF FORMULA I+metiram, COMPOUND OF FORMULA I+metiram-zinc, COMPOUND OF FORMULA I+metominostrobin, COMPOUND OF FORMULA I+metrafenone, COMPOUND OF FORMULA I+myclobutanil, COMPOUND OF FORMULA I+neoasozin, COMPOUND OF FORMULA I+nickel dimethyldithiocarbamate, COMPOUND OF FORMULA I+nicobifen, COMPOUND OF FORMULA I+nitrothal-isopropyl, COMPOUND OF FORMULA I+nuarimol, COMPOUND OF FORMULA I+ofurace, COMPOUND OF FORMULA I+organomercury compounds, COMPOUND OF FORMULA I+orysastrobin, COMPOUND OF FORMULA I+oxadixyl, COMPOUND OF FORMULA I+oxasulfuron, COMPOUND OF FORMULA I+oxolinic acid, COMPOUND OF FORMULA I+oxpoconazole, COMPOUND OF FORMULA I+oxycarboxin, COMPOUND OF FORMULA I+pefurazoate, COMPOUND OF FORMULA I+penconazole, COMPOUND OF FORMULA I+pencycuron, COMPOUND OF FORMULA I+penflufen, COMPOUND OF FORMULA I+penthiopyrad, COMPOUND OF FORMULA I+phenazin oxide, COMPOUND OF FORMULA I+phosetyl-AI, COMPOUND OF FORMULA I+phosphorus acids, COMPOUND OF FORMULA I+phthalide, COMPOUND OF FORMULA I+picoxystrobin (ZA1963), COMPOUND OF FORMULA I+polyoxin D, COMPOUND OF FORMULA I+polyram, COMPOUND OF FORMULA I+probenazole, COMPOUND OF FORMULA I+prochloraz, COMPOUND OF FORMULA I+procymidone, COMPOUND OF FORMULA I+propamocarb, COMPOUND OF FORMULA I+prop-iconazole, COMPOUND OF FORMULA I+propineb, COMPOUND OF FORMULA I+propionic acid, COMPOUND OF FORMULA I+proquinazid, COMPOUND OF FORMULA I+prothioconazole, COMPOUND OF FORMULA I+pyraclostrobin, COMPOUND OF FORMULA I+pyraoxystrobin, COMPOUND OF FORMULA I+pyrazophos, COMPOUND OF FORMULA I+pyribencarb, COMPOUND OF FORMULA I+pyrifenox, COMPOUND OF FORMULA I+pyrimethanil, COMPOUND OF FORMULA I+pyrisoxazole, COMPOUND OF FORMULA I+pyroquilon, COMPOUND OF FORMULA I+pyroxyfur, COMPOUND OF FORMULA I+pyrrolnitrin, COMPOUND OF FORMULA I+quaternary ammonium compounds, COMPOUND OF FORMULA I+quinomethionate, COMPOUND OF FORMULA I+quinoxyfen, COMPOUND OF FORMULA I+quintozene, COMPOUND OF FORMULA I+sedaxane, COMPOUND OF FORMULA I+sipconazole (F-155), COMPOUND OF FORMULA I+sodium pentachlorophenate, COMPOUND OF FORMULA I+spiroxamine, COMPOUND OF FORMULA I+streptomycin, COMPOUND OF FORMULA I+sulphur, COMPOUND OF FORMULA I+tebuconazole, COMPOUND OF FORMULA I+tecloftalam, COMPOUND OF FORMULA I+tecnazene, COMPOUND OF FORMULA I+terbufloquin, COMPOUND OF FORMULA I+tetraconazole, COMPOUND OF FORMULA I+thiabendazole, COMPOUND OF FORMULA I+thifluzamid, COMPOUND OF FORMULA I+2-(thiocyanomethylthio)benzothiazole, COMPOUND OF FORMULA I+thiophanate-methyl, COMPOUND OF FORMULA I+thiram, COMPOUND OF FORMULA I+tiadinil, COMPOUND OF FORMULA I+timibenconazole, COMPOUND OF FORMULA I+tolclofos-methyl, COMPOUND OF FORMULA I+tolprocarb, COMPOUND OF FORMULA I+tolylfluanid, COMPOUND OF FORMULA I+triadimefon, COMPOUND OF FORMULA I+triadimenol, COMPOUND OF FORMULA I+triazbutil, COMPOUND OF FORMULA I+triazoxide, COMPOUND OF FORMULA I+triclopyricarb, COMPOUND OF FORMULA I+tricyclazole, COMPOUND OF FORMULA I+tridemorph, COMPOUND OF FORMULA I+trifloxystrobin, COMPOUND OF FORMULA I+triforine, COMPOUND OF FORMULA I+triflumizole, COMPOUND OF FORMULA I+triticonazole, COMPOUND OF FORMULA I+validamycin A, COMPOUND OF FORMULA I+valiphenal, COMPOUND OF FORMULA I+vapam, COMPOUND OF FORMULA I+vinclozolin, COMPOUND OF FORMULA I+zineb and COMPOUND OF FORMULA I+ziram.

The compounds of formula I may be mixed with soil, peat or other rooting media for the protection of plants against seed-borne, soil-borne or foliar fungal diseases.

The compounds of formula I according to the invention can also be used in combination with one or more other synergists. In particular, the following mixtures of the COMPOUND OF FORMULA I, where this term preferably refers to a compound selected from one of the Tables 1 to 16, are important:

COMPOUND OF FORMULA I+piperonyl butoxide, COMPOUND OF FORMULA I+sesamex, COMPOUND OF FORMULA I+safroxan and COMPOUND OF FORMULA I+dodecyl imidazole.

The compounds of formula I according to the invention can also be used in combination with one or more other herbicides. In particular, the following mixtures of the COMPOUND OF FORMULA I, where this term preferably refers to a compound selected from one of the Tables 1 to 16, are important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminocyclopyrachlor, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bicyclopyrone, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clacyfos, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+indaziflam, compound of formula I+iodomethane, compound of formula I+iodosulfuron, compound of formula I+iodosulfuron-methyl-sodium, compound of formula I+iofensulfuron, compound of formula I+ioxynil, compound of formula I+isoproturon, compound of formula I+ipfencarbazone, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazasulfuron, compound of formula I+methabenzthiazuron, compound of formula I+methylarsonic acid, compound of formula I+methyldymron, compound of formula I+methyl isothiocyanate, compound of formula I+metiozolin, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrasulfutole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+pyroxsulam, compound of formula I+pyroxasulfone, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+saflufenacil, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thiencarbazone, compound of formula I+thiencarbazone-methyl, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+triafamone, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one, compound of formula I+N-[2-[(4,6-dimethoxy-1,3,5-triazin-2-yl)carbonyl]-6-fluorophenyl]-1,1-difluoro-N-methylmethanesulfonamide (CAS RN 874195-61-6), compound of formula I+N-[(1R,2S)-2,6-dimethyl-2,3-dihydro-1H-inden-1-yl]-6-(1-fluoroethyl)-1,3,5-triazine-2,4-diamine (CAS RN 950782-86-2), compound of formula I+1-(2-chloro-6-propylimidazo[1,2-b]pyridazin-3-ylsulfonyl)-3-(4,6-dimethoxypyrimidin-2-yl)urea (CAS RN 570415-88-2), and 5-(2,6-difluoro-benzyloxymethyl)-5-methyl-3-(3-methyl-thiophen-2-yl)-4,5-dihydro-isoxazole (CAS RN 403640-27-7) and compound of formula I+ZJ0273.

The mixing partners for the compound of formula I may also be in the form of esters or salts, as mentioned e.g. in The Pesticide Manual, 12th Edition (BCPC) 2000.

The compounds of formula I according to the invention can also be used in combination with safeners. Preferably, in these mixtures, the compound of the formula I is one of those compounds listed in Tables 1 to 16 below. The following mixtures with safeners, especially, come into consideration:

compound of formula I+cloquintocet-mexyl, compound of formula I+cloquintocet acid and salts thereof, compound of formula I+cyprosulfamide, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecoprop and compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

As a rule, the weight ratio of herbicide of the formula I to safener is 1:100 bis 100:1, preferably 1:10 bis 10:1 and particularly 1:5 bis 5:1 vor.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 5 g of safener/kg of seed, and more preferably 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the mixture partner of the compound of formula I together with one of the safeners mentioned above.

In another aspect, the invention provides a herbicidal composition, which comprises a herbicidally effective amount of a compound of formula I, and optionally a further herbicide as mixture partner for the compound of formula I, or optionally a safener, or both.

The mixing partners of the compound of formula I may also be in the form of esters or salts, as mentioned e.g. in The Pesticide Manual, 12th Edition (BCPC), 2000.

In the above-mentioned mixtures of compounds of formula I, in particular a compound selected from said Tables 1 to 16, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on other hand, molar ratios.

The mixtures can advantageously be used in the above-mentioned formulations (in which case "active ingredient" relates to the respective mixture of compound of formula I with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a compound of formula I selected from Tables 1 to 16 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 16 and the active ingredients as described above is not essential for working the present invention.

The invention is illustrated by the following preparation examples. The H-NMR data of certain compounds of this invention show line broadening at room temperature, suggesting the existence of plural conformational isomers due to, for example keto-enol tautomerism, hindered rotation, ring inversion in the [1,2,5]triazepane moiety or nitrogen inversion at the [1,2,5]triazepane N-OR center. Broad signals have been labeled with 'br' accordingly. GC-MS analyses were performed on a Thermo Electron instrument where a TRACE GC ULTRA gas chromatograph (equipped with a Zebron Phenomenex ZB-5 ms column) was linked to a DSQ mass spectrometer characterizing the compounds by chemical ionization in the positive ion mode (CI+) using methane as a reagent gas.

Example 1

Preparation of 2,2-Dimethyl-propionic acid 3-methoxy-9-oxo-8-(2,4,6-trimethyl-phenyl)-2,3,4,5-tetrahydro-1H,9H-pyrazolo[1,2-a][1,2,5]triazepin-7-yl ester (compound P1.1)

Step 1: Preparation of 2-[(2-Hydroxy-ethyl)-methoxy-amino]-ethanol

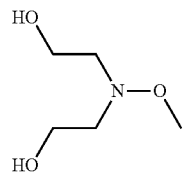

To an aqueous solution of O-methyl-hydroxylamine hydrochloride (41.8 g, 40% w/w in water, 200.2 mmol) in a reaction vessel equipped with a dry ice reflux condenser tempered at −30° C. with a cryostat and with a double-walled addition funnel cooled by ice was added sodium hydroxide (8.0 g, 200.0 mmol) at 0° C. slowly in portions. The required amount of ethylene oxide (oxirane, 21.8 ml, 19.4 g, 440 mmol) was condensed from a gas cylinder in a dry ice trap, transferred to the cold addition funnel, and added slowly to the reaction mixture over 50 minutes under cooling to keep the temperature under control and to allow a light reflux of oxirane during the addition. The reaction was stirred at room temperature for 20 hours, the mixture treated with additional ethylene oxide (5 ml, 4.45 g, 101 mmol) and further stirred at room temperature for 4.5 hours. Water was largely evaporated in vacuo and the residue submitted to distillation under reduced pressure. Yield: 24.4 g of 2-[(2-hydroxy-ethyl)-methoxy-amino]-ethanol as a colorless oil, by 110-120° C./8 mbar.

$^1$H-NMR (400 MHz, CDCl$_3$): δ 2.87 (t, 4H), 3.26 (br s, 2H), 3.59 (s, 3H), 3.73 (m, 4H) ppm.
$^{13}$C-NMR (101 MHz, CDCl$_3$): δ 58.7, 60.6, 61.5 ppm.

Step 2: Preparation of Methanesulfonic acid 2-[(2-methanesulfonyloxy-ethyl)-methoxy-amino]-ethyl ester

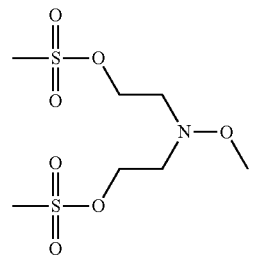

To a solution of 2-[(2-hydroxy-ethyl)-methoxy-amino]-ethanol (20.0 g, 148.0 mmol) and triethylamine (41.3 ml, 30.0 g, 296.3 mmol) in tetrahydrofuran (855 ml) under argon was added methanesulfonyl chloride (25.2 ml, 37.3 g, 325.6 mmol) dropwise, keeping the temperature below 20° C. with an ice bath. The reaction mixture was stirred at room temperature for 4 hours, the resulting precipitate filtered off and the filtrate concentrated. The residue was diluted with ethyl acetate, washed with water, dried over sodium sulfate and concentrated. Yield: 40.0 g of methanesulfonic acid 2-[(2-methanesulfonyloxy-ethyl)-methoxy-amino]-ethyl ester as a pale yellow oil, this material was used without further purification.

$^1$H-NMR (400 MHz, CDCl$_3$): δ 3.06 (s, 6H), 3.07 (t, 4H), 3.58 (s, 3H), 4.38 (t, 4H) ppm.
$^{13}$C-NMR (101 MHz, CDCl$_3$): δ 37.5, 57.3, 61.7, 66.3 ppm.
GC-MS (CI+): 292 (M+H)$^+$; R$_t$=7.20 min Step 3: Preparation of 5-Methoxy-[1,2,5]triazepane-1,2-dicarboxylic acid di-tert-butyl ester (compound P4.1)

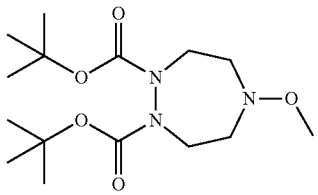

To a solution of N,N'-di-tert-butyl hydrazinedicarboxylate (1,2-bis-Boc-hydrazine, 8.0 g, 34.4 mmol) and methanesulfonic acid 2-[(2-methanesulfonyloxy-ethyl)-methoxy-amino]-ethyl ester (10.0 g, 34.3 mmol) in toluene (100 ml) was added aqueous sodium hydroxide (50 ml, 30% NaOH w/w in water), followed by tetra-butyl ammonium bromide (332 mg, 1.03 mmol) and the reaction mixture was heated at reflux for one hour. After cooling, the layers were separated, the organic phase washed with water, dried over sodium sulfate and evaporated. Yield: 11.2 g of 5-methoxy-[1,2,5]triazepane-1,2-dicarboxylic acid di-tert-butyl ester (compound P4.1) as a yellow oil, this material was used without further purification.

$^1$H-NMR (400 MHz, CDCl$_3$): δ 1.44 (s, 18H), 2.82-3.27 (m, 6H), 3.50 (s, 3H), 3.83-4.07 (m, 2H) ppm. $^{13}$C-NMR (101 MHz, CDCl$_3$): δ 28.2, 45.7, 55.9, 59.6, 80.7, 154.2 ppm (mixture of rotamers/conformers, major isomer reported).

Step 4: Preparation of 5-Methoxy-[1,2,5]triazepane hydrochloride salt (compound P4.2)

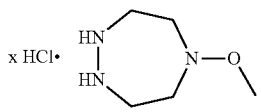

A solution of 5-methoxy-[1,2,5]triazepane-1,2-dicarboxylic acid di-tert-butyl ester in diethyl ether was treated with gaseous hydrogen chloride to generate a white precipitate. The solid was filtered, washed with diethyl ether and dried to afford 5-methoxy-[1,2,5]triazepane-1,2-dicarboxylic acid di-tert-butyl ester hydrochloride salt. To a suspension of 5-methoxy-[1,2,5]triazepane-1,2-dicarboxylic acid di-tert-butyl ester hydrochloride salt (2.5 g, 6.8 mmol) in ethyl acetate (10 ml) was added a solution of hydrogen chloride in 1,4-dioxane (4 M, 9 ml, 36.0 mmol) at room temperature dropwise. The reaction mixture was heated at 90° C. for one hour, the solvent evaporated, the residue washed with diethyl ether and dried in vacuo. Yield: 1.4 g of 5-methoxy-[1,2,5]triazepane hydrochloride salt (compound P4.2) as a yellowish solid, this material was used without further purification.

$^1$H-NMR (400 MHz, d$_6$-DMSO): δ 3.15-3.24 (m, 4H), 3.24-3.31 (m, 4H), 3.50 (s, 3H), 9.39 (br s, ~5H) ppm. $^{13}$C-NMR (101 MHz, d$_6$-DMSO): δ 42.8, 54.3, 58.8 ppm.
GC-MS (CI+): 132 (M+H)$^+$; R$_t$=2.92 min (free base)

Step 5: Preparation of 3-Methoxy-8-(2,4,6-trimethyl-phenyl)-tetrahydro-pyrazolo[1,2-a][1,2,5]triazepine-7,9-dione (compound P2.1)

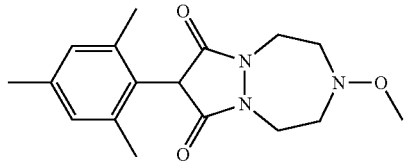

A degassed suspension of 5-methoxy-[1,2,5]triazepane hydrochloride salt (350 mg, 1.71 mmol) and triethylamine (1.0 ml, 726 mg, 7.17 mmol) in xylene (8 ml) was stirred under argon at 60° C. for one hour. After further addition of 2-(2,4,6-trimethyl-phenyl)-malonic acid diethyl ester (482 mg, 1.73 mmol), the reaction mixture was heated at 150° C. (oil bath temperature) for 18 hours. The cooled reaction mixture was poured on ice, the pH made alkaline by addition of 5N aqueous sodium hydroxide, the aqueous layer extracted twice with ethyl acetate and the combined organic layers discarded. The aqueous alkaline phase was acidified with cooling to pH 2-3 by addition of a 4N HCl solution and the product thoroughly extracted with dichloromethane. The combined organic layers were dried over sodium sulfate and concentrated in vacuo. The base-acidification workup protocol is repeated a second time. Yield: 24 mg of 3-methoxy-8-(2,4,6-trimethyl-phenyl)-tetrahydro-pyrazolo[1,2-a][1,2,5]triazepine-7,9-dione (compound P2.1) as a beige solid.

$^1$H-NMR (400 MHz, CDCl$_3$): δ 2.03 (s, 3H), 2.24 (s, 3H), 2.39 (s, 3H), 3.15-3.24 (m, 2H), 3.30-3.43 (m, 2H), 3.58 (s, 3H), 3.97-4.09 (m, 2H), 4.17-4.29 (m, 2H), 4.68 (s, 1H), 6.82 (s, 1H), 6.92 (s, 1H) ppm.
LC/MS (ES+): 318 (M+H)$^+$ Step 6: Preparation of 2,2-Dimethyl-propionic acid 3-methoxy-9-oxo-8-(2,4,6-trimethyl-phenyl)-2,3,4,5-tetrahydro-1H,9H-pyrazolo[1,2-a][1,2,5]triazepin-7-yl ester (title compound P1.1)

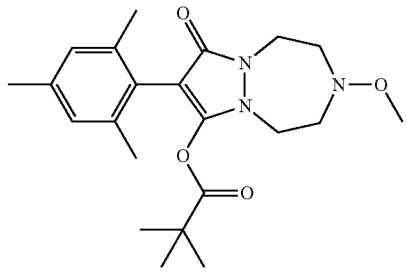

To a solution of 3-methoxy-8-(2,4,6-trimethyl-phenyl)-tetrahydro-pyrazolo[1,2-a][1,2,5]triazepine-7,9-dione (162 mg, 0.51 mmol), triethylamine (0.107 ml, 78 mg, 0.77 mmol) and a catalytic amount of 4-dimethylaminopyridine in tetrahydrofuran (4 ml) at 0° C. was added 2,2-dimethyl-propionyl chloride (pivaloyl chloride, 0.082 ml, 80 mg, 0.67 mmol) dropwise. The suspension was stirred at 0° C. for 45 minutes, the solvent evaporated and the residue diluted with ethyl acetate. The organic phase was washed with water and brine, dried over sodium sulfate and concentrated. Yield: 160 mg of 2,2-dimethyl-propionic acid 3-methoxy-9-oxo-8-(2,4,6-trimethyl-phenyl)-2,3,4,5-tetrahydro-1H,9H-pyrazolo[1,2-a][1,2,5]triazepin-7-yl ester (title compound P1.1) as an off-white solid, mp 147-148° C.

$^1$H-NMR (400 MHz, CDCl$_3$): δ 1.03 (s, 9H), 2.15 (s, 6H), 2.23 (s, 3H), 3.19-3.22 (m, 2H), 3.25-3.27 (m, 2H), 3.54 (s, 3H), 3.84-3.94 (m, 2H), 4.23-4.32 (m, 2H), 6.82 (s, 2H) ppm.

LC/MS (ES+): 402 (M+H)$^+$; R$_t$=1.79 min

Example 2

Preparation of Carbonic acid ethyl ester 3-methoxy-9-oxo-8-(2,4,6-trimethyl-phenyl)-2,3,4,5-tetrahydro-1H,9H-pyrazolo[1,2-a][1,2,5]triazepin-7-yl ester (compound P1.2)

Step 1: Preparation of N'-[2-(2,4,6-Trimethyl-phenyl)-acetyl]-hydrazinecarboxylic acid ethyl ester

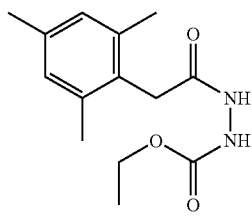 [SMILES: CCOC(=O)NNC(=O)Cc1c(C)cc(C)cc1C]

To a solution of hydrazinecarboxylic acid ethyl ester (ethyl carbazate, 32.8 g, 314.9 mmol) and triethylamine (44.1 ml, 32.0 g, 316.4 mmol) in tetrahydrofuran (1000 ml) at 0° C. was added (2,4,6-trimethyl-phenyl)-acetyl chloride (62.0 g, 315.2 mmol) dropwise. The thick suspension was stirred at room temperature for one hour and the solvent evaporated. The residue was suspended in a mixture of t-butyl methyl ether (500 ml) and water (500 ml), stirred, filtered and the solid washed with small portions of water and t-butyl methyl ether. The solid was dried in vacuo over phosphorus pentoxide at 40° C. Yield: 78.4 g of N'-[2-(2,4,6-trimethyl-phenyl)-acetyl]-hydrazinecarboxylic acid ethyl ester as a white solid, mp 184-186° C.

$^1$H-NMR (400 MHz, CDCl$_3$): δ 1.25 (t, J=7.1 Hz, 3H), 2.27 (s, 3H), 2.31 (s, 6H), 3.66 (s, 2H), 4.16 (q, J=7.1 Hz, 2H), 6.47 (br s, 1H), 6.91 (s, 2H), 6.96 (br s, 1H) ppm. $^{13}$C-NMR (101 MHz, CDCl$_3$): δ 14.3, 20.1, 20.9, 35.5, 62.2, 127.2, 129.4, 137.3, 137.4, 156.3, 170.4 ppm.

LC/MS (ES+): 265 (M+H)$^+$, 287 (M+Na)$^+$; R$_t$=1.19 min

Step 2: Preparation of 5-Methoxy-2-[2-(2,4,6-trimethyl-phenyl)-acetyl]-[1,2,5]triazepane-1-carboxylic acid ethyl ester (compound P3.1)

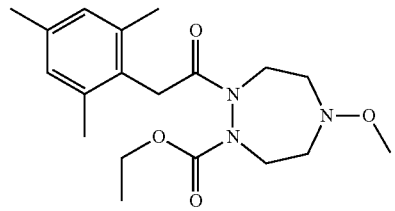

To a vigorously stirred suspension of N'-[2-(2,4,6-trimethyl-phenyl)-acetyl]-hydrazinecarboxylic acid ethyl ester (4.22 g, 15.96 mmol) in toluene (80 ml) was added aqueous sodium hydroxide (12 ml, 30% NaOH w/w in water) and tetra-butyl ammonium bromide (160 mg, 0.48 mmol) at room temperature, followed by methanesulfonic acid 2-[(2-methanesulfonyloxy-ethyl)-methoxy-amino]-ethyl ester (4.66 g, 16.00 mmol) dropwise over 15 minutes at 65° C. The reaction mixture was heated at 65° C. for 6.5 hours. After cooling, the layers were separated, the organic phase evaporated, the residue dissolved in ethyl acetate, washed with water, dried over sodium sulfate and concentrated. The residue was purified by chromatography on silica gel (cyclohexane/ethyl acetate/dichloromethane 5:4:1). Yield: 2.6 g of 5-methoxy-2-[2-(2,4,6-trimethyl-phenyl)-acetyl]-[1,2,5]triazepane-1-carboxylic acid ethyl ester (compound P3.1) as a colorless oil.

$^1$H-NMR (400 MHz, CDCl$_3$): δ 1.32 (t, 3H), 2.18 (s, 6H), 2.24 (s, 3H), 2.85-3.24 (m, 6H), 3.50 (s, 3H), 3.59 (s, 2H), 3.92-3.97 (m, 2H), 4.24 (q, 2H), 6.85 (s, 2H) ppm.

$^{13}$C-NMR (101 MHz, CDCl$_3$): δ 14.3, 20.2, 20.9, 33.4, 45.2, 47.5, 54.9, 59.7, 62.9, 128.9, 136.2, 136.8, 155.6, 172.2 ppm.

LC/MS (ES+): 364 (M+H)$^+$; R$_t$=1.80 min

Step 3: Preparation of 3-Methoxy-8-(2,4,6-trimethyl-phenyl)-tetrahydro-pyrazolo[1,2-a][1,2,5]triazepine-7,9-dione (compound P2.1)

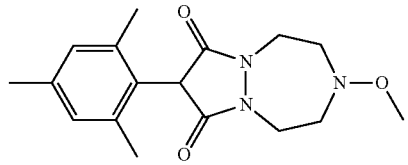

To a solution of 5-methoxy-2-[2-(2,4,6-trimethyl-phenyl)-acetyl]-[1,2,5]triazepane-1-carboxylic acid ethyl ester (1.035 g, 2.85 mmol) in absolute dimethylformamide (12 ml) at room temperature in a flame-dried flask under argon was added potassium tert-butoxide (479 mg, 4.27 mmol; weighed under argon atmosphere) in three portions. The reaction mixture was stirred for 1.5 hours, poured on ice, the aqueous layer extracted twice with ethyl acetate and the combined organic layers discarded. The aqueous alkaline phase was acidified with cooling to pH 2-3 by addition of a 1N HCl solution and the product thoroughly extracted with ethyl acetate. The combined organic layers were dried over sodium sulfate and concentrated in vacuo. Yield: 500 mg of 3-methoxy-8-(2,4,6-trimethyl-phenyl)-tetrahydro-pyrazolo[1,2-a][1,2,5]triazepine-7,9-dione (compound P2.1) as a solid with a purity of 91% by LC-MS. This material (120 mg) was triturated in diethyl ether, filtered and dried to afford 110 mg of clean product, mp 229-230° C.

$^1$H-NMR (400 MHz, CDCl$_3$): δ 2.03 (s, 3H), 2.24 (s, 3H), 2.39 (s, 3H), 3.15-3.24 (m, 2H), 3.30-3.43 (m, 2H), 3.58 (s, 3H), 3.97-4.09 (m, 2H), 4.17-4.29 (m, 2H), 4.68 (s, 1H), 6.82 (s, 1H), 6.92 (s, 1H) ppm.

LC/MS (ES+): 318 (M+H)$^+$; R$_t$=1.44 min

Step 4: Preparation of Carbonic acid ethyl ester 3-methoxy-9-oxo-8-(2,4,6-trimethyl-phenyl)-2,3,4,5-tetrahydro-1H,9H-pyrazolo[1,2-a][1,2,5]triazepin-7-yl ester (title compound P1.2)

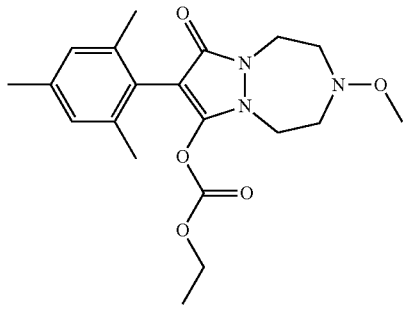

To a solution of 3-methoxy-8-(2,4,6-trimethyl-phenyl)-tetrahydro-pyrazolo[1,2-a][1,2,5]triazepine-7,9-dione (106 mg, 0.33 mmol), triethylamine (0.070 ml, 51 mg, 0.50 mmol) and a catalytic amount of 4-dimethylaminopyridine in tetrahydrofuran (2 ml) at 0° C. was added ethyl chloroformate (0.035 ml, 40 mg, 0.37 mmol) dropwise. The suspension was stirred at 0° C. for 20 minutes, treated with more triethylamine (0.070 ml, 51 mg, 0.50 mmol) and ethyl chloroformate (0.035 ml, 40 mg, 0.37 mmol) dropwise, and further stirred at 0° C. for 10 minutes. The solvent was evaporated, the residue diluted with ethyl acetate, the organic phase washed with water and brine, dried over sodium sulfate and concentrated. The gummy residue was triturated in cyclohexane and diethyl ether, stirred at room temperature, filtered and dried. Yield: 100 mg of carbonic acid ethyl ester 3-methoxy-9-oxo-8-(2,4,6-trimethyl-phenyl)-2,3,4,5-tetrahydro-1H,9H-pyrazolo[1,2-a][1,2,5]triazepin-7-yl ester (title compound P1.2) as a pale yellow solid.

$^1$H-NMR (400 MHz, CDCl$_3$): δ 1.18 (t, 3H), 2.16 (s, 6H), 2.26 (s, 3H), 3.16-3.23 (m, 2H), 3.23-3.29 (m, 2H), 3.55 (s, 3H), 3.93-4.02 (m, 2H), 4.13 (q, 2H), 4.21-4.29 (m, 2H), 6.87 (s, 2H) ppm.

LC/MS (ES+): 390 (M+H)$^+$; R$_t$=1.63 min

Example 3

Preparation of 8-(2,5-Dimethyl-phenyl)-3-methoxy-tetrahydro-pyrazolo[1,2-a][1,2,5]triazepine-7,9-dione (compound P2.4)

Step 1: Preparation of 5-Methoxy-[1,2,5]triazepane-1,2-dicarboxylic acid 1-tert-butyl ester 2-ethyl ester (compound P4.3)

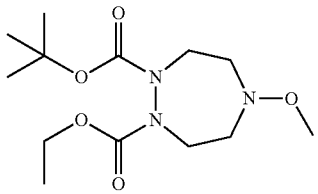 [SMILES: CCOC(=O)N1CCN(OC)CCN1C(=O)OC(C)(C)C]

A solution of N'-tert-butyl-oxy-carbonyl-hydrazinecarboxylic acid ethyl ester (30.0 g, 146.9 mmol) in dimethylformamide (100 ml) was added dropwise over 30 minutes to a stirred suspension of sodium hydride (15.14 g, 55% w/w dispersion in mineral oil, 347.0 mmol) in dimethylformamide (250 ml) at 0-5° C. under nitrogen atmosphere. The mixture was stirred at 5° C. for 30 minutes, allowed to warm to room temperature and subsequently heated to 40-50° C. to bring hydrogen evolution to completion (caution!). A solution of methanesulfonic acid 2-[(2-methanesulfonyloxy-ethyl)-methoxy-amino]-ethyl ester (44.94 g, 154.2 mmol) in dimethylformamide (150 ml) was then added dropwise over 45 minutes at 0-5° C. The reaction mixture was stirred at 0° C. for 30 minutes, allowed to warm to room temperature and subsequently heated to 65° C. for 6 hours (caution!, more hydrogen evolution was observed during initial heating). The cooled mixture was poured on ice (500 g), diluted with ethyl acetate (300 ml) and the aqueous phase saturated with sodium chloride. The layers were separated, the aqueous phase extracted with ethyl acetate (5×200 ml), the combined organic layers washed twice with brine (100 ml), dried over sodium sulfate and concentrated. The residue was purified by chromatography on silica gel (cyclohexane/ethyl acetate 20:1 to 4:1). Yield: 32.6 g of 5-methoxy-[1,2,5]triazepane-1,2-dicarboxylic acid 1-tert-butyl ester 2-ethyl ester (compound P4.3) as a clear yellowish oil.

$^1$H-NMR (400 MHz, CD$_3$OD): δ 1.19-1.35 (m, 3H), 1.40-1.54 (m, 9H), 2.89-3.38 (br m, 6H), 3.50 (s, 3H), 3.90-4.04 (m, 2H), 4.09-4.26 (m, 2H) ppm.

LC/MS (ES+): 326 (M+Na)$^+$; R$_t$=1.58 min

Step 2: Preparation of 5-Methoxy-[1,2,5]triazepane-1-carboxylic acid ethyl ester hydrochloride salt (compound P4.4) and its free base 5-Methoxy-[1,2,5]triazepane-1-carboxylic acid ethyl ester (compound P4.5)

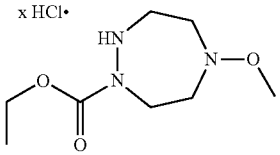

To a solution of 5-methoxy-[1,2,5]triazepane-1,2-dicarboxylic acid 1-tert-butyl ester 2-ethyl ester (10.0 g, 32.96 mmol) in diethyl ether (100 ml) under argon was added a 2 M hydrogen chloride solution in diethyl ether (160 ml, 320 mmol) dropwise at room temperature. The reaction mixture was stirred at ambient temperature overnight forming a suspension. The solvent was evaporated, the residue solubilised in absolute methanol (100 ml) and concentrated to dryness. The product was crystallized with diethyl ether under argon to afford an amorphous white solid. Yield: 8.2 g of 5-methoxy-[1,2,5]triazepane-1-carboxylic acid ethyl ester hydrochloride salt (compound P4.4) as a hygroscopic solid.

$^1$H-NMR (400 MHz, CD$_3$OD) δ 1.35 (t, J=7.1 Hz, 3H), 3.53 (br m, 2H), 3.72 (br m, 2H), 3.77 (s, 3H), 3.82 (br m, 2H), 4.06 (m, 2H), 4.34 (q, J=7.1 Hz, 2H) ppm.

$^{13}$C-NMR (101 MHz, CD$_3$OD): δ 14.8, 43.6, 44.6, 52.9, 56.7, 60.7, 65.6, 155.4 ppm.

LC/MS (ES+): 204 (M+H)$^+$; R$_t$=1.03 min (free base)

The above protocol, starting with 5-methoxy-[1,2,5]triazepane-1,2-dicarboxylic acid 1-tert-butyl ester 2-ethyl ester (7.0 g, 23.07 mmol) in diethyl ether (100 ml) treated under argon with a 2 M hydrogen chloride solution in diethyl ether (160 ml, 320 mmol), delivered 5-methoxy-[1,2,5]triazepane-1-carboxylic acid ethyl ester hydrochloride salt (6.1 g) as a hygroscopic solid. This material was dissolved in water (20 ml) and the pH was made alkaline by careful addition of solid sodium carbonate under cooling (temperature kept below 15° C.). The aqueous phase was extracted with diethyl ether (3×50 ml), the combined organic layers washed with brine, dried over magnesium sulfate and concentrated. Yield: 4.0 g of 5-methoxy-[1,2,5]triazepane-1-carboxylic acid ethyl ester (compound P4.5) as a pale yellow viscous oil.

¹H-NMR (400 MHz, CDCl₃): δ 1.29 (t, J=7.1 Hz, 3H), 3.03 (m, 4H), 3.21 (t, J=5.8 Hz, 2H), 3.52 (s, 3H), 3.62 (t, J=5.8 Hz, 2H), 4.18 (q, J=7.1 Hz, 2H), 4.75 (br s, 1H) ppm.
¹³C-NMR (101 MHz, CDCl₃): δ 14.5, 45.6, 48.0, 55.9, 58.5, 59.2, 61.6, 155.9 ppm.
LC/MS (ES+): 204 (M+H)⁺; R$_t$=1.03 min Step 3: Preparation of 2-[2-(2,5-Dimethyl-phenyl)-acetyl]-5-methoxy-[1,2,5]triazepane-1-carboxylic acid ethyl ester (compound P3.3)

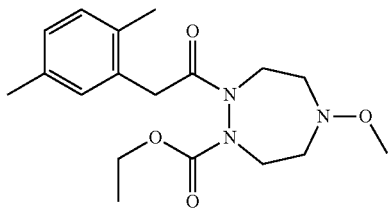

To a solution of 5-methoxy-[1,2,5]triazepane-1-carboxylic acid ethyl ester hydrochloride salt (1.33 g, 4.84 mmol), triethylamine (1.68 ml, 1.22 g, 12.07 mmol) and a catalytic amount of 4-dimethylaminopyridine in tetrahydrofuran (20 ml) at 0-5° C. was added a solution of (2,5-dimethyl-phenyl)-acetyl chloride (0.93 g, 5.09 mmol) in tetrahydrofuran (5 ml) dropwise. The suspension was stirred at 0-5° C. for one hour, and at room temperature for 4 hours. The solvent was evaporated, the residue diluted with ethyl acetate (50 ml) and water (20 ml), the layers separated and the aqueous phase extracted with ethyl acetate (2×25 ml). The combined organic layers were washed with water (2×20 ml) and brine (20 ml), dried over sodium sulfate and concentrated. The residue was purified by chromatography on silica gel (cyclohexane/ethyl acetate 2:1). Yield: 1.1 g of 2-[2-(2,5-dimethyl-phenyl)-acetyl]-5-methoxy-[1,2,5]triazepane-1-carboxylic acid ethyl ester (compound P3.3) as a viscous oil. ¹H-NMR (400 MHz, CD₃OD): δ 1.14-1.39 (br m, 3H), 2.18 (s, 3H), 2.26 (s, 3H), 2.83-3.09 (br m, 4H), 3.13-3.32 (br m, 2H), 3.48 (s, 3H), 3.62 (br s, 2H), 3.78-4.32 (br m, overlapping signals, total 4H), 6.91 (s, 1H), 6.95 (d, J=7.8 Hz, 1H), 7.03 (d, J=7.8 Hz, 1H) ppm.
LC/MS (ES+): 350 (M+H)⁺; R$_t$=1.71 min Step 4: Preparation of 8-(2,5-Dimethyl-phenyl)-3-methoxy-tetrahydro-pyrazolo[1,2-a][1,2,5]triazepine-7,9-dione (title compound P2.4)

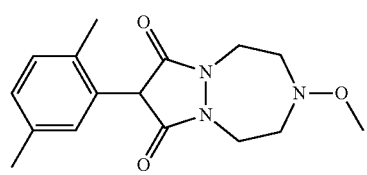 [SMILES: CON1CCN2C(=O)C(c3cc(C)ccc3C)C(=O)N2CC1]

To a solution of 2-[2-(2,5-dimethyl-phenyl)-acetyl]-5-methoxy-[1,2,5]triazepane-1-carboxylic acid ethyl ester (800 mg, 2.29 mmol) in absolute dimethylformamide (10 ml) at 10° C. was added sodium methoxide (371 mg, 6.87 mmol) in one portion and stirring continued at 10° C. for 30 minutes, then at room temperature for two hours. The solvent was evaporated in vacuo, the residue diluted in cold water (10 ml), acidified to pH 5 with 2N HCl and thoroughly extracted with ethyl acetate. The combined organic layers were washed with brine (3×15 ml), dried over sodium sulfate and concentrated. The residue was triturated with diethyl ether, filtered, washed with cold ether and dried in vacuo. Yield: 450 mg of 8-(2,5-dimethyl-phenyl)-3-methoxy-tetrahydro-pyrazolo[1,2-a][1,2,5]triazepine-7,9-dione (title compound P2.4) as an off-white solid, mp 167-169° C.
¹H-NMR (400 MHz, CDCl₃): δ 2.28 (s, 3H), 2.31 (s, 3H), 3.16-3.34 (m, 4H), 3.54 (s, 3H), 3.98-4.20 (m, 4H), 4.41 (s, 1H), 6.84 (s, 1H), 7.03 (d, J=7.7 Hz, 1H), 7.10 (d, J=7.7 Hz, 1H) ppm.
LC/MS (ES+): 304 (M+H)⁺; R$_t$=1.38 min Example 4

Preparation of 8-(4-Chloro-2,6-dimethyl-phenyl)-3-methoxy-tetrahydro-pyrazolo[1,2-a][1,2,5]triazepine-7,9-dione (compound P2.2)

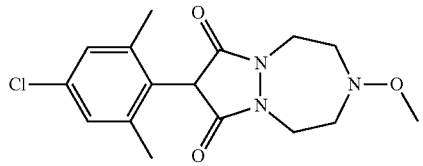 [SMILES: CON1CCN2C(=O)C(c3c(C)cc(Cl)cc3C)C(=O)N2CC1]

A degassed suspension of 5-methoxy-[1,2,5]triazepane hydrochloride salt (100 mg, 0.49 mmol) and triethylamine (0.33 ml, 207 mg, 2.05 mmol) in xylene (2.5 ml) was stirred under argon at 60° C. for 30 minutes in a microwave vial. After further addition of 2-(4-chloro-2,6-dimethyl-phenyl)-malonamide (120 mg, 0.50 mmol), the vial was capped and irradiated twice with microwaves at 180° C. for 10 minutes. The solid deposit on the vial wall was dissolved in dichloromethane, the solvent evaporated, the oily residue dissolved in 5N aqueous sodium hydroxide, the aqueous layer extracted with ethyl acetate (3×) and the combined organic layers discarded. The aqueous alkaline phase was acidified with cooling to pH 2-3 by addition of a 4N HCl solution and the product thoroughly extracted with dichloromethane. The combined organic layers were dried over sodium sulfate and concentrated in vacuo. Yield: 10 mg of 8-(4-chloro-2,6-dimethyl-phenyl)-3-methoxy-tetrahydro-pyrazolo[1,2-a][1,2,5]triazepine-7,9-dione (compound P2.2) as a beige solid.
¹H-NMR (400 MHz, CDCl₃): δ 2.06 (s, 3H), 2.40 (s, 3H), 3.11-3.19 (m, 2H), 3.29-3.38 (m, 2H), 3.54 (s, 3H), 3.96-4.09 (m, 2H), 4.13-4.26 (m, 2H), 4.66 (s, 1H), 7.02 (s, 1H), 7.11 (s, 1H) ppm.
LC/MS (ES+): 338/340 (M+H)⁺; R$_t$=1.54 min Example 5

Preparation of 8-(2,6-Diethyl-4-methyl-phenyl)-3-methoxy-tetrahydro-pyrazolo[1,2-a][1,2,5]triazepine-7,9-dione (compound P2.3)

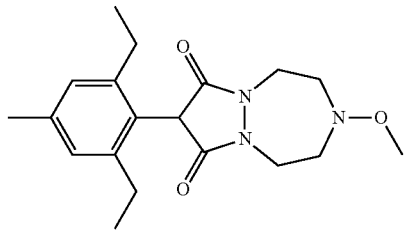

A degassed solution in a microwave vial of 5-methoxy-[1,2,5]triazepane (free base, 50 mg, 0.38 mmol) and 2-(2,6-diethyl-4-methyl-phenyl)-malonamide (95 mg, 0.38 mmol) in 1,2-dichloroethane (2.5 ml) under argon was irradiated with microwaves at 180° C. for 5 minutes. The solvent was evaporated, the residue dissolved in 5N aqueous sodium hydroxide, the aqueous layer extracted twice with ethyl acetate and the combined organic layers discarded. The aqueous alkaline phase was acidified with cooling to pH 2-3 by addition of a 4N HCl solution and the product thoroughly extracted with dichloromethane. The combined organic layers were dried over sodium sulfate and concentrated in vacuo. Yield: 20 mg of 8-(2,6-diethyl-4-methyl-phenyl)-3-methoxy-tetrahydro-pyrazolo[1,2-a][1,2,5]triazepine-7,9-dione (compound P2.3) as a tan solid.

$^1$H-NMR (400 MHz, CDCl$_3$): δ 1.17 (t, 3H), 1.24 (t, 3H), 2.22 (q, 2H), 2.29 (s, 3H), 2.68 (q, 2H), 3.07-3.13 (m, 2H), 3.36-3.41 (m, 2H), 3.55 (s, 3H), 3.92-4.05 (m, 2H), 4.20-4.31 (m, 2H), 4.67 (s, 1H), 6.90 (s, 1H), 6.92 (s, 1H) ppm.

LC/MS (ES+): 344 (M−H)$^-$; R$_t$=1.68 min

Example 6

Preparation of N'-[2-(2,4,6-Trimethyl-phenyl)-acetyl]-hydrazinecarboxylic acid tert-butyl ester

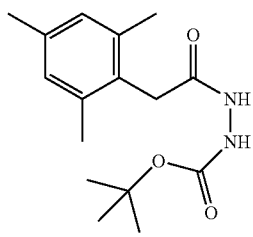 [SMILES: Cc1cc(C)c(CC(=O)NNC(=O)OC(C)(C)C)c(C)c1]

Prepared in analogy to Example 2, step 1 from hydrazinecarboxylic acid tert-butyl ester (tert-butyl carbazate) and (2,4,6-trimethyl-phenyl)-acetyl chloride. N'-[2-(2,4,6-Trimethyl-phenyl)-acetyl]-hydrazinecarboxylic acid tert-butyl ester as a white solid, mp 138-140° C.

$^1$H-NMR (400 MHz, CDCl$_3$): δ 1.44 (s, 9H), 2.27 (s, 3H), 2.31 (s, 6H), 3.65 (s, 2H), 6.35 (br s, 1H), 6.90 (s, 2H), 6.98 (br s, 1H) ppm. $^{13}$C-NMR (101 MHz, CDCl$_3$): δ 20.1, 20.8, 28.0, 35.4, 81.6, 127.4, 129.3, 137.2, 137.3, 155.2, 170.1 ppm.

LC/MS (ES+): 315 (M+Na)$^+$; R$_t$=1.45 min

Example 7

Preparation of 3-Methoxy-8-(2,4,6-trimethyl-phenyl)-tetrahydro-pyrazolo[1,2-a][1,2,5]triazepine-7,9-dione (compound P2.1)

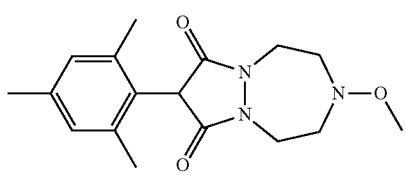

To a degassed suspension of 5-methoxy-[1,2,5]triazepane hydrochloride salt (408 mg, 2.0 mmol) and triethylamine (1.115 ml, 810 mg, 8.0 mmol) in diethyl ether (1.0 ml) at 0-5° C. was added a solution of 2-(chlorocarbonyl)-2-mesitylketene [prepared according to Nakanishi's method: S. Nakanishi, K. Butler, Org. Prep. Proced. Int. 7, 155-158 (1975)] (891 mg, 4.0 mmol) in diethyl ether (1.0 ml) dropwise. The suspension was stirred at 0-5° C. for 30 minutes, and at room temperature overnight. The reaction mixture was poured on water (5 ml), the pH made alkaline (pH 14) by addition of aqueous sodium hydroxide, the aqueous layer extracted with ethyl acetate (3×10 ml) and the combined organic layers discarded. The aqueous alkaline phase was acidified with cooling to pH 5 by addition of a 4N HCl solution and the product thoroughly extracted with ethyl acetate (3×20 ml) and dichloromethane (3×20 ml). The combined organic layers were dried over sodium sulfate and concentrated in vacuo. The residue was purified by chromatography on silica gel (gradient ethyl acetate/cyclohexane 5:1→4 ethyl acetate). Yield: 70 mg of 3-methoxy-8-(2,4,6-trimethyl-phenyl)-tetrahydro-pyrazolo[1,2-a][1,2,5]triazepine-7,9-dione (compound P2.1) as a pale beige solid, mp 227-229° C.

$^1$H-NMR (400 MHz, CDCl$_3$) is consistent with the previously described spectral data (see Example 2, step 3).

LC/MS (ES+): 318 (M+H)$^+$

Example 8

Preparation of 8-(2-Ethyl-4,6-dimethyl-phenyl)-3-methoxy-tetrahydro-pyrazolo[1,2-a][1,2,5]triazepine-7,9-dione (compound P2.14)

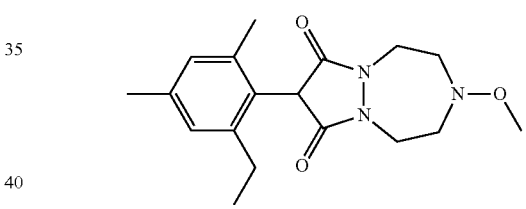

To a solution of 2-[2-(2-ethyl-4,6-dimethyl-phenyl)-acetyl]-5-methoxy-[1,2,5]triazepane-1-carboxylic acid ethyl ester (550 mg, 1.46 mmol) in absolute dimethylformamide (5 ml) at 80° C. was added sodium methoxide (240 mg, 4.44 mmol) in one portion and stirring continued at 80° C. for 20 minutes. The cooled reaction mixture was poured on ice, the aqueous alkaline phase was acidified to pH 5 by addition of a 6N HCl solution, the resulting suspension was filtered, the obtained solid dissolved in dichloromethane, the organic layer was dried over sodium sulfate and concentrated in vacuo. The residue was purified by chromatography on silica gel (ethyl acetate/methanol 20:1). Yield: 220 mg of 8-(2-ethyl-4,6-dimethyl-phenyl)-3-methoxy-tetrahydro-pyrazolo[1,2-a][1,2,5]triazepine-7,9-dione (compound P2.14) as a pale brown solid, mp 213-215° C.

LC/MS (ES+): 332 (M+H)$^+$; R$_t$=1.54 min

Compounds of the formula I from Table P1, compounds of the formula II from Table P2 and intermediates listed in Tables P3-P4 can be prepared by analogous procedures. Either one of the following LC-MS methods was used to characterize the compounds:

Method A

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 µm particle size, 110 Angstöm, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B

MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 µm particle size, 110 Angstöm, 30×3 mm, Temp: 60° C.; DAD Wavelength range (nm): 200 to 500; Solvent gradient: A=water+0.05% v/v HCOOH, B=Acetonitril/Methanol (4:1, v:v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method C

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 100 to 900 Da.

LC: HP 1100 HPLC from Agilent: solvent degasser, quaternary pump (ZCQ), heated column compartment and diode-array detector. Column: Phenomenex Gemini C18, 3 µm particle size, 30×3 mm, Temp: 60° C.; DAD Wavelength range (nm): 210 to 500; Solvent gradient: A=water+5% v/v Methanol+0.05% v/v HCOOH, B=Acetonitril+0.05% v/v HCOOH.

| Time (min) | A % | B % | Flow (ml/min) |
|---|---|---|---|
| 0.00 | 100 | 0 | 1.700 |
| 2.00 | 0 | 100 | 1.700 |
| 2.80 | 0 | 100 | 1.700 |
| 2.90 | 100 | 0 | 1.700 |
| 3.00 | 100 | 0 | 1.700 |

Method D

MS: ZQ Mass Spectrometer from Waters (Single quadrupole mass spectrometer); Ionisation method: Electrospray; Polarity: positive and negative ions; Capillary (kV) 3.00, Cone (V) 30.00, Extractor (V) 2.00, Source Temperature (° C.) 150, Desolvation Temperature (° C.) 350, Cone Gas Flow (L/Hr) 50, Desolvation Gas Flow (L/Hr) 400; Mass range: 100 to 900 Da.

LC: Acquity UPLC from Waters: solvent degasser, binary pump, heated column compartment and diode-array detector. Column: Waters UPLC HSS T3, 1.8 µm, 30×2.1 mm, Temp: 60° C.; DAD Wavelength range (nm): 210 to 500; Solvent gradient: A=H$_2$O+5% MeOH+0.05% HCOOH, B=Acetonitril+0.05% HCOOH.

| Time (min) | A % | B % | Flow (ml/min) |
|---|---|---|---|
| 0.00 | 90.0 | 10.0 | 0.85 |
| 2.70 | 0.0 | 100.0 | 0.85 |
| 3.00 | 0.0 | 100.0 | 0.85 |

The characteristic values obtained for each compound were the retention time ("R$_t$", recorded in minutes) and the molecular ion as listed in Table P1, Table P2, Table P3 and in Table P4.

TABLE P1

Physical data of compounds of formula I:

| Compound No. | Structures | Melting Point | MS/NMR |
|---|---|---|---|
| P1.1 | 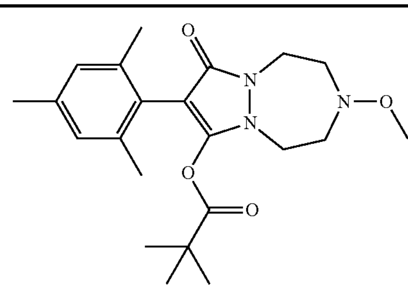 | 147-148° C. | LC/MS: 402 (M + H)$^+$ <br> R$_t$ = 1.79 min |

TABLE P1-continued

Physical data of compounds of formula I:

| Compound No. | Structures | Melting Point | MS/NMR |
|---|---|---|---|
| P1.2 | 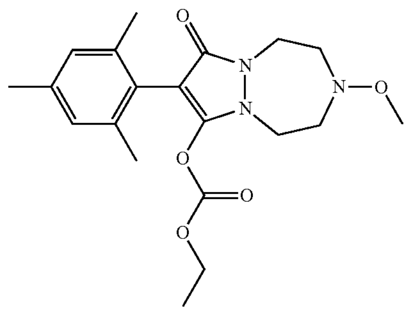 | solid | LC/MS: 309 (M + H)+ <br> R$_t$ = 1.63 min |
| P1.3 | 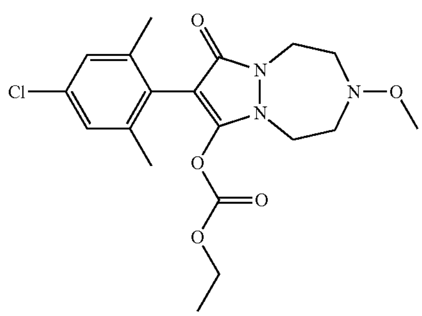 [SMILES: CCOC(=O)Oc1c(-c2c(C)cc(Cl)cc2C)c(=O)n2n1CCN(OC)CC2] | 114-116° C. | LC/MS: 410/412 (M + H)+ <br> R$_t$ = 1.67 min |
| P1.4 | 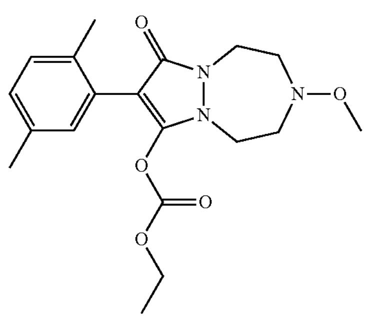 [SMILES: CCOC(=O)Oc1c(-c2cc(C)ccc2C)c(=O)n2n1CCN(OC)CC2] | gum | LC/MS: 376 (M + H)+ <br> R$_t$ = 1.58 min |
| P1.5 | 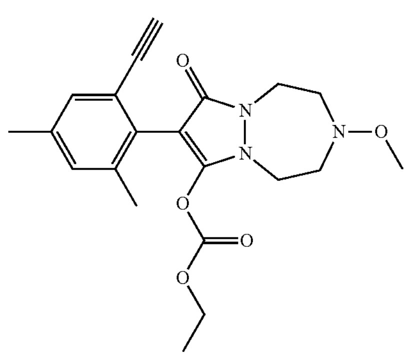 | 128-130° C. | LC/MS: 400 (M + H)+ <br> R$_t$ = 1.59 min |

TABLE P1-continued

Physical data of compounds of formula I:

| Compound No. | Structures | Melting Point | MS/NMR |
|---|---|---|---|
| P1.6 | 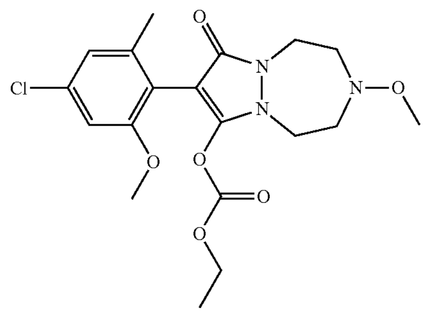 [SMILES: CCOC(=O)Oc1c(-c2c(C)cc(Cl)cc2OC)c(=O)n2n1CCN(OC)CC2] | gum | LC/MS: 426/428 (M + H)+<br>R$_t$ = 1.61 min |
| P1.7 | 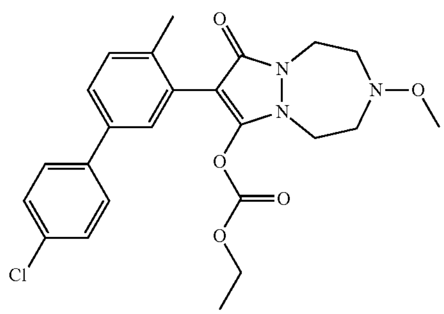 [SMILES: CCOC(=O)Oc1c(-c2cc(-c3ccc(Cl)cc3)ccc2C)c(=O)n2n1CCN(OC)CC2] | gum | LC/MS: 472/474 (M + H)+<br>R$_t$ = 1.86 min |
| P1.8 | 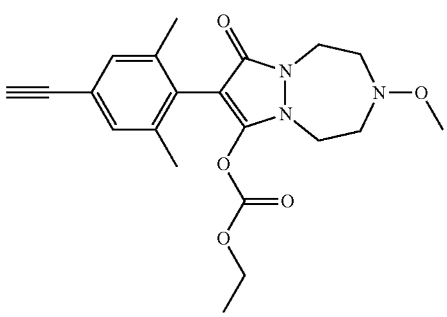 [SMILES: C#Cc1cc(C)c(-c2c(OC(=O)OCC)n3n(c2=O)CCN(OC)CC3)c(C)c1] | gum | LC/MS: 400 (M + H)+<br>R$_t$ = 1.62 min |
| P1.9 | 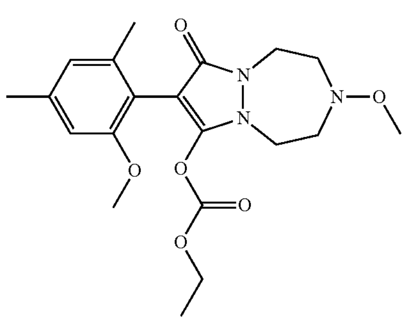 | 114-116° C. | LC/MS: 406 (M + H)+<br>R$_t$ = 1.58 min |

TABLE P1-continued

Physical data of compounds of formula I:

| Compound No. | Structures | Melting Point | MS/NMR |
|---|---|---|---|
| P1.10 | 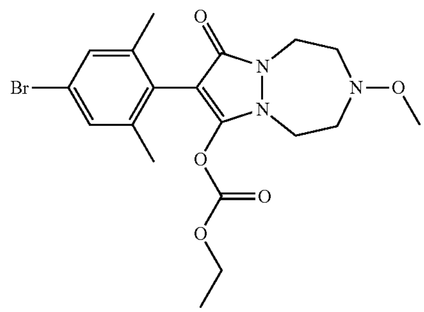 | 109-111° C. | LC/MS: 454/456 (M + H)+<br>R_t = 1.70 min |
| P1.11 | 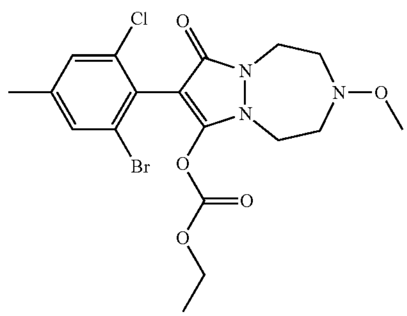 | 195-197° C. | LC/MS: 474/476/478 (M + H)+<br>R_t = 1.62 min |
| P1.12 | 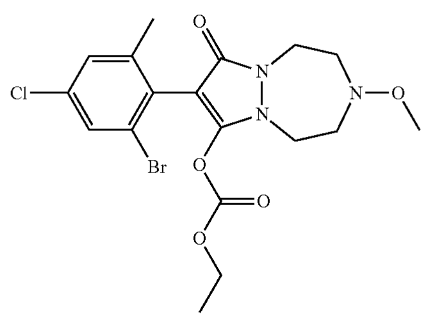 [SMILES: CCOC(=O)Oc1c(-c2c(C)cc(Cl)cc2Br)c(=O)n2n1CCN(OC)CC2] | 143-145° C. | LC/MS: 474/476/478 (M + H)+<br>R_t = 1.69 min |
| P1.13 | 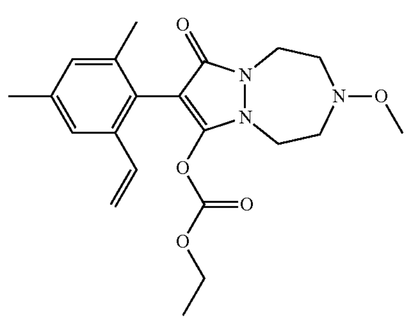 | gum | LC/MS: 402 (M + H)+<br>Rt = 1.66 min |

TABLE P1-continued

Physical data of compounds of formula I:

| Compound No. | Structures | Melting Point | MS/NMR |
|---|---|---|---|
| P1.14 | 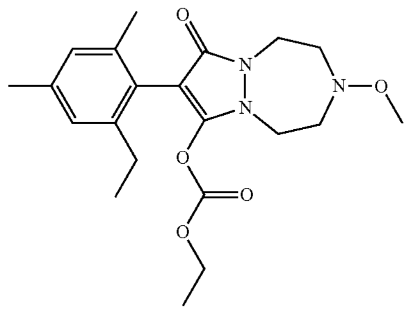 | gum | LC/MS: 404 (M + H)+<br>Rt = 1.71 min |
| P1.15 | 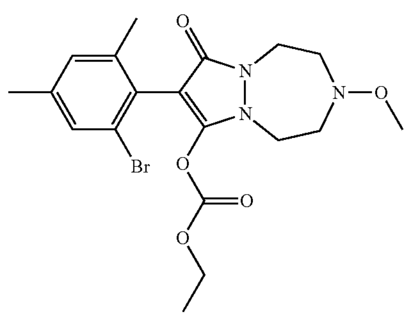 | 158-160° C. | LC/MS: 454/456 (M + H)+<br>Rt = 1.66 min |
| P1.16 | 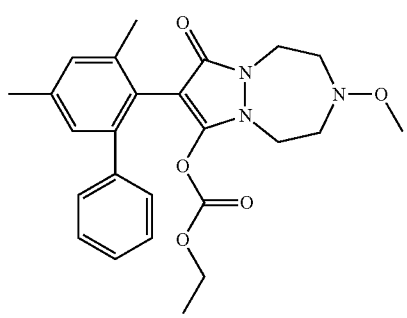 | gum | LC/MS: 452 (M + H)+<br>Rt = 1.80 min |
| P1.17 | 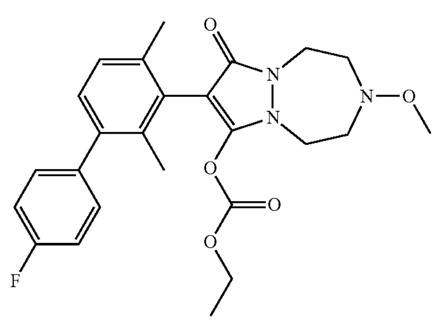 [SMILES: CCOC(=O)Oc1c(-c2c(C)ccc(-c3ccc(F)cc3)c2C)c(=O)n2n1CCN(OC)CC2] | gum | LC/MS: 470 (M + H)+<br>Rt = 1.64 min |

TABLE P1-continued

Physical data of compounds of formula I:

| Compound No. | Structures | Melting Point | MS/NMR |
|---|---|---|---|
| P1.18 | 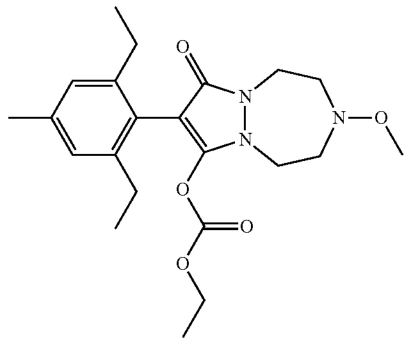 | gum | LC/MS: 418 (M + H)⁺<br>Rt = 1.57 min |
| P1.19 | 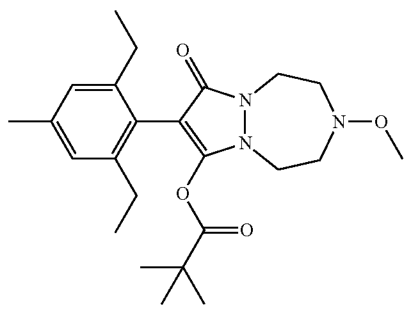 | gum | LC/MS: 430 (M + H)⁺<br>Rt = 1.83 min |
| P1.20 | 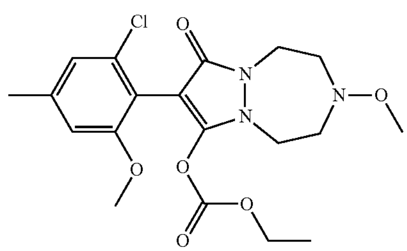 | 138-139° C. | LC/MS: 426/428 (M + H)⁺<br>Rt = 1.27 min |
| P1.21 | 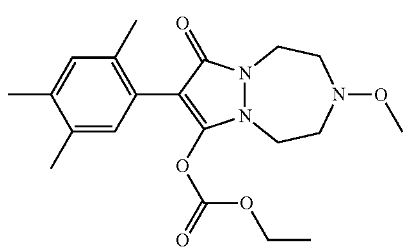 | 117-118° C. | LC/MS: 390 (M + H)⁺<br>Rt = 1.41 min |
| P1.22 | 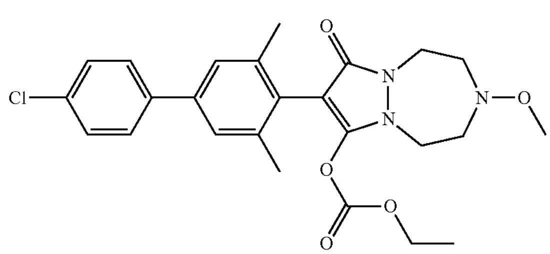 [SMILES: CCOC(=O)Oc1c(-c2c(C)cc(-c3ccc(Cl)cc3)cc2C)c(=O)n2n1CCN(OC)CC2] | gum | LC/MS: 486/488 (M + H)⁺<br>Rt = 1.79 min |

TABLE P1-continued

Physical data of compounds of formula I:

| Compound No. | Structures | Melting Point | MS/NMR |
|---|---|---|---|
| P1.23 | 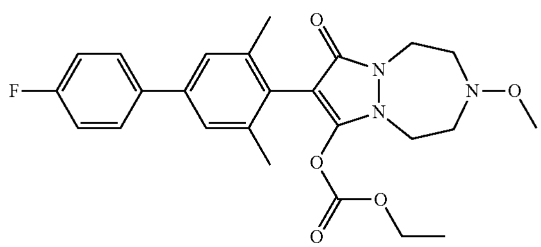 [SMILES: CCOC(=O)Oc1c(-c2c(C)cc(-c3ccc(F)cc3)cc2C)c(=O)n2n1CCN(OC)CC2] | gum | LC/MS: 470 (M + H)+<br>Rt = 1.66 min |

TABLE P2

Physical data of compounds of formula II:

| Compound No. | Structures | Melting Point | MS/NMR |
|---|---|---|---|
| P2.1 | 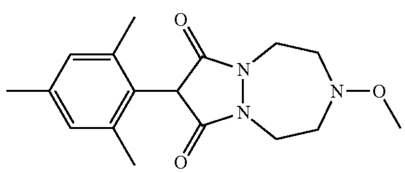 | 229-230° C. | LC/MS: 318 (M + H)+<br>$R_t$ = 1.44 min |
| P2.2 | 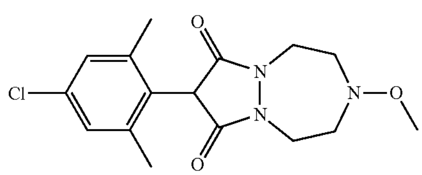 [SMILES: CON1CCN2C(=O)C(c3c(C)cc(Cl)cc3C)C(=O)N2CC1] | solid >275° C. | LC/MS: 338/340 (M + H)+<br>$R_t$ = 1.54 min |
| P2.3 | 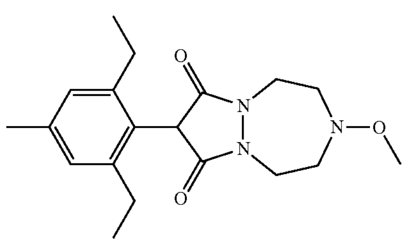 | 240° C. (dec) | LC/MS: 344 (M − H)−<br>$R_t$ = 1.68 min |
| P2.4 | 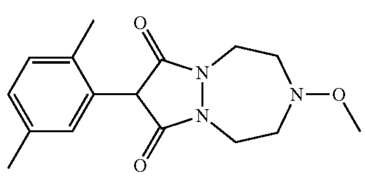 [SMILES: CON1CCN2C(=O)C(c3cc(C)ccc3C)C(=O)N2CC1] | 167-169° C. | LC/MS: 304 (M + H)+<br>$R_t$ = 1.38 min |
| P2.5 | 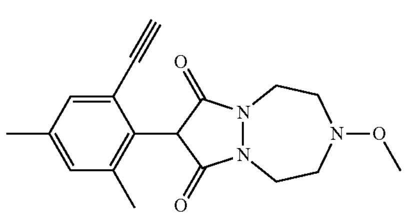 | solid | LC/MS: 328 (M + H)+<br>$R_t$ = 1.42 min |

TABLE P2-continued

Physical data of compounds of formula II:

| Compound No. | Structures | Melting Point | MS/NMR |
|---|---|---|---|
| P2.6 | 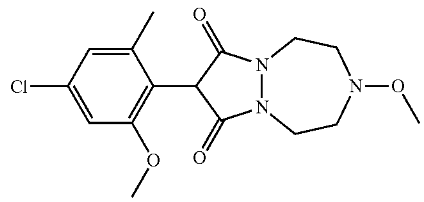 [SMILES: COc1cc(Cl)cc(C)c1C1C(=O)N2CCN(OC)CCN2C1=O] | solid | LC/MS: 354/356 (M + H)+<br>$R_t$ = 1.43 min |
| P2.7 | 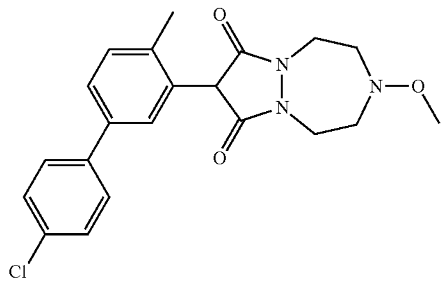 [SMILES: CON1CCN2C(=O)C(c3cc(-c4ccc(Cl)cc4)ccc3C)C(=O)N2CC1] | 248-250° C. | LC/MS: 400/402 (M + H)+<br>$R_t$ = 1.75 min |
| P2.8 | 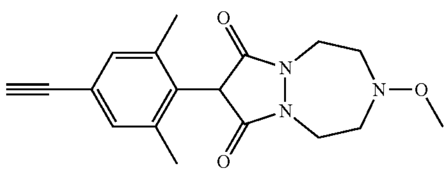 [SMILES: C#Cc1cc(C)c(C2C(=O)N3CCN(OC)CCN3C2=O)c(C)c1] | 265-267° C. | LC/MS: 328 (M + H)+<br>$R_t$ = 1.43 min |
| P2.9 | 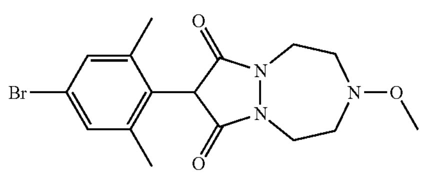 | 276-278° C. | LC/MS: 382/384 (M + H)+<br>$R_t$ = 1.50 min |
| P2.10 | 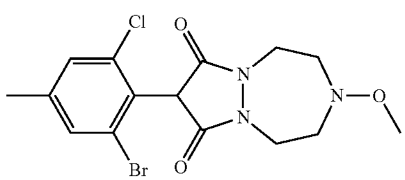 | solid | LC/MS: 402/404/406 (M + H)+<br>$R_t$ = 1.50 min |
| P2.11 | 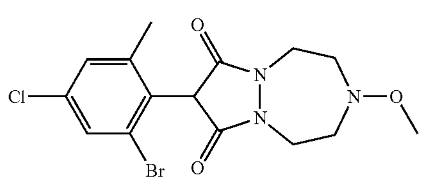 [SMILES: CON1CCN2C(=O)C(c3c(C)cc(Cl)cc3Br)C(=O)N2CC1] | 285° C. (dec) | LC/MS: 402/404/406 (M + H)+<br>$R_t$ = 1.51 min |
| P2.12 | 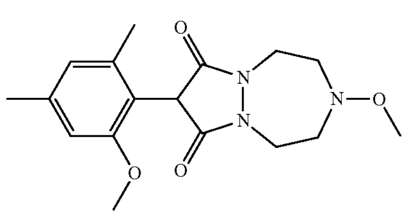 | solid | LC/MS: 334 (M + H)+<br>$R_t$ = 1.39 min |

TABLE P2-continued
Physical data of compounds of formula II:
| Compound No. | Structures | Melting Point | MS/NMR |
|---|---|---|---|
| P2.13 | 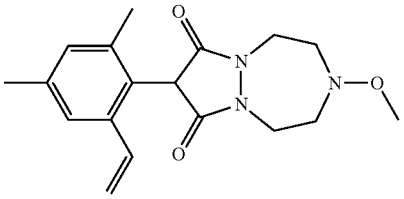 | 158-161° C. | LC/MS: 330 (M + H)+<br>Rt = 1.50 min |
| P2.14 | 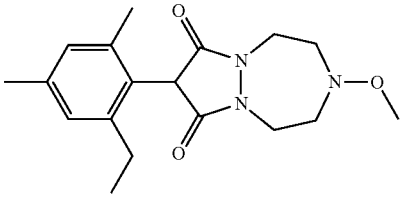 | 213-215° C. | LC/MS: 332 (M + H)+<br>Rt = 1.54 min |
| P2.15 | 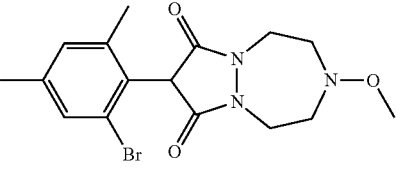 | 203-205° C. | LC/MS: 382/384 (M + H)+<br>$R_t$ = 1.47 min |
| P2.16 | 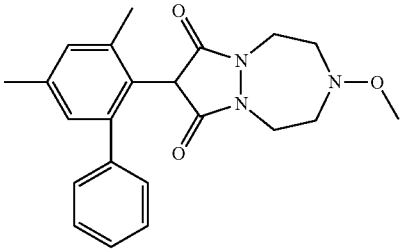 | solid | LC/MS: 380 (M + H)+<br>$R_t$ = 1.68 min |
| P2.17 | 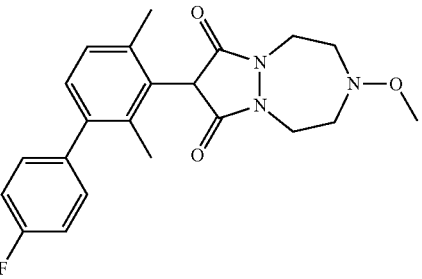 [SMILES: CON1CCN2C(=O)C(c3c(C)ccc(-c4ccc(F)cc4)c3C)C(=O)N2CC1] | 218-220° C. | LC/MS: 398 (M + H)+<br>$R_t$ = 1.47 min |
| P2.18 | 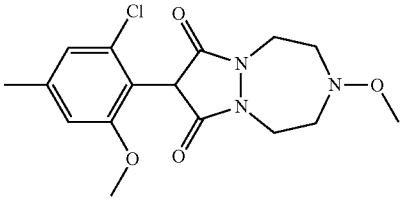 | gum | LC/MS: 354/356 (M + H)+<br>$R_t$ = 1.09 min |
| P2.19 | 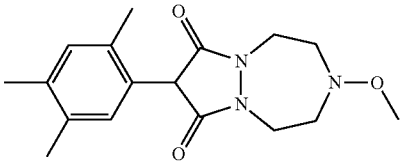 | 171-173° C. | LC/MS: 318 (M + H)+<br>$R_t$ = 1.19 min |

TABLE P2-continued

Physical data of compounds of formula II:

| Compound No. | Structures | Melting Point | MS/NMR |
|---|---|---|---|
| P2.20 | 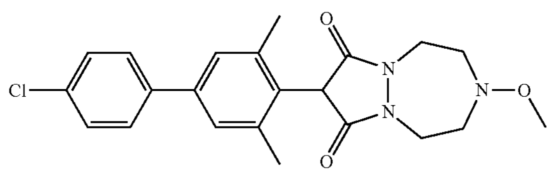 [SMILES: CON1CCN2C(=O)C(c3c(C)cc(-c4ccc(Cl)cc4)cc3C)C(=O)N2CC1] | 258-260° C. | LC/MS: 414/416 (M + H)$^+$<br>R$_t$ = 1.62 min |
| P2.21 | 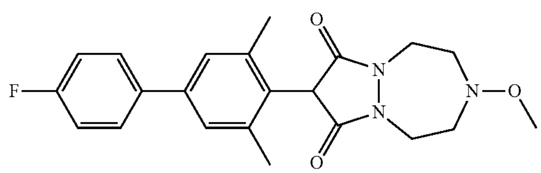 [SMILES: CON1CCN2C(=O)C(c3c(C)cc(-c4ccc(F)cc4)cc3C)C(=O)N2CC1] | 292-294° C. | LC/MS: 398 (M + H)$^+$<br>R$_t$ = 1.48 min |

TABLE P3

Physical data of intermediates of formula IV:

| Compound No. | Structures | Melting Point | MS/NMR |
|---|---|---|---|
| P3.1 | 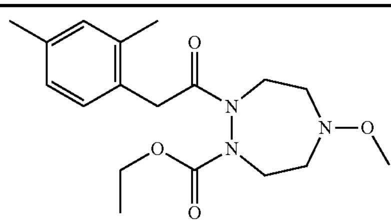 | oil | LC/MS: 364 (M + H)$^+$<br>R$_t$ = 1.80 min |
| P3.2 | 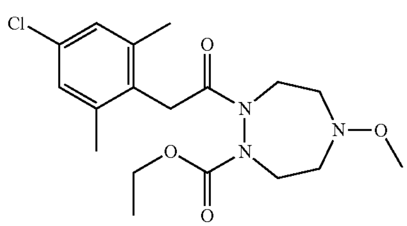 [SMILES: CCOC(=O)N1CCN(OC)CCN1C(=O)Cc1c(C)cc(Cl)cc1C] | 122-124° C. | LC/MS: 384/386 (M + H)$^+$<br>R$_t$ = 1.82 min |
| P3.3 | 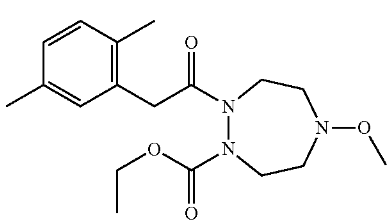 | viscous oil | LC/MS: 350 (M + H)$^+$<br>R$_t$ = 1.71 min |
| P3.4 | 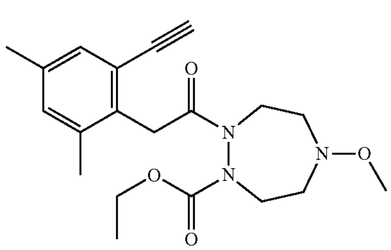 | viscous oil | LC/MS: 374 (M + H)$^+$<br>R$_t$ = 1.77 min |

TABLE P3-continued

Physical data of intermediates of formula IV:

| Compound No. | Structures | Melting Point | MS/NMR |
|---|---|---|---|
| P3.5 | 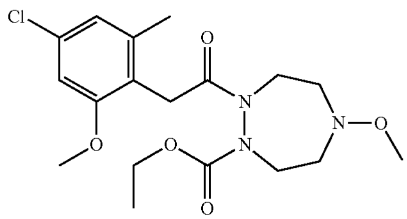 [SMILES: CCOC(=O)N1CCN(OC)CCN1C(=O)Cc1c(C)cc(Cl)cc1OC] | viscous oil | LC/MS: 400/402 (M + H)$^+$<br>R$_t$ = 1.78 min |
| P3.6 | 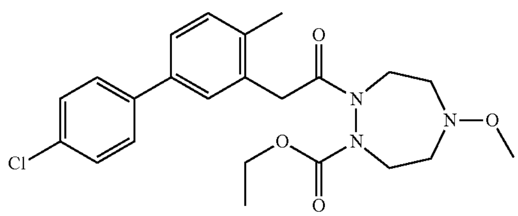 [SMILES: CCOC(=O)N1CCN(OC)CCN1C(=O)Cc1cc(-c2ccc(Cl)cc2)ccc1C] | viscous oil | LC/MS: 446/448 (M + H)$^+$<br>R$_t$ = 2.00 min |
| P3.7 | 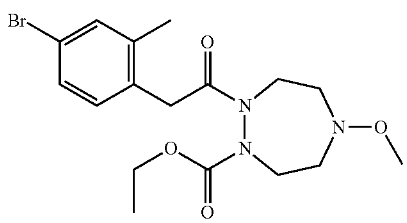 | 111-113° C. | LC/MS: 428/430 (M + H)$^+$<br>R$_t$ = 1.85 min |
| P3.8 | 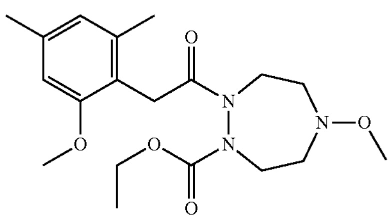 | gum | LC/MS: 380 (M + H)$^+$<br>R$_t$ = 1.76 min |
| P3.9 | 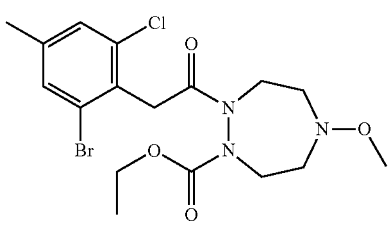 | gum | LC/MS: 448/450/452 (M + H)$^+$<br>R$_t$ = 1.88 min |
| P3.10 | 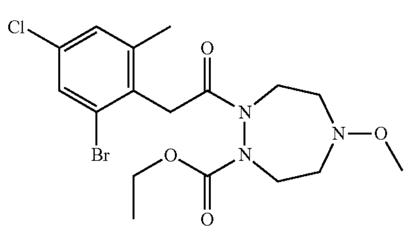 | gum | LC/MS: 448/450/452 (M + H)$^+$<br>R$_t$ = 1.88 min |
| P3.11 | 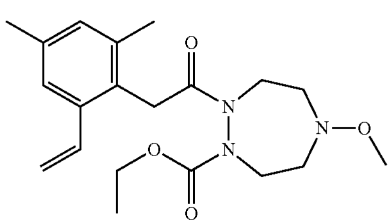 | gum | LC/MS: 376 (M + H)$^+$<br>R$_t$ = 1.86 min |

TABLE P3-continued

Physical data of intermediates of formula IV:

| Compound No. | Structures | Melting Point | MS/NMR |
|---|---|---|---|
| P3.12 | 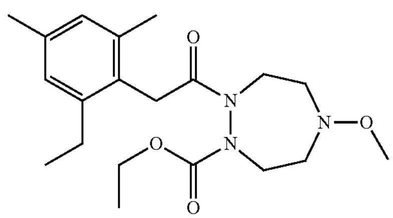 | gum | LC/MS: 378 (M + H)+<br>R$_t$ = 1.89 min |
| P3.13 | 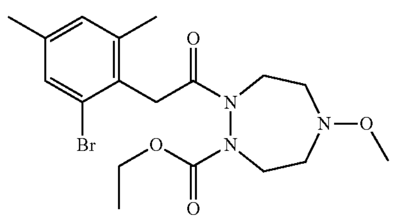 | gum | LC/MS: 428/430 (M + H)+<br>Rt = 1.86 min |
| P3.14 | 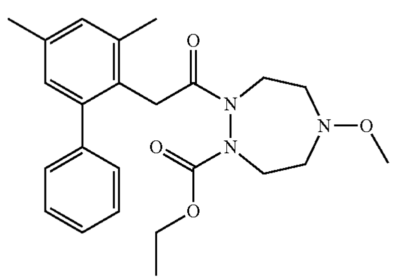 | solid | LC/MS: 426 (M + H)+<br>R$_t$ = 2.03 min |
| P3.15 | 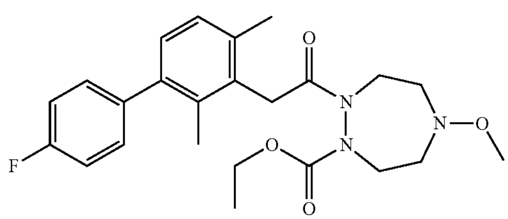 [SMILES: CCOC(=O)N1CCN(OC)CCN1C(=O)Cc1c(C)ccc(-c2ccc(F)cc2)c1C] | gum | LC/MS: 444 (M + H)+<br>R$_t$ = 1.90 min |
| P3.16 | 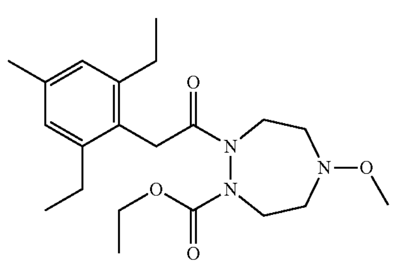 | gum | LC/MS: 392 (M + H)+<br>R$_t$ = 1.87 min |
| P3.17 | 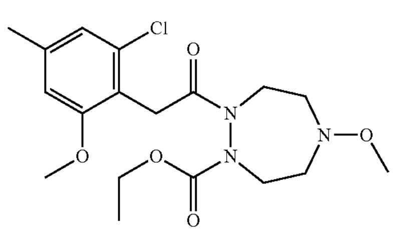 | gum | LC/MS: 400/402 (M + H)+<br>R$_t$ = 1.63 min |

TABLE P3-continued

Physical data of intermediates of formula IV:

| Compound No. | Structures | Melting Point | MS/NMR |
|---|---|---|---|
| P3.18 | 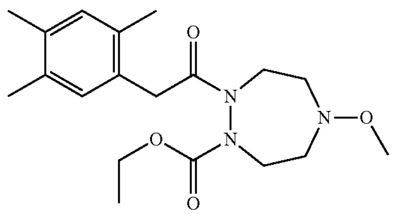 | gum | LC/MS: 364 (M + H)+<br>$R_t$ = 1.68 min |

TABLE P4

Physical data of intermediates of formula V, XIV or XV:

| Compound No. | Structures | Melting Point | MS/NMR |
|---|---|---|---|
| P4.1 | 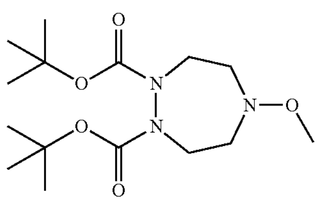 [SMILES: CON1CCN(C(=O)OC(C)(C)C)N(C(=O)OC(C)(C)C)CC1] | oil | $^1$H-NMR (400 MHz, CDCl$_3$):<br>δ 1.44 (s, 18H), 2.82-3.27 (m, 6H), 3.50 (s, 3H), 3.83-4.07 (m, 2H) ppm. |
| P4.2 | x HCl• | solid | GC-MS: 132 (M + H)+<br>$R_t$ = 2.92 min (free base) |
| P4.3 | 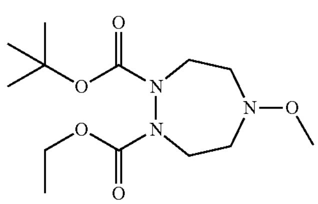 [SMILES: CCOC(=O)N1CCN(OC)CCN1C(=O)OC(C)(C)C] | oil | LC/MS: 326 (M + Na)+<br>$R_t$ = 1.58 min |
| P4.4 | x HCl• | solid | LC/MS: 204 (M + H)+<br>$R_t$ = 1.03 min (free base) |
| P4.5 | 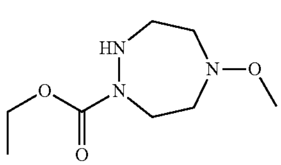 | oil | LC/MS: 204 (M + H)+<br>$R_t$ = 1.03 min |

Biological Examples

These examples illustrate the pesticidal/insecticidal properties of compounds of formula I.

Example B1

Activity Against *Myzus persicae* (Green Peach Aphid)

(Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in the tables above show good activity. In particular compounds P1.1, P1.2, P1.3, P1.5, P1.6, P1.7, P1.8, P1.9, P1.10, P1.12, P1.13, P1.14, P1.15, P1.17, P1.19, P2.1, P2.2, P2.5, P2.8, P2.9, P2.10, P2.11, P2.12, P2.13, P2.14, P2.15 and P2.17 show an activity of over 80% at a concentration of 400 ppm.

Example B2

Activity Against *Myzus persicae* (Green Peach Aphid)

(Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in the tables above show good activity. In particular compounds P1.1, P1.2, P1.3, P1.5, P1.6, P1.10, P1.11, P1.14, P1.15, P1.17, P1.18, P2.1, P2.2, P2.4, P2.5, P2.10, P2.11, P2.14, P2.15 and P2.17 show an activity of over 80% at a concentration of 400 ppm.

Example B3

Activity Against *Thrips tabaci* (Onion *Thrips*)

(Mixed Population, Feeding/Residual Contact Activity, Preventive)

Sunflower leaf discs are placed on agar in a 24-well microtiter plate and sprayed with test solutions. After drying, the leaf discs are infested with a *thrips* population of mixed ages. After an incubation period of 6 days, samples are checked for mortality and special effects (e.g. phytotoxicity).

In this test, compounds listed in the tables above show good activity. In particular compounds P1.1, P1.2, P1.17, P2.1 and P2.8 show an activity of over 80% at a concentration of 400 ppm.

Example B4

Activity Against *Tetranychus urticae* (Two-Spotted Spider Mite)

(Mixed Population, Feeding/Residual Contact Activity, Preventive)

Bean leaf discs on agar in 24-well microtiter plates are sprayed with test solutions. After drying, the leaf discs are infested with mite populations of mixed ages. 8 days later, discs are checked for egg mortality, larval mortality, and adult mortality.

In this test, compounds listed in the tables above show good activity. In particular compounds P1.1, P1.2, P1.3, P1.4, P1.5, P1.6, P1.7, P1.8, P1.14, P1.15, P1.18, P2.1, P2.2, P2.9, P2.12, P2.14 and P2.15 show an activity of over 80% at a concentration of 400 ppm.

Example B5

Activity Against *Myzus persicae* (Green Peach Aphid)

(Mixed Population, Feeding/Residual Contact Activity, Plant Damage Evaluation)

Cabbage plants infested with a mixed population of *Myzus persicae* are treated with diluted test solutions of the compounds in a spray chamber. 6 days after treatment, samples are checked for mortality and for plant damage (phytotoxicity), visual assessment being made using a 0-100% rating scale (100%=total damage to plant; 0%=no damage to plant).

In this test, compounds listed in the tables above show good activity against *Myzus persicae* and acceptable plant compatibility. For example compounds P1.2, P1.3, P1.4, P1.9, P1.10, P1.11, P1.12, P1.13, P1.14, P1.15, P1.17, P2.1, P2.2, P2.5, P2.10, P2.11, P2.12, P2.14, P2.15 and P2.17 show an activity of greater or equal to 80% against *Myzus persicae* and damage to cabbage plants less or equal to 10% at a concentration of 200 ppm.

These examples illustrate the herbicidal properties of compounds of formula I.

Test Plants:

*Lolium perenne* (LOLPE), *Alopecurus myosuroides* (ALOMY), *Echinochloa crus-galli* (ECHCG) and *Avena fatua* (AVEFA).

Example B6

Activity Against Weeds

Seeds of a variety of test species were sown in standard soil in pots. After cultivation for 8 days under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days, the test was evaluated (100=total damage to plant; 0=no damage to plant).

TABLE B6

| Post application on weeds | | | | |
| --- | --- | --- | --- | --- |
| Compound | LOLPE | ALOMY | ECHCG | AVEFA |
| P2.3 250 g/ha | 100 | 100 | 100 | 100 |
| P2.1 250 g/ha | 90 | 90 | 100 | 90 |
| P2.2 250 g/ha | 70 | 70 | 60 | 50 |
| P1.1 250 g/ha | 100 | 100 | 100 | 100 |
| P1.2 250 g/ha | 100 | 50 | 100 | 100 |
| P1.3 250 g/ha | 60 | 80 | 60 | 80 |
| P1.5 250 g/ha | 90 | 100 | 100 | 100 |

TABLE B6-continued

| Post application on weeds | | | | |
|---|---|---|---|---|
| Compound | LOLPE | ALOMY | ECHCG | AVEFA |
| P1.7 250 g/ha | 70 | 70 | 80 | 100 |
| P1.8 250 g/ha | 40 | 80 | 70 | 80 |
| P2.9 250 g/ha | 70 | 60 | 60 | 60 |
| P2.8 250 g/ha | 70 | 60 | 60 | 40 |
| P2.5 250 g/ha | 100 | 90 | 100 | 100 |
| P2.10 250 g/ha | 90 | 80 | 80 | 70 |
| P2.11 250 g/ha | 70 | 70 | 60 | 60 |
| P1.9 250 g/ha | 90 | 90 | 100 | 90 |
| P1.10 250 g/ha | 70 | 80 | 60 | 70 |
| P1.11 250 g/ha | 80 | 80 | 60 | 70 |
| P1.12 250 g/ha | 70 | 80 | 50 | 70 |
| P2.12 250 g/ha | 80 | 80 | 90 | 80 |

Example B7

Activity Against Weeds

Seeds of a variety of test species were sown in standard soil in pots. After cultivation for one day under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days, the test was evaluated (100=total damage to plant; 0=no damage to plant).

TABLE B7

| Pre application on weeds | | | | |
|---|---|---|---|---|
| Compound | LOLPE | ALOMY | ECHCG | AVEFA |
| P2.3 250 g/ha | 100 | 100 | 100 | 90 |
| P2.1 250 g/ha | 100 | 100 | 100 | 90 |
| P2.2 250 g/ha | 80 | 80 | 70 | 50 |
| P1.1 250 g/ha | 100 | 90 | 20 | 50 |
| P1.2 250 g/ha | 90 | 80 | 40 | 80 |
| P1.3 250 g/ha | 10 | 0 | 20 | 0 |
| P1.5 250 g/ha | 30 | 40 | 20 | 90 |
| P1.7 250 g/ha | 0 | 0 | 0 | 0 |
| P1.8 250 g/ha | 0 | 0 | 20 | 20 |
| P2.9 250 g/ha | 80 | 80 | 40 | 20 |
| P2.8 250 g/ha | 60 | 80 | 10 | 10 |
| P2.5 250 g/ha | 100 | 100 | 90 | 100 |
| P2.10 250 g/ha | 100 | 100 | 100 | 60 |
| P2.11 250 g/ha | 80 | 80 | 70 | 50 |
| P1.9 250 g/ha | 80 | 70 | 70 | 80 |
| P1.10 250 g/ha | 70 | 70 | 60 | 40 |
| P1.11 250 g/ha | 90 | 100 | 80 | 70 |
| P1.12 250 g/ha | 100 | 90 | 0 | 10 |
| P2.12 250 g/ha | 70 | 80 | 60 | 60 |

Example B8

Application with Safener (Cloquintocet-Mexyl)

Winter wheat seeds with a seed treatment of cloquintocet-mexyl applied at a rate of 0.5 g/kg seeds were sown in standard soil in pots. After cultivation for 8 days under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5).

The test plants were then grown in a glasshouse under controlled conditions in a glasshouse (at 24/16° C., day/night; 14 hours light; 65% humidity) and watered twice daily. After 13 days, the test was evaluated (100=total damage to plant; 0=no damage to plant).

TABLE B8

| Post application on wheat (TRZAW) | |
|---|---|
| Compound | TRZAW |
| P2.3 62.5 g/ha | 60 |
| P2.3 62.5 g/ha + 0.5 g/kg seeds cloquintocet-mexyl | 0 |
| P2.1 250 g/ha | 60 |
| P2.1 250 g/ha + 0.5 g/kg seeds cloquintocet-mexyl | 30 |
| P2.2 250 g/ha | 30 |
| P2.2 250 g/ha + 0.5 g/kg seeds cloquintocet-mexyl | 20 |
| P1.1 250 g/ha | 70 |
| P1.1 250 g/ha + 0.5 g/kg seeds cloquintocet-mexyl | 50 |
| P1.2 250 g/ha | 80 |
| P1.2 250 g/ha + 0.5 g/kg seeds cloquintocet-mexyl | 30 |
| P1.3 250 g/ha | 70 |
| P1.3 250 g/ha + 0.5 g/kg seeds cloquintocet-mexyl | 20 |
| P1.5 62.5 g/ha | 80 |
| P1.5 62.5 g/ha + 0.5 g/kg seeds cloquintocet-mexyl | 20 |
| P1.7 62.5 g/ha | 80 |
| P1.7 62.5 g/ha + 0.5 g/kg seeds cloquintocet-mexyl | 40 |
| P1.8 250 g/ha | 60 |
| P1.8 250 g/ha + 0.5 g/kg seeds cloquintocet-mexyl | 20 |
| P2.9 250 g/ha | 60 |
| P2.9 250 g/ha + 0.5 g/kg seeds cloquintocet-mexyl | 20 |
| P2.8 250 g/ha | 40 |
| P2.8 250 g/ha + 0.5 g/kg seeds cloquintocet-mexyl | 10 |
| P2.5 250 g/ha | 80 |
| P2.5 250 g/ha + 0.5 g/kg seeds cloquintocet-mexyl | 10 |
| P2.10 250 g/ha | 70 |
| P2.10 250 g/ha + 0.5 g/kg seeds cloquintocet-mexyl | 20 |
| P2.11 250 g/ha | 50 |
| P2.11 250 g/ha + 0.5 g/kg seeds cloquintocet-mexyl | 20 |
| P1.9 250 g/ha | 80 |
| P1.9 250 g/ha + 0.5 g/kg seeds cloquintocet-mexyl | 60 |
| P1.10 250 g/ha | 60 |
| P1.10 250 g/ha + 0.5 g/kg seeds cloquintocet-mexyl | 30 |
| P1.11 250 g/ha | 60 |
| P1.11 250 g/ha + 0.5 g/kg seeds cloquintocet-mexyl | 10 |
| P1.12 250 g/ha | 60 |
| P1.12 250 g/ha + 0.5 g/kg seeds cloquintocet-mexyl | 30 |
| P2.12 250 g/ha | 70 |
| P2.12 250 g/ha + 0.5 g/kg seeds cloquintocet-mexyl | 30 |

Further biological examples illustrating the pesticidal/insecticidal properties of compounds of formula I.

Example B9

Translaminar Activity Against *Aphis craccivora* (Cowpea Aphid)

French bean leaves (*Phaseolus vulgaris*) are infested with about 20 mixed age individuals on the lower leaf side using clip cages. 1 day after the infestation, the upper side of the leaves is treated with the test solution by painting. 5 days later, samples are checked for mortality.

In this test, compounds listed in the tables above show good activity. For example compounds P1.9, P1.10 and P2.1 show an activity of over 80% at a concentration of 200 ppm.

Example B10

Drench Activity Against *Myzus persicae* (Green Peach Aphid)

Pea seedlings cultivated in field soil are treated as drench application and infested with a mixed population of *M. persicae*. 7 days after infestation, samples are checked for mortality.

In this test, compounds listed in the tables above show good activity. For example compounds P1.2, P1.9, P2.1, P2.2 and P2.9 show an activity of over 80% at a concentration of 25 ppm.

Example B11

Activity Against *Nilaparvata lugens* (Brown Rice Planthopper)

(Larvicide, Feeding/Contact)

Rice seedlings are treated with the diluted test solutions in a spray chamber. After drying, they are infested with 20 $N_3$ nymphs (2 replicates). 6-12 days after the treatment samples are checked for mortality, growth regulation, and effects on the $F_1$ generation.

In this test, compounds listed in the tables above show good activity. For example compounds P1.2, P1.3, P1.9, P1.10, P2.1, P2.2 and P2.9 show an activity of over 80% at a concentration of 200 ppm.

Example B12

Activity Against *Bemisia tabaci* (Tobacco White Fly)

(Larvicide, Contact/Feeding)

Bean plants are infested with 20-30 adults that were removed after a 4 day egg-laying period. After another 7 days, bean plants with hatched nymphs (N-2) are treated (2 replicates) with the test solutions in a spray chamber. Three weeks later, samples are checked for number of emerged adults. Efficacy was calculated by comparing number of emerged adults in treated and non treated samples.

In this test, compounds listed in the tables above show good activity. For example compounds P1.2, P1.3, P1.9, P1.10, P2.2, P2.5 and P2.9 show an activity of over 80% at a concentration of 200 ppm.

Example B13

Activity Against *Aonidiella aurantii* (Red Scale)

Treatment of potato tubers by dipping the in the test solution. One day later, tubers are infested with about 50 crawlers. 6-8 weeks after application samples are checked for the number of crawlers of the next generation (compared to the non treated samples).

In this test, compounds listed in the tables above show good activity. For example compounds P1.2, P1.3, P1.10, P2.5 and P2.9 show an activity of over 80% at a concentration of 200 ppm.

The invention claimed is:

1. A compound of the formula I

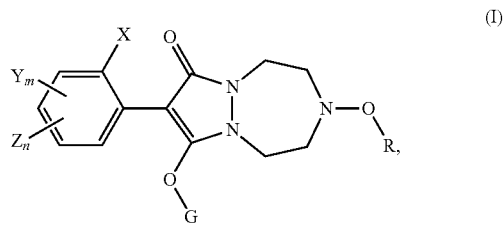

wherein
X, Y and Z, independently of each other, are $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl, halogen, or phenyl or phenyl substituted by $C_{1-4}$alkyl, $C_{1-4}$haloalkyl, halogen or cyano;
m and n, independently of each other, are 0, 1, 2 or 3 and m+n is 1, 2 or 3;
G is hydrogen, a metal, ammonium, sulfonium or a latentiating group;
R is hydrogen, $C_{1-6}$alkyl, $C_{1-6}$haloalkyl, $C_{1-6}$cyanoalkyl, $C_{2-6}$alkenyl, $C_{2-6}$haloalkenyl, $C_{3-6}$alkynyl, benzyl, $C_{1-4}$alkoxy($C_{1-4}$)alkyl or $C_{1-4}$alkoxy($C_{1-4}$)alkoxy($C_{1-4}$)alkyl;
and wherein, when G is a latentiating group, then G is selected from the groups phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;
wherein $X^a$, $X^b$, $X^c$, $X^d$, $X^e$ and $X^f$ are independently of each other oxygen or sulfur;
and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$ dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{is}$alkyl, $C_3$-$C_{is}$alkenyl, $C_3$-$C_{is}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_1$-$C_5$alkylamino$C_1$-$C_5$alkyl, $C_3$-$C_8$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro; or heteroaryl or heteroaryl substituted by $C_1$-$C_3$ alkyl, $C_1$-$_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_2$-$C_5$alkylaminoalkyl, $C_3$-$C_8$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy; or $R^c$ and $R^d$ are joined together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_5$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_5$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_5$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N-$C_1$-$C_5$alkylcarbonyl-N-$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$akylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

or an agrochemically acceptable salt or an N-oxide thereof.

2. A compound according to claim 1, wherein

X is methyl, ethyl, isopropyl, n-propyl, cyclopropyl, trifluoromethyl, methoxy, vinyl, ethynyl, fluoro, bromo, iodo or chloro;

Y and Z, independently of each other, are methyl, ethyl, n-propyl, isopropyl, cyclopropyl, trifluoromethyl, methoxy, vinyl, ethynyl, fluoro, bromo, iodo or chloro, phenyl or halo-substituted phenyl;

m and n, independently of each other, are 0, 1 or 2, and m+n is 1 or 2; and

R is hydrogen, methyl, ethyl, n-propyl, isopropyl, cyanomethyl, trifluoromethyl, 2,2,2-trifluoroethyl, allyl, 3,3-dichloroallyl, propargyl, benzyl, methoxymethyl, ethoxymethyl, methoxyethyl or methoxyethoxymethyl.

3. A process for the preparation of the compounds of the formula I according to claim 1, wherein G is hydrogen, which comprises cyclisation of the compound of formula IV

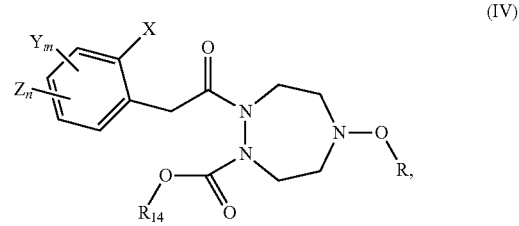

(IV)

wherein X, Y, Z, m, n, and R have the meanings assigned to them in claim 1, and $R_{14}$ is $C_{1-6}$alkyl, $C_{1-6}$haloalkyl, $C_{2-6}$alkenyl, phenyl or benzyl, under basic conditions.

4. A process for the preparation of the compounds of the formula I according to claim 1, wherein G is hydrogen, which comprises condensation of a compound of either the formula XIII-a or the formula XIII-b or the formula XVII,

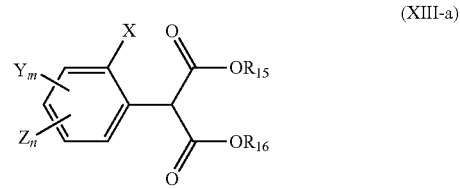

(XIII-a)

-continued

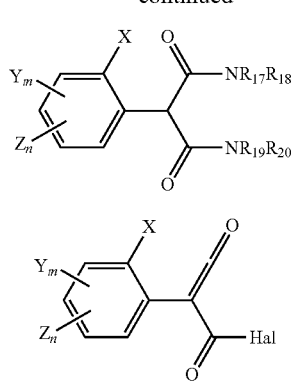

(XIII-b)

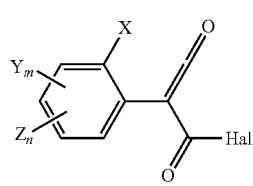

(XVII)

wherein X, Y, Z, m and n have the meanings assigned to them in claim 1, and in which $R_{15}$ and $R_{16}$ independently of each other are $C_{1-6}$alkyl, $C_{1-6}$haloalkyl, $C_{2-6}$alkenyl, phenyl or benzyl, and in which $R_{17}$, $R_{18}$, $R_{19}$ and $R_{20}$ independently of each other are hydrogen, $C_{1-6}$alkyl, $C_{1-6}$haloalkyl, $C_{2-6}$alkenyl, phenyl or benzyl, and in which Hal is a halogen, with a compound of formula XIV,

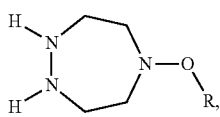

(XIV)

or a salt thereof, wherein R has the meanings assigned to it in claim 1, in an inert organic solvent, optionally in the presence of a base, and optionally under inert atmosphere.

5. A pesticidal or herbicidal composition comprising a pesticidally or herbicidally effective amount of at least one compound of formula I according to claim 1.

6. A composition according to claim 5, which, in addition to comprising the compound of formula I, comprises formulation adjuvants.

7. A method of combating and controlling pests which comprises applying a pesticidally effective amount of a compound of formula I according to claim 1, or of a composition comprising such a compound, to a pest, to a locus of a pest, or to a plant susceptible to attack by a pest.

8. A method of controlling grasses and weeds in crops of useful plants, which comprises applying a herbicidally effective amount of a compound of formula I according to claim 1, or of a composition comprising such a compound, to the plants or to the locus thereof.

9. A compound of the formula IV

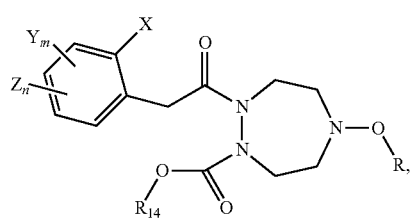

(IV)

or a salt thereof, wherein X, Y, Z, m, n and R have the meanings assigned to them according to claim 1, and $R_{14}$ is $C_{1-6}$alkyl, $C_{1-6}$haloalkyl, $C_{2-6}$alkenyl, phenyl or benzyl.

10. A compound of the formula XIV

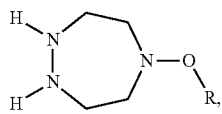

(XIV)

or a salt thereof, wherein R has the meanings assigned to it according to claim 1.

11. A compound of the formula V

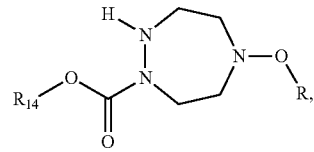

(V)

or a salt thereof, wherein R has the meanings assigned to it according to claim 1, and $R_{14}$ is $C_{1-6}$alkyl, $C_{1-6}$haloalkyl, $C_{2-6}$alkenyl, phenyl or benzyl.

12. A compound of the formula XV

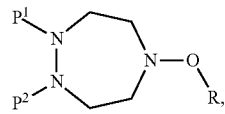

(XV)

or a salt thereof, wherein R has the meanings assigned to it according to claim 1, and in which $P^1$ and $P^2$ independently of each other are formyl, $C_{1-6}$alkylcarbonyl, $C_{1-6}$cycloalkylcarbonyl, $C_{1-6}$haloalkylcarbonyl, $C_{2-6}$alkenylcarbonyl, $C_{2-6}$alkenyloxycarbonyl, $C_{1-6}$alkoxycarbonyl, $C_{1-6}$haloalkoxycarbonyl, optionally substituted arylcarbonyl, optionally substituted aryloxycarbonyl, optionally substituted aryl($C_{1-6}$)alkoxycarbonyl, carbamoyl or a removable amino protective group.

13. A compound according to claim 1, wherein R is hydrogen, methyl, ethyl, n-propyl, isopropyl, cyanomethyl, trifluoromethyl, 2,2,2-trifluoroethyl, allyl, 3,3-dichloroallyl, propargyl, benzyl, methoxymethyl, ethoxymethyl, methoxyethyl or methoxyethoxymethyl.

14. A compound according to claim 1, wherein R is methyl, ethyl or methoxymethyl.

15. A compound according to claim 1, wherein X is $C_{1-4}$alkyl, $C_{3-6}$cycloalkyl, $C_{1-4}$haloalkyl, $C_{1-4}$alkoxy, $C_{2-6}$alkenyl, $C_{2-6}$alkynyl or halogen.

16. A compound according to claim 1, wherein X is methyl, ethyl, isopropyl, n-propyl, cyclopropyl, trifluoromethyl, methoxy, vinyl, ethynyl, fluoro, bromo, iodo or chloro.

17. A compound according to claim 1, wherein X is methyl, ethyl, methoxy, vinyl, ethynyl, bromo or chloro.

18. A compound according to claim 1, wherein Y and Z, independently of each other, are methyl, ethyl, n-propyl, isopropyl, cyclopropyl, trifluoromethyl, methoxy, vinyl, ethynyl, fluoro, bromo, iodo or chloro, phenyl or halo-substituted phenyl.

19. A compound according to claim 18, wherein the halo-substituted phenyl is 4-chlorophenyl or 4-fluorophenyl.

20. A compound according to claim 1, wherein m+n is 1 or 2.

21. A compound according to claim 1, wherein G is hydrogen, ethoxycarbonyl or pivaloyl.

22. A compound according to claim 1, wherein
R is methyl,
X is methyl, ethyl, methoxy, vinyl, ethynyl, bromo or chloro,
Y and Z, independently of each other, are methyl, ethyl, methoxy, vinyl, ethynyl, bromo, chloro, phenyl, 4-fluorophenyl or 4-chlorophenyl,
G is hydrogen, ethoxycarbonyl or pivaloyl, and
m+n is 1 or 2.

23. A compound according to claim 1, wherein
X is different from phenyl or phenyl substituted by $C_{1-4}$alkyl, $C_{1-4}$haloalkyl, halogen or cyano; and Y and Z are different from phenyl or phenyl substituted by $C_{1-4}$alkyl, $C_{1-4}$haloalkyl, halogen or cyano, when they occupy the ortho-position of the phenyl substituent to which they are attached.

24. A compound according to claim 1, wherein
if Y is a phenyl substituent on positions 4 or 5 of the phenyl ring, then m is 1, n is 0 and X is methyl or ethyl.

\* \* \* \* \*